(12) United States Patent
Oshiyama et al.

(10) Patent No.: US 9,923,154 B2
(45) Date of Patent: Mar. 20, 2018

(54) ORGANIC ELECTROLUMINESCENT ELEMENT, LIGHTING DEVICE, AND DISPLAY DEVICE

(75) Inventors: Tomohiro Oshiyama, Hachioji (JP); Hiroshi Kita, Hachioji (JP); Dai Ikemizu, Hachioji (JP); Masato Nishizeki, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 863 days.

(21) Appl. No.: 13/985,316

(22) PCT Filed: Feb. 10, 2012

(86) PCT No.: PCT/JP2012/053077
§ 371 (c)(1),
(2), (4) Date: Aug. 14, 2013

(87) PCT Pub. No.: WO2012/111548
PCT Pub. Date: Aug. 23, 2012

(65) Prior Publication Data
US 2013/0328037 A1 Dec. 12, 2013

(30) Foreign Application Priority Data
Feb. 16, 2011 (JP) .................. 2011-030626

(51) Int. Cl.
*H01L 51/00* (2006.01)
*C07F 9/50* (2006.01)
(Continued)

(52) U.S. Cl.
CPC ........ *H01L 51/0085* (2013.01); *C07F 9/5022* (2013.01); *C07F 15/0026* (2013.01);
(Continued)

(58) Field of Classification Search
CPC ............ H01L 51/5016; H01L 51/0072; H01L 51/0073; H01L 51/0074
See application file for complete search history.

(56) References Cited

U.S. PATENT DOCUMENTS

| 2005/0260441 A1 | 11/2005 | Thompson et al. | |
|---|---|---|---|
| 2011/0017988 A1* | 1/2011 | Yasukawa | H01L 51/004 257/40 |

FOREIGN PATENT DOCUMENTS

| JP | 2006-523231 | 10/2006 |
|---|---|---|
| JP | 2007-305783 | 11/2007 |

(Continued)

OTHER PUBLICATIONS

JP 2009-272339, machine translation (2009).*
(Continued)

*Primary Examiner* — Robert A Vetere
(74) *Attorney, Agent, or Firm* — Lucas & Mercanti, LLP

(57) ABSTRACT

An object of the present invention is to provide an organic electroluminescent element that has low drive voltage, high emission efficiency, long endurance and an excellent effect of preventing generation of dark spots. Another object of the present invention is to provide a lighting device and a display device each including the organic electroluminescent element. The organic electroluminescent element according to the present invention includes an anode, a cathode, and an emissive layer, and the organic electroluminescent element includes a layer containing compound A that has a difference of 0 nm or more and 5 nm or less between the maximum emission wavelength on the shortest wavelength side in an emission spectrum measured at 300 K and the maximum emission wavelength on the shortest wavelength side in an emission spectrum measured at 77 K.

7 Claims, 6 Drawing Sheets

(51) Int. Cl.
- *C07F 15/00* (2006.01)
- *G09F 9/33* (2006.01)
- *C09K 11/06* (2006.01)
- *H05B 33/14* (2006.01)
- *H01L 51/50* (2006.01)

(52) U.S. Cl.
CPC ...... *C07F 15/0033* (2013.01); *C07F 15/0086* (2013.01); *C07F 15/0093* (2013.01); *C09K 11/06* (2013.01); *G09F 9/33* (2013.01); *H01L 51/0084* (2013.01); *H05B 33/14* (2013.01); *C09K 2211/185* (2013.01); *H01L 51/0067* (2013.01); *H01L 51/0072* (2013.01); *H01L 51/0073* (2013.01); *H01L 51/0074* (2013.01); *H01L 51/5016* (2013.01); *H01L 2251/55* (2013.01)

(56) References Cited

FOREIGN PATENT DOCUMENTS

| | | |
|---|---|---|
| JP | 2009-004753 | 1/2009 |
| JP | 2009-272339 | 11/2009 |
| JP | 2010-118381 | 5/2010 |
| JP | 2010-135467 | 6/2010 |
| JP | 2010135467 A * | 6/2010 |
| JP | 2010-254642 | 11/2010 |
| WO | 2004/085450 | 7/2004 |
| WO | 2008/035571 | 3/2008 |
| WO | 2009/003898 | 1/2009 |
| WO | 2009/060757 | 5/2009 |
| WO | 2010044342 A1 | 4/2010 |

OTHER PUBLICATIONS

JP2010-135467, machine translation, 2010.*
Hisahiro Sasabe, et al, Advanced Materials, vol. 22, pp. 5003-5007 (2010).
Yoshiaki Sakurai, et al, The 71st Academic Lecture; The Japan Society of Applied Physics (Autumn 2010, Nagasaki Univeristy, 17 p. -ZK-5).
Japanese IPRP (Chapter I of the PCT) Form PCT/IB/373, date of issuance: Aug. 21, 2013 (5 pages).
English translation of Japanese IPRP (Chapter I of the PCT) Form PCT/IB/373, date of issuance: Aug. 21, 2013 (6 pages).
Extended European Search Report dated May 27, 2016 from corresponding European Application; Application No./ Patent No. 12746917.9-1552 / 2677561 PC/JP2012053077; Applicant: Konica Minolta, Inc.; Total of 7 pages.

* cited by examiner

ORGANIC ELECTROLUMINESCENT ELEMENT, LIGHTING DEVICE, AND DISPLAY DEVICE

CROSS-REFERENCE TO RELATED APPLICATIONS

This application is a 371 of PCT/JP2012/053077 filed on Feb. 10, 2012, which claims the priority of Japanese Patent Application No. 2011-030626 filed on Feb. 16, 2011, the contents of each of which are incorporated herein by reference.

TECHNICAL FIELD

The invention relates to an organic electroluminescent element, a lighting device and a display device, and more particularly to an organic electroluminescent element and a compound suitable for use in the organic electroluminescent element.

BACKGROUND ART

Electroluminescent displays (ELDs) have already been used in emissive electronic display devices. One of components of an ELD is an inorganic electroluminescent element or an organic electroluminescent element (hereinafter, referred to as an organic EL element). The inorganic electroluminescent element has been used as a planar light source. Such an emissive element, however, requires high voltage of alternating driving current.

The organic EL element has a structure of an emissive layer containing an emissive compound interposed between a cathode and an anode. Electrons and holes are injected, into the emissive layer and are recombined to form excitons. When, this exciton is deactivated, emission of light (fluorescence or phosphorescence) occurs. This organic EL element can emit light by such a phenomenon at a voltage of several to several tens of volts. Moreover, the organic EL element has a wide viewing angle and a high visibility because it is a self-luminescent element. Furthermore, the organic EL element, which is a thin-film type of full solid-state element, is attracting attention from the points of view of space saving and of portability.

An example development of the organic EL elements for practical use is an organic EL element utilizing phosphorescent emission from an excited triplet state reported by Princeton University (M. A. Baldo et al., nature, Vol. 395, pp. 151-154, 1998). As described in U.S. Pat. No. 6,097,147 and M. A. Baldo et al., nature, Vol. 403, No. 17, pp. 750-753 (2000), research on materials to generate phosphorescence at room temperature has been carried out more actively since then.

Moreover, a recently discovered organic EL element utilizing phosphorescent emission can achieve emission efficiency, in principle, about four times higher than those of previous elements utilizing fluorescent emission. Research and development works on the layer structure of emissive elements and electrodes are being carried out worldwide as well as development work on materials for the recently discovered organic EL element.

For example, many compounds have been synthesized and examined mainly for heavy metal complexes such as a series of iridium complexes, and have been used for an emissive layer in an organic electroluminescent element (also called as an organic EL element) as described in S. Lamansky et al., J. Am. Chem. Soc., Vol. 123, p. 4304 (2001), for example.

Although an organic EL device utilizing phosphorescent emission is a system of great potential, major technical issues for the device are the way of controlling the position of the emissive center, particularly stable recombination inside the emissive layer and stable emission of light, as well as enhancement of the emissive property of a phosphorescent compound itself, from the viewpoints of efficiency and lifetime of the element.

In order to enhance the emissive property of a phosphorescent compound, there are two possible approaches: (1) increasing the radiative rate constant (kr) and (2) decreasing the non-radiative rate constant (knr), when the lowest excited triplet state (T1) is deactivated to the ground state (S0).

A possible specific means for decreasing the non-radiative rate constant (knr) is to sterically control the structure of a ligand of the phosphorescent compound to decrease structural changes between the ground state and the excited state.

With regard, to the iridium complex, which is a typical phosphorescent compound, examples in which the steric structure is controlled by a combinated ligand of dibenzofuran and pyridine are described in, for example, Japanese Patent Application Laid-Open Publication Nos. 2002-332291, 2005-23071 and 2002-23072.

Similar applications are described for iridium complexes formed with phenylpyrazole derivatives (see Patent Literatures 1 and 5), phenylimidazole derivatives (see Patent Literatures 2 and 3), and derivatives containing a carbene moiety as a ligand (see Patent Literature 4 and Non Patent Literature 1).

A platinum complex including a ligand having π (pai)-conjugation extending over the benzene ring of the ligand is synthesized (Non Patent Literature 2).

These complexes are, however, not satisfactory in terms of providing an organic EL element that has nigh emission efficiency and low drive voltage, excels in heat endurance and raw storability, and has a long lifetime. A further solution is therefore being sought.

CITATION LIST

Patent Literature (PTL)

PTL 1: International Publication No. WO2004/085450
PTL 2: International Publication No. WO2009/060757
PTL 3: Japanese Patent Application Laid-Open Publication No. 2010-135467
PTL 4: International Publication No. WO2009/003898
PTL 5: Japanese Patent Application Laid-Open Publication No. 2010-254642

Non Patent Literature (NPL)

NPL 1: Hisahiro Sasabe et al., Advanced Materials, Vol. 22, pp. 5003-5007 (2010)
NPL 2: Yoshiaki Sakurai et al., The 71th Academic Lecture; The Japan Society of Applied Physics (Autumn 2010, Nagasaki University, 17p-ZK-5)

SUMMARY OF INVENTION

Technical Problem

An object of the present invention is to provide an organic electroluminescent element that has low drive voltage, high emission efficiency, high durability and an excellent effect of preventing dark spots from forming. Another object of the present invention is to provide a lighting device and a display device each including the organic electroluminescent element.

Means to Solve the Problem

The objects described above of the present invention can be achieved by means (aspects) described below.

1. An organic electroluminescent element including an anode, a cathode, and an emissive layer, and the organic electroluminescent element includes a layer containing compound A. The compound A has a difference, between a maximum emission wavelength on a shortest wavelength side in an emission spectrum measured at 300 K and a maximum emission wavelength on a shortest wavelength side in an emission spectrum measured at 77 K, of 0 nm or more and 5 nm or less.

2. The organic electroluminescent element of an aspect 1, in which the layer containing the compound A is the emissive layer.

3. The organic electroluminescent element of an aspect 1 or 2, in which the compound A is a phosphorescent compound.

4. The organic electroluminescent element of any one of aspects 1 to 3, in which the compound A is a compound represented by Formula (1):

[Chem. 1]

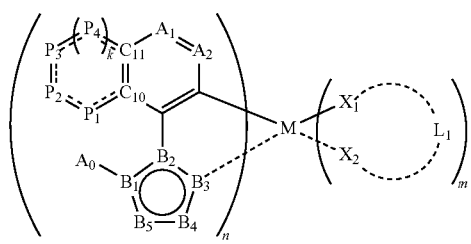

Formula (1)

(where, $C_{10}$ and $C_{11}$ each represent a carbon atom; $A_1$ and $A_2$ each represent a nitrogen atom or CRa; Ra represents a hydrogen atom or a substituent; $P_1$ represents an oxygen atom, a nitrogen atom, or a sulfur atom; $P_2$, $P_3$ and $P_4$ each represent CRb, C(RcRd), a nitrogen atom, NRe, Si(RfRg), an oxygen atom or a sulfur atom; Rb, Rc, Rd, Re, Rf and Rg each represent a hydrogen atom or a substituent; Rb, Rc, Rd and Re do not form any ring by mutual bounding.

$A_0$ represents an aromatic hydrocarbon ring group or an aromatic heterocyclic group; k represents 0 or an integer of 1; $B_1$ to $B_5$ each represent a carbon atom, $CR_0$, a nitrogen atom, an oxygen atom or a sulfur atom, provided that at least one of $B_1$ to $B_5$ represents a nitrogen atom, and these five atoms forms a five-membered aromatic nitrogen-containing heterocyclic ring; $R_0$ represents a hydrogen atom or a substituent; $X_1$-$L_1$-$X_2$ represents a bidentate ligand; $X_1$ and $X_2$ each independently represent a carbon atom, a nitrogen atom or on oxygen atom; the bonds between $C_{11}$ and $P_4$, $C_{11}$ and $P_3$, $P_4$ and $P_3$, $P_3$ and $P_2$, $P_2$ and $P_1$, and $P_1$ and $C_{10}$ are each a single bond or double bond; $L_1$ represents an atomic group that forms a bidentate ligand with $X_1$ and $X_2$; n represents an integer of 1 to 3; m represents an integer of (3-n); and M represents a transition metal element in Groups VIII to X of a periodic table.)

5. The organic electroluminescent element of an aspect 4, in which the compound represented by the Formula (1) is a compound represented by Formula (2):

[Chem. 2]

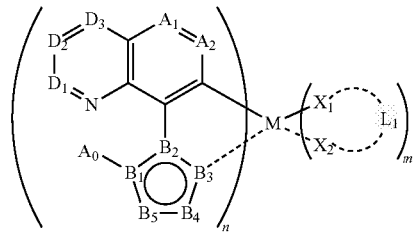

Formula (2)

(where, $A_1$ and $A_2$ each represent a nitrogen atom or CRa.
Ra represents a hydrogen atom or a substituent.
$D_1$, $D_2$ and $D_3$ each represent CRb or a nitrogen atom.
Rb represents a hydrogen atom or a substituent; Rbs do not form any ring by mutual bounding.

$A_0$ represents an aromatic hydrocarbon ring group or an aromatic heterocyclic group; $B_1$ to $B_5$ each represent a carbon atom, $CR_0$, a nitrogen atom, an oxygen atom or a sulfur atom, provided, that at least one of $B_1$ to $B_5$ represents a nitrogen atom; $R_0$ represents a hydrogen atom or a substituent.

$X_1$-$L_1$-$X_2$ represents a bidentate ligand; $X_1$ and $X_2$ each independently represent a carbon atom, a nitrogen atom or an oxygen atom; $L_1$ represents an atomic group that forms a bidentate ligand with $X_1$ and $X_2$; n represents an integer of 1 to 3; m represents an integer of (3-n); and M represents a transition metal element, in Groups VIII to X of the periodic table.)

6. The organic electroluminescent element of an aspect 4, in which the compound represented by the Formula (1) is a compound represented by Formula (3):

[Chem. 3]

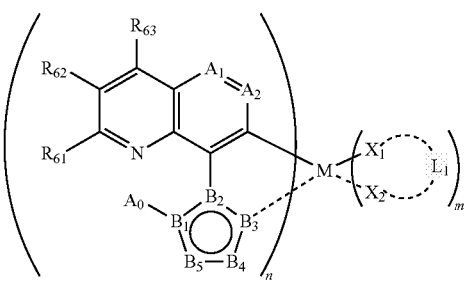

Formula (3)

(where, $A_1$ and $A_2$ each represent a nitrogen atom or CRa.
Ra represents a hydrogen atom or a substituent.
$R_{61}$, $R_{62}$ and $R_{63}$ each represent a hydrogen atom or a substituent; $A_0$ represents an aromatic hydrocarbon ring group or an aromatic heterocyclic group; $R_{61}$, $R_{62}$ and $R_{63}$ do not form any ring by mutual bounding.

$B_1$ to $B_5$ each represent a carbon atom, $CR_0$, a nitrogen atom, an oxygen atom or a sulfur atom, provided that at least one of $B_1$ to $B_5$ represents a nitrogen atom; $R_0$ represents a hydrogen atom or a substituent.

$X_1$-$L_1$-$X_2$ represents a bidentate ligand; $X_1$ and $X_2$ each independently represent a carbon atom, a nitrogen atom or an oxygen atom; $L_1$ represents an atomic group that forms a bidentate ligand with $X_1$ and $X_2$; n represents an integer of 1 to 3; m represents an integer of (3-n); and M represents a transition metal element in Groups VIII to X of the periodic table.)

7. The organic electroluminescent element of an aspect 4, in which the compound represented by the Formula (1) is a compound represented by Formula (4):

[Chem. 4]

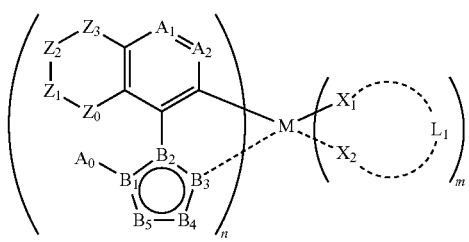

Formula (4)

(where, $A_1$ and $A_2$ each represent a nitrogen atom or CRa.

Ra represents a hydrogen atom or a substituent.

$Z_0$ represents an oxygen atom or a sulfur atom.

$Z_1$, $Z_2$ and $Z_3$ each represent C(RcRd), NRe, Si(RfRg), an oxygen atom or a sulfur atom.

Rc, Rd, Re, Rf and Rg each represent a hydrogen atom or a substituent; Rc, Rd and Re do not form airy ring by mutual bounding.

$A_0$ represents an aromatic hydrocarbon ring group or an aromatic heterocyclic group.

$B_1$ to $B_5$ each represent a carbon atom, $CR_0$, a nitrogen atom, an oxygen atom or a sulfur atom, provided that at least one of $B_1$ to $B_5$ represents a nitrogen atom; $R_0$ represents a hydrogen atom or a substituent.

$X_1$-$L_1$-$X_2$ represents a bidentate ligand; $X_1$ and $X_2$ each independently represent a carbon atom, a nitrogen atom or an oxygen atom.

$L_1$ represents an atomic group that forms a bidentate ligand with $X_1$ and $X_2$; n represents an integer of 1 to 3; m represents an integer of (3-n).

M represents a transition metal element in Groups VIII to X of the periodic table.)

8. The organic electroluminescent element of an aspect 4, in which the compound represented by the Formula (1) is a compound, represented by Formula (5):

[Chem. 5]

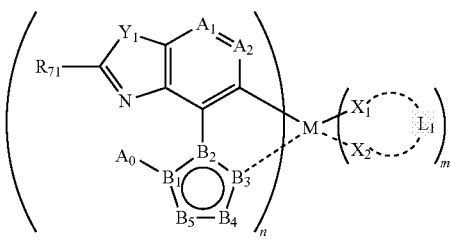

Formula (5)

(where, $A_1$ and $A_2$ each represent a nitrogen atom or CRa; Ra represents a hydrogen atom or a substituent.

$Y_1$ represents an oxygen atom, a sulfur atom, C(RcRd), NRe or Si(RfRg).

Rc, Rd, Re, Rf and Rg each represent a hydrogen atom or a substituent.

$R_{71}$ represents a hydrogen atom or a substituent; $R_{71}$, Rc and Rd do not form any ring by mutual bounding.

$A_0$ represents an aromatic hydrocarbon ring group or an aromatic heterocyclic group.

$B_1$ to $B_5$ each represent a carbon atom, $CR_0$, a nitrogen atom, an oxygen atom or a sulfur atom, provided that at least one of $B_1$ to $B_5$ represents a nitrogen atom; $R_0$ represents a hydrogen atom or a substituent.

$X_1$-$L_1$-$X_2$ represents a bidentate ligand; $X_1$ and $X_2$ each independently represent a carbon atom, a nitrogen atom or an oxygen atom.

$L_1$ represents an atomic group that forms a bidentate ligand with $X_1$ and $X_2$; n represents an integer of 1 to 3; m represents an integer of (3-n).

M represents a transition metal element in Groups VIII to X of the periodic table.)

9. The organic electroluminescent element of an aspect 4, in which the compound represented by the Formula (1) is a compound represented by Formula (6):

[Chem. 6]

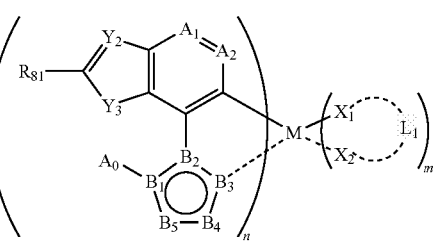

Formula (6)

(where, $A_1$ and $A_2$ each represent a nitrogen atom or CRa.

Ra represents a hydrogen atom or a substituent.

$Y_2$ represents a nitrogen atom or CRb.

Rb represents a hydrogen atom or a substituent.

$Y_3$ represents an oxygen atom or a sulfur atom.

$R_{81}$ represents a hydrogen atom or a substituent; $R_{81}$ and Rb do not form any ring by mutual bounding.

$A_0$ represents an aromatic hydrocarbon ring group or an aromatic heterocyclic group.

$B_1$ to $B_5$ each represent a carbon atom, $CR_0$, a nitrogen atom, an oxygen atom or a sulfur atom, provided that at least one of $B_1$ to $B_5$ represents a nitrogen atom; $R_0$ represents a hydrogen atom or a substituent.

$X_1$-$L_1$-$X_2$ represents a bidentate ligand; $X_1$ and $X_2$ each independently represent a carbon atom, a nitrogen atom or an oxygen atom.

$L_1$ represents an atomic group that forms a bidentate ligand with $X_1$ and $X_2$; n represents an integer of 1 to 3; m represents an integer of (3-n).

M represents a transition metal element in Groups VIII to X of the periodic table.)

10. The organic electroluminescent element of an aspect 4, in which the compound represented by the Formula (1) is a compound represented by Formula (7):

[Chem. 7]

Formula (7)

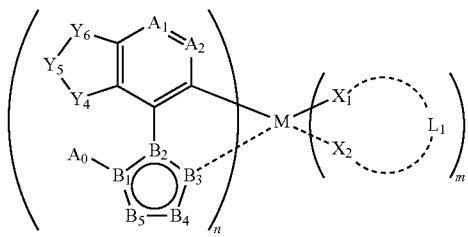

(where, $A_1$ and $A_2$ each represent a nitrogen atom, or CRa.

Ra represents a hydrogen atom or a substituent; $Y_4$ represents an oxygen atom or a sulfur atom.

$Y_5$ and $Y_6$ each represent C(RcRd), NRe, Si(RfRg), an oxygen, atom or a sulfur atom.

Rc, Rd, Re, Rf and Rg each represent a hydrogen atom or a substituent; Rc, Rd and Re do not form any ring by mutual bounding.

$A_0$ represents an aromatic hydrocarbon ring group or an aromatic heterocyclic group.

$B_1$ to $B_5$ each represent, a carbon atom, $CR_0$, a nitrogen atom, an oxygen atom or a sulfur atom, provided that at least one of $B_1$ to $B_5$ represents a nitrogen atom; $R_0$ represents a hydrogen atom or a substituent.

$X_1$-$L_1$-$X_2$ represents a bidentate ligand; $X_1$ and $X_2$ each independently represent a carbon atom, a nitrogen atom or an oxygen atom; $L_1$ represents an atomic group that forms a bidentate ligand with $X_1$ and $X_2$; n represents an integer of 1 to 3; m represents an integer of (3-n); and M represents a transition metal element in Groups VIII to X of the periodic table.)

11. The organic electroluminescent element of any one of aspects 4 to 10, in which the ring formed by $B_1$ to $B_5$ is an imidazole ring or a pyrazole ring.

12. The organic electroluminescent element of any one of aspects 1 to 11, in which the emissive layer is a layer formed by using a coating liquid containing the compound A.

13. The organic electroluminescent element of any one of aspects 1 to 12, in which the emissive layer emits white light.

14. A lighting device including the organic electroluminescent element of any one of aspects 1 to 13.

15. A display device including the organic electroluminescent element of any one of aspects 1 to 13.

Advantageous Effects of Invention

These means or aspects according to the present invention described above can provide an organic electroluminescent element that has low drive voltage, high emission efficiency, high durability and an excellent effect of preventing dark spots from forming. Also, they can provide a lighting device and a display device each including the organic electroluminescent element.

EMBODIMENTS TO CARRYOUT THE INVENTION

Figure 1:
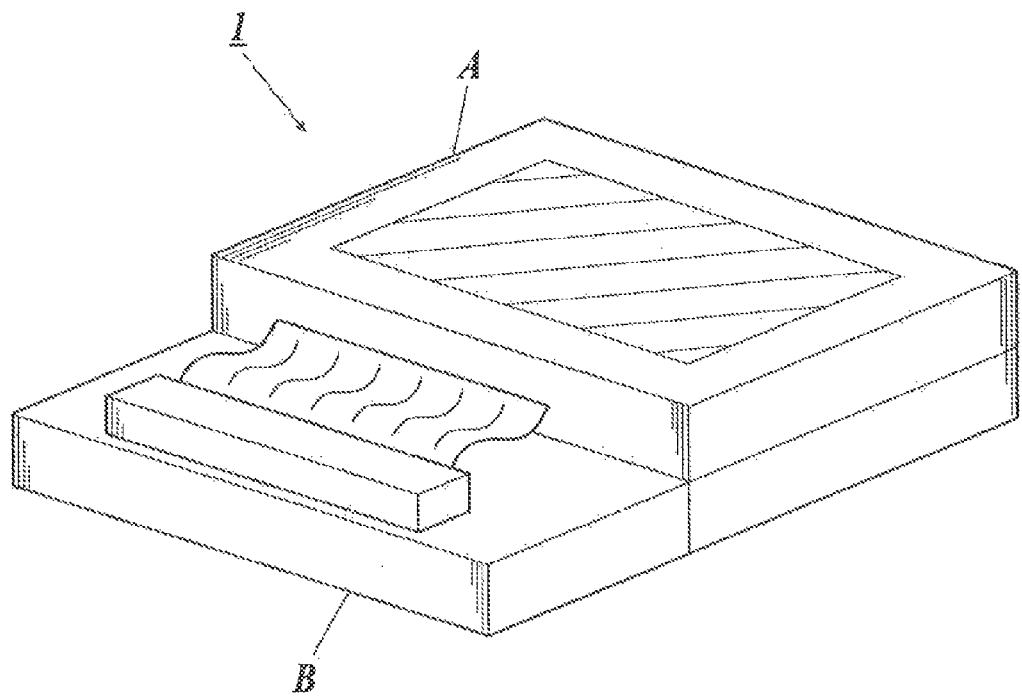
FIG. 1 is a schematic view showing an exemplary display device including an organic EL element.

An organic electroluminescent element (hereinafter, referred to as an organic EL element) according to the present invention includes an anode, a cathode, and an emissive layer. The organic electroluminescent element includes a layer containing a compound A, the compound A is characterized in that a difference between the maximum emission wavelength on the shortest wavelength side in an emission spectrum measured at 300 K and the maximum emission wavelength on the shortest wavelength side in an emission spectrum measured at 77 K is 0 nm or more and 5 nm or less.

According to the present invention, the layer containing the compound A can provide an organic EL element that has low drive voltage, nigh emission efficiency, long endurance and an excellent effect of preventing dark spots from forming.

The reason why the compound A according to the present invention, brings about the above advantageous effects of the present invention is not clear, but may be presumed as follows.

As to one of disadvantages with conventional metal complexes, the inventors have assumed that significant change in the molecular structure of a phosphorescent compound between the ground state (S0) and the excited triplet state (T1) at the time of emission of light induces increased non-radiative deactivation, resulting in failure for obtaining an organic EL element having long lifetime of the element and high emission efficiency to ensure practical use, and thus the inventors have diligently studied the disadvantageous phenomenon.

As a result, the present inventors have found that incorporation of a metal complex, which was a compound A, has improved lifetime of the element and increased emission efficiency.

It has been found that a phosphorescent compound represented by a metal complex has often a ligand composed of two different rings, and if an aromatic hydrocarbon ring group or an aromatic heterocyclic group is attached as a substituent to a ring of the ligand (for example, $A_0$ as a substituent on the Ring B in the drawing below), then an angle of rotation (φ1) at the junction of the ring and the substituent becomes the largest structural change portion between S0 and T1. It has also been found that this structural change is reflected in a difference in the 0-0 transition band between the emission spectra measured at 77 K and 300 K.

An appropriate sterically bulky substituent on the other ring (for example, $P_1$ as a substituent on the Ring A in the drawing below) inhibits changes in the angle of rotation associated with excitation, resulting in a rigid molecular structure and decreasing of the value of knr. This is assumed to bring about the advantageous effects of the present invention.

However, too bulky $P_1$ leads to larger φ2. This makes it difficult to form a complex, and even if formed, the resulting complex is unstable.

It has been found that when a substituent $P_1$ forms a ring (the dotted line connecting the Ring A with $P_1$ in the drawing below) enhances its effect. It is presumed that an organic EL element using a compound having a difference of 0 nm or more and 5 nm or less in the 0-0 transition band between the emission spectra measured at 77 K and 300 K has a very small, structural change between S0 and T1, and can exhibit the advantageous effects of the present invention. It is presumed that a compound having a difference above 5 nm has a higher knr along with a larger structural change, leading to a decrease in efficiency and stability.

[Chem. 8]

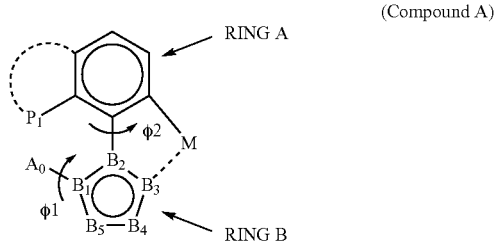

(Compound A)

The compound A has a difference of 0 nm or more and 5 nm or less between the maximum, emission wavelength on the shortest, wavelength side in a emission spectrum measured at 300 K and the maximum, emission wavelength on the shortest wavelength side in a emission spectrum measured, at 77 K.

The maximum emission wavelength as used herein corresponds to a peat wavelength in the emission band assigned to the 0-0 transition (also known as the 0-0 transition band) in an emission spectrum. The 0-0 transition band is a maximum emission wavelength that appears on the shortest wavelength side in an emission spectrum chart, and determined by the following measurement method.

(Measurement Method of 0-0 Transition Band in Emission Spectrum)

A compound to be measured is dissolved in 2-methyltetrahydrofuran that is thoroughly deoxygenated by nitrogen bubbling or the like, and the solution is loaded into a measuring cell, followed by irradiation with excitation light at a liquid nitrogen temperature of 77 K so as to measure an emission spectrum after irradiation of the excitation light.

For any compound that cannot dissolve in such a solvent, any other solvents may be used to dissolve it (substantially, the solvent effect on the emission wavelength is negligibly slight in the measurement method).

The determination of the 0-0 transition band will be described. The 0-0 transition band in the present invention is defined by a maximum emission wavelength that appears on the shortest wavelength side in the phosphorescence spectrum obtained by the measurement described above.

The emission spectrum of the solution prepared above is similarly measured at 300 K to determine another 0-0 transition band. The difference between the 0-0 transition bands at 300 K and 77 K is then calculated.

Typical examples of the compound A having such a difference between the 0-0 transition bands include compounds represented by Formula (1).

(Compounds Represented by Formula (1))

The compounds represented by Formula (1) will now be described.

In Formula (1), $C_{10}$ and $C_{11}$ each represent a carbon atom; $A_1$ and $A_2$ each represent a nitrogen atom or CRa; Ra represents a hydrogen atom or a substituent; $P_1$ represents an oxygen atom, a nitrogen atom, or a sulfur atom; $P_2$, $P_3$ and $P_4$ each represent CRb, C(RcRd), a nitrogen atom, NRe, Si(RfRg), an oxygen atom or a sulfur atom; and Rb, Rc, Rd, Re, Rf and Rg each represent a hydrogen atom or a substituent.

In Formula (1), Rb, Rc, Rd, and Re do not form any ring by mutual bounding, $A_0$ represents an aromatic hydrocarbon ring group or an aromatic heterocyclic group; k represents 0 or an integer of 1; $B_1$ to $B_5$ each represent, a carbon atom, $CR_0$, a nitrogen atom, an oxygen atom or a sulfur atom, provided that at least one of $B_1$ to $B_5$ represents a nitrogen atom, and these five atoms form, a five-membered aromatic nitrogen-containing heterocyclic ring. $R_0$ represents a hydrogen atom or a substituent. $X_1$-$L_1$-$X_2$ represents a bidentate ligand, and $X_1$ and $X_2$ each independently represents a carbon atom, a nitrogen atom or an oxygen atom. Each of the bonds between $C_{11}$ and $P_4$, $C_{11}$ and $P_3$, $P_4$ and $P_3$, $P_3$ and $P_2$, $P_2$ and $P_1$, and $P_1$ and $C_{10}$ is a single bond or double bond. $L_1$ represents an atomic group that forms a bidentate ligand with $X_1$ and $X_2$; and M represents a transition metal element in Groups VIII to X of the periodic table.

In Formula (1), when Ra, Rb, Rc, Rd, Re, Rf, Rg, or $R_0$ represents a substituent, the examples of the substituent include alkyl groups such as methyl, ethyl, propyl, isopropyl, tert-butyl, pentyl, hexyl, octyl, dodecyl, tridecyl, tetradecyl, and pentadecyl groups; cycloalkyl groups such as cyclopentyl and cyclohexyl groups; alkenyl groups such as vinyl and allyl groups; alkynyl groups such as ethynyl and propargyl groups); aromatic hydrocarbon ring groups also referred as aromatic hydrocarbon groups, aromatic carbocyclic groups or aryl groups such as phenyl, p-chlorophenyl, mesityl, tolyl, xylyl, naphthyl, anthryl, azulenyl, acenaphthenyl, fluorenyl, phenanthryl, indenyl, pyrenyl, and biphenylyl groups; aromatic heterocyclic groups such as pyridyl, pyrimidinyl, furyl, pyrrolyl, imidazoiyl, benzimidazolyl, pyrazolyl, pyrazinyl, triazolyl (for example, 1,2,4-triazol-1-yl and 1,2,3-triazole-1-yl), oxazolyl, benzoxazolyl, thiazolyl, isoxazolyl, isothiazolyl, furazanyl, thienyl, quinolyl, benzofuryl, dibenzofuryl, benzothienyl, dibenzothienyl, indolyl, carbazolyl, carbolinyl, diazacarbazolyl (a group in which one of the carbon atoms in the carboline ring in the carbolinyl group is replaced by a nitrogen atom), quinoxalinyl, pyridazinyl, triazinyl, quinazolinyl, and phthalazinyl groups; heterocyclic groups such as pyrrolidyl, imidazolidyl, morpholyl, and oxazolidyl groups; alkoxy groups such as methoxy, ethoxy, propyloxy, pentyloxy, hexyloxy, octyloxy, and dodecyloxy groups; cycloalkoxy groups such as cyclopentyloxy and cyclohexyloxy groups; aryloxy groups such as phenoxy and naphthyloxy groups; alkylthio groups, such as methylthio, ethylthio, propylthio, pentylthio, hexylthio, octylthio, and dodecylthio group; cycloalkylthio groups such as cyclopentylthio and cyclohexylthio groups; arylthio groups such as phenylthio and naphthylthio groups; alkoxycarbonyl groups such as methyloxycarbonyl, ethyloxycarbonyl, butyloxycarbonyl, octyloxycarbonyl, and dodecyloxycarbonyl groups; aryloxycarbonyl groups such as phenyloxycarbonyl and naphthyloxycarbonyl groups; sulfamoyl groups such as aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, and 2-pyridylaminosulfonyl groups; acyl groups such as acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, and pyridylcarbonyl groups; acyloxy groups such as acetyloxy, ethylcarbonyloxy, butylcarbonyloxy, octylcarbonyloxy, dodecylcarbonyloxy, and phenylcarbonyloxy groups; amido groups such as methylcarbonylamino, ethylcarbonylamino, dimethylcarbonylamino, propylcarbonylamino, pentylcarbonylamino, cyclohexylcarbonylamino, 2-ethylhexylcarbonylamino, octylcarbonylamino, dodecylcarbonylamino, phenylcarbonylamino, and naphthylcarbonylamino groups; carbamoyl groups such as aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, and 2-pyridylaminocarbonyl groups; ureido groups such as methylureido, ethylureido, pentylureido, cyclohexylureido, octylureido, dodecylureido, phenylureidonaphthylureido, and 2-pyridylaminoureido groups; sulfinyl groups such as methylsulfinyl, ethylsulfinyl, butylsulfinyl, cyclohexylsulfinyl, 2-ethylhexylsulfinyl, dodecylsulfinyl, phenylsulfinyl, naphthylsulfinyl, and 2-pyridylsulfinyl groups; alkylsulfonyl groups such, as methylsulfonyl, ethylsulfonyl, butylsulfonyl, cyclohexylsulfonyl, 2-ethylhexylsulfonyl, and dodecylsulfonyl groups; arylsulfonyl groups or heteroarylsulfonyl groups, such as phenylsulfonyl, naphthylsulfonyl, and 2-pyridylsulfonyl groups; amino groups such as amino, ethylamino, dimethylamino, diphenylamino, butylamino, cyclopentylamino, 2-ethylhexylamino, dodecylamino, anilino, naphthylamino, and 2-pyridylamino groups; halogen atoms such as fluorine, chlorine and bromine atoms; fluorohydrocarbon groups such as fluoromethyl, trifluoromethyl, pentafluoroethyl, and pentafluorophenyl groups; cyano groups, nitro groups, hydroxy groups, mercapto groups, silyl groups such as trimethylsilyl, triisopropylsilyl, triphenylsilyl, and phenyldiethylsilyl groups; and phosphono groups. Preferred are alkyl groups, aromatic hydrocarbon ring groups, aromatic heterocyclic groups, and alkoxy groups.

Moreover, these substituents may be further substituted with above-described substituents.

Preferred examples of the further substituent on the substituents Ra, Rb, Rc, Rd, Re, Rf, Rg, and $R_0$ in Formula (1) include alkyl groups, aromatic hydrocarbon ring groups, aromatic heterocyclic groups, alkoxy groups, and amino groups.

In Formula (1), $A_0$ represents an aromatic hydrocarbon ring group or an aromatic heterocyclic group. Examples of the aromatic hydrocarbon ring group include phenyl, p-chlorophenyl, mesityl, tolyl, xylyl, naphthyl, anthryl, azulenyl, acenaphthenyl, fluorenyl, phenanthryl, indenyl, pyrenyl, and biphenylyl groups. Examples of the aromatic heterocyclic group include pyridyl, pyrimidinyl, furyl, pyrrolyl, imidazoiyl, benzimidazolyl, pyrazolyl, pyrazinyl, triazolyl (for example, 1,2,4-triazole-1-yl and 1,2,3-triazole-1-yl groups), oxazolyl, benzoxazolyl, thiazolyl, isoxazolyl, isothiazolyl, furazanyl, thienyl, quinolyl, benzofuryl, dibenzofuryl, benzothienyl, dibenzothienyl, indolyl, carbazolyl, carbolinyl, diazacarbazolyl (a group in which one of the carbon atoms in the carboline ring in the carbolinyl group is replaced by a nitrogen atom), quinoxalinyl, pyridazinyl, triazinyl, quinazolinyl, and phthalazinyl groups).

$A_0$ preferably has a substituent, and preferred examples of the substituent include alkyl groups, aromatic hydrocarbon ring groups, aromatic heterocyclic groups and alkoxy groups. Preferred are aromatic hydrocarbon ring groups.

In Formula (2), $A_1$ and $A_2$ each represent a nitrogen atom or CRa, and Ra represents a hydrogen atom or a substituent, $D_1$, $D_2$, and $D_3$ each represent CRb or a nitrogen atom, and Rb represents a hydrogen atom or a substituent, $A_0$ represents an aromatic hydrocarbon ring group or an aromatic heterocyclic group. $B_1$ to $B_5$ each represent a carbon atom, $CR_0$, a nitrogen atom, an oxygen atom or a sulfur atom, provided that at least one of $B_1$ to $B_5$ represents a nitrogen atom. $X_1$-$L_1$-$X_2$ represents a bidentate ligand, and $X_1$ and $X_2$ each independently represents a carbon atom, a nitrogen atom or an oxygen atom, $L_1$ represents an atomic group that forms a bidentate ligand with $X_1$ and $X_2$. And M represents a transition metal element in Groups VIII to X of the periodic table.

In Formula (2), when Ra, Rb, or $R_0$ represents a substituent, it has the same meaning as Ra, Rb, or $R_0$ in Formula (1); and a plurality of Rb do not form, any ring by mutual bounding.

In Formula (2), when $A_0$ represents an aromatic hydrocarbon ring group or an aromatic heterocyclic group, it has the same meaning as $A_0$ in Formula (1).

In Formula (3), $A_1$ and $A_2$ each represent a nitrogen atom or CRa, and Ra represents a hydrogen atom or a substituent. $R_{61}$, $R_{62}$ and $R_{63}$ each represent a hydrogen atom or a substituent. $A_0$ represents an aromatic hydrocarbon ring group or an aromatic heterocyclic group; $B_1$ to $B_5$ each represent a carbon atom, $CR_0$, a nitrogen atom, an oxygen atom or a sulfur atom, provided that at least one of $B_1$ to $B_5$ represents a nitrogen atom. $X_1$-$L_1$-$X_2$ represents a bidentate ligand, and $X_1$ and $X_2$ each independently represents a carbon atom, a nitrogen atom or an oxygen atom; and $L_1$ represents an atomic group that forms a bidentate ligand with $X_1$ and $X_2$. And M represents a transition metal element in Groups VIII to X of the periodic table.

In Formula (3), when Ra, $R_{61}$, $R_{62}$, $R_{63}$, or $R_0$ represents a substituent, it has the same meaning as Ra, Rb, Rc, Rd, or $R_0$ in Formula (1).

In Formula (3), when $A_0$ represents an aromatic hydrocarbon ring group or an aromatic heterocyclic group, it has the same meaning as $A_0$ in Formula (1).

In Formula (4), $A_1$ and $A_2$ each represent a nitrogen atom or CRa, and Ra represents a hydrogen atom or a substituent. $Z_0$ represents an oxygen atom or a sulfur atom. $Z_1$, $Z_2$, and $Z_3$ each represent C(RcRd), NRe, Si(RfRg), an oxygen atom or a sulfur atom; and Rc, Rd, Re, Rf, and Rg each represent a hydrogen atom or a substituent. $A_0$ represents an aromatic hydrocarbon ring group or an aromatic heterocyclic group. $B_1$ to $B_5$ each represent a carbon atom, $CR_0$, a nitrogen atom, an oxygen atom or si sulfur atom, provided that at least one of $B_1$ to $B_5$ represents a nitrogen atom, $X_1$-$L_1$-$X_2$ represents a bidentate ligand, and $X_1$ and $X_2$ each independently represents a carbon atom, a nitrogen atom or an oxygen atom; and $L_1$ represents an atomic group that forms a bidentate ligand with $X_1$ and $X_2$. M represents a transition metal element in Groups VIII to X of the periodic table; and $R_{61}$, $R_{62}$ and $R_{63}$ do not form any ring by mutual bounding.

In Formula (4), when Ra, Rc, Rd, Re, Rf, or Rg represents a substituent, it has the same meaning as Ra, Rb, Rc, Rd, or $R_0$ in Formula (1).

In Formula (4), when $A_0$ represents an aromatic hydrocarbon ring group or an aromatic heterocyclic group, it has the same meaning as $A_0$ in Formula (1); and Rc, Rd, and Re do not form any ring by mutual bounding.

In Formula (5), $A_1$ and $A_2$ each represent a nitrogen atom or CRa, and Ra represents a hydrogen atom or a substituent, $Y_1$ represents an oxygen atom, a sulfur atom, C(RcRd), NRe or Si(RfRg); and Rc, Rd, Re, Rf, and Rg each represent a hydrogen atom or a substituent, $R_{71}$ represents a hydrogen atom or a substituent; $A_0$ represents an aromatic hydrocarbon ring group or an aromatic heterocyclic group; $B_1$ to $B_5$ each represent a carbon atom, $CR_0$, a nitrogen atom, an oxygen atom or a sulfur atom, provided that at least one of $B_1$ to $B_5$ represents a nitrogen atom. $X_1$-$L_1$-$X_2$ represents a bidentate ligand, and $X_1$ and $X_2$ each independently represents a carbon atom, a nitrogen atom or an oxygen atom; and $L_1$ represents an atomic group that forms a bidentate ligand with $X_1$ and $X_2$. M represents a transition metal element in Groups VIII to X of the periodic table.

In Formula (5), when Ra, Rc, Rd, Re, Rf, or Rg represents a substituent, it has the same meaning as Ra, Rb, Rc, Rd, or $R_0$ in Formula (1).

In Formula (5), when $A_0$ represents an aromatic hydrocarbon ring group or an aromatic heterocyclic group, it has the same meaning as $A_0$ in Formula (1); and $R_{71}$, Rc, and Rd do not form any ring by mutual bounding.

In Formula (6), $A_1$ and $A_2$ each represent a nitrogen atom, or CRa, and Ra represents a hydrogen atom or a substituent, $Y_2$ represents a nitrogen atom or CRb, and Rb represents a hydrogen atom or a substituent. $Y_3$ represents an oxygen atom or a sulfur atom; $R_{81}$ represents a hydrogen atom or a substituent; and $A_0$ represents an aromatic hydrocarbon ring group or an aromatic heterocyclic group.

$B_1$ to $B_5$ each represent a carbon atom, $CR_0$, a nitrogen atom, an oxygen atom or a sulfur atom, provided that at least one of $B_1$ to $B_5$ represents a nitrogen atom, $X_1$-$L_1$-$X_2$ represents a bidentate ligand, and $X_1$ and $X_2$ each independently represent a carbon atom, a nitrogen atom or an oxygen atom; $L_1$ represents an atomic group that forms a bidentate ligand with $X_1$ and $X_2$; and M represents a transition metal element in Groups VIII to X of the periodic table.

In Formula (6), when Ra, Rb, or $R_{81}$ represents a substituent, it has the same meaning as Ra, Rb, Rc, Rd, or $R_0$ in Formula (1); and $R_{81}$ and Rb do not form any ring by mutual bounding.

In Formula (6), when $A_0$ represents an aromatic hydrocarbon ring group or an aromatic heterocyclic group, it has the same meaning as $A_0$ in Formula (1).

In Formula (7), $A_1$ and $A_2$ each represent a nitrogen atom or CRa, and Ra represents a hydrogen atom or a substituents $Y_4$ represents an oxygen atom or a sulfur atom; and $Y_5$ and $Y_6$ each represent C(RcRd), NRe, Si(RfRg), an oxygen atom or a sulfur atom, Rc, Rd, Re, Rf, and Rg each represent a hydrogen atom or a substituent; $A_0$ represents an aromatic hydrocarbon ring group or an aromatic heterocyclic group; and $B_1$ to $B_5$ each represent a carbon atom, $CR_0$, a nitrogen atom, an oxygen atom or a sulfur atom, provided that at least one of $B_1$ to $B_5$ represents a nitrogen atom.

$X_1$-$L_1$-$X_2$ represents a bidentate ligand, and $X_1$ and $X_2$ each independently represent a carbon atom, a nitrogen atom or an oxygen atom. $L_1$ represents an atomic group that forms a bidentate ligand with $X_1$ and $X_2$; and M represents a transition metal element in Groups VIII to X of the periodic table.

In Formula (7), when Ra, Rc, Rd, Re, Rf, or Rg represents a substituent, it has the same meaning as Ra, Rb, Rc, Rd, and $R_0$ in Formula (1). Rc, Rd, and Re do not form any ring by mutual bounding.

In Formula (7), when $A_0$ represents an aromatic hydrocarbon ring group or an aromatic heterocyclic group, it has the same meaning as $A_0$ in Formula (1).

Compounds represented by Formulae (2) to (7) can preferably be used among other compounds represented by Formula (1).

In the present invention, preferred are compounds represented by Formulae (4) to (7), and most preferred are compounds represented by Formulae (4) and (7).

In Formulae (1) to (7), n represents an integer of 1 to 3; and m represents an integer of (3-n). In the present invention, a preferred case is n=3 and m=0.

In Formulae (1) to (7), a ring formed by $B_1$ to $B_5$ is preferably an imidazole ring or a pyrazole ring, and most preferably an imidazole ring.

M represents a transition metal element in Groups VIII to X of the periodic table, and preferred is iridium.

Specific examples of a bidentate ligand represented by $X_1$-$L_1$-$X_2$ in the structure represented by any one of Formulae (1) to (7) according to the present invention include substituted or unsubstituted phenylpyridine, phenylpyrazole, phenylimidazole, phenyltriazole, phenyltetrazole, pyrazabole, acetylacetone, and picolinic acid.

The compound A may be exemplified below, but not limited to:

[Chem. 9]

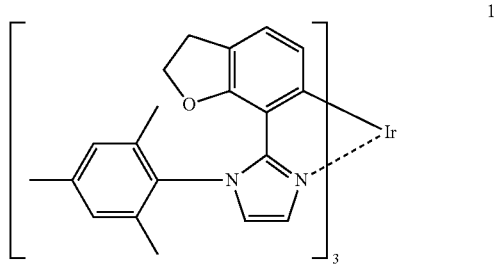

1

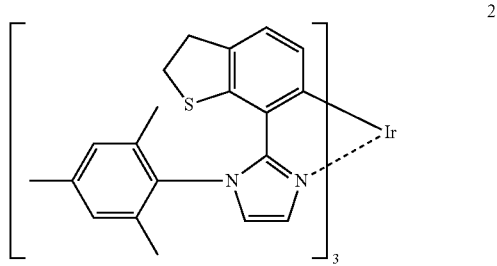

2

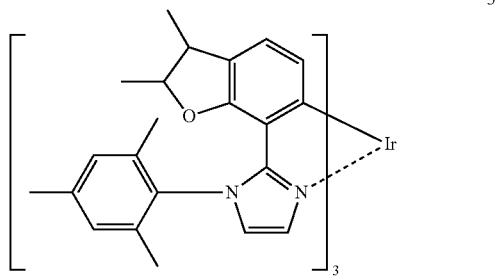

3

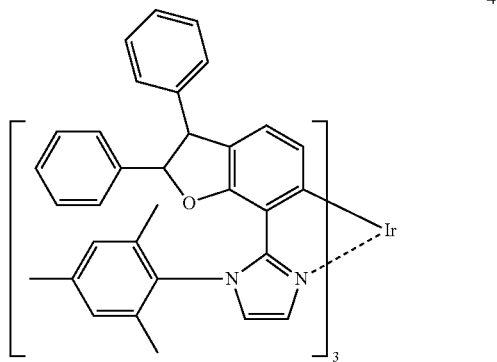

4

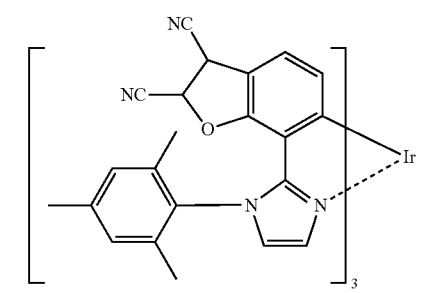
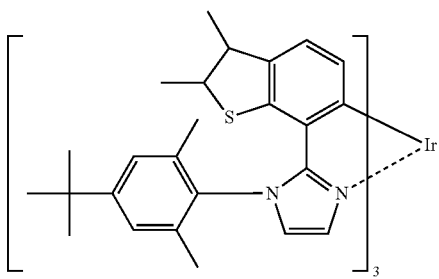
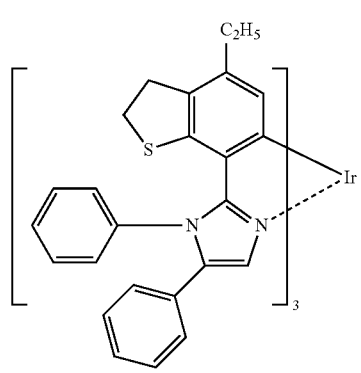
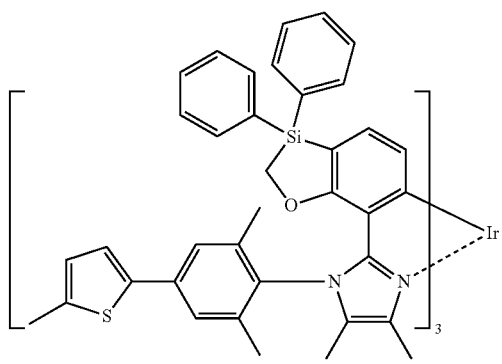
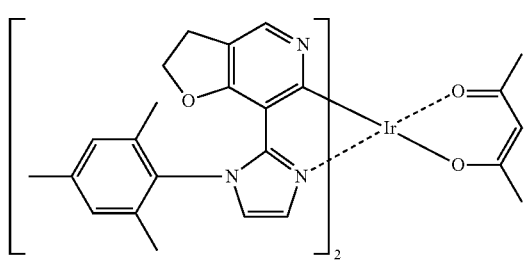
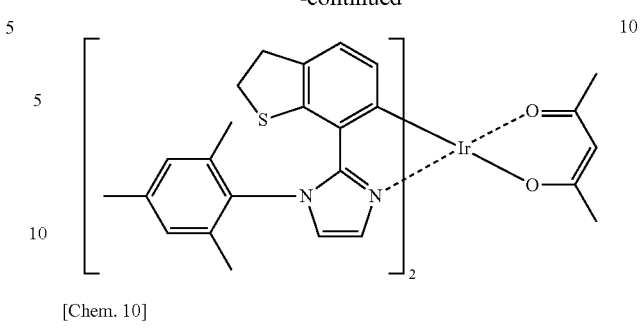
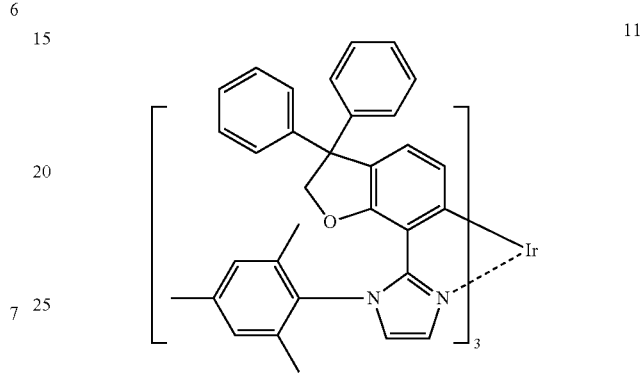
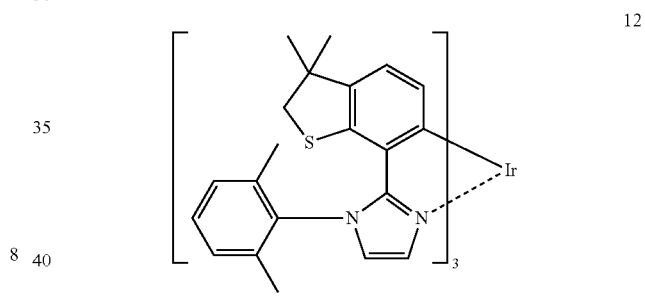
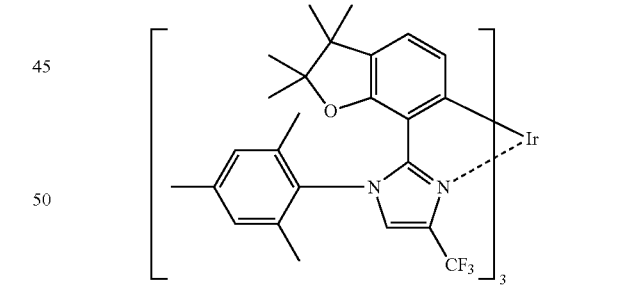
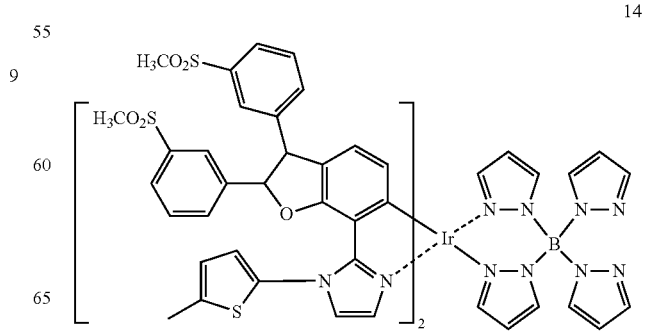

15
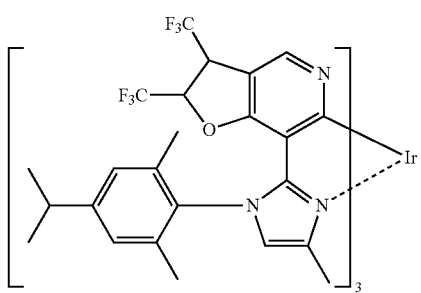
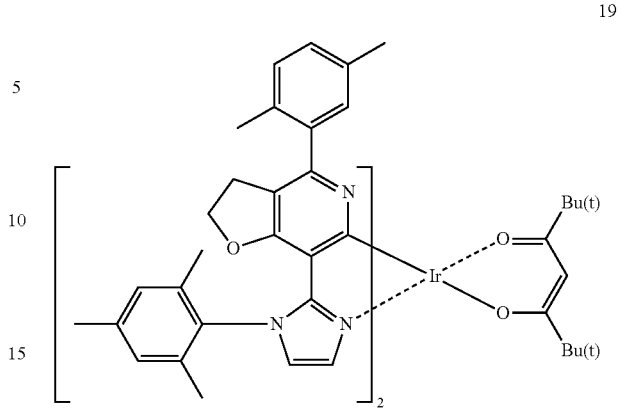
16
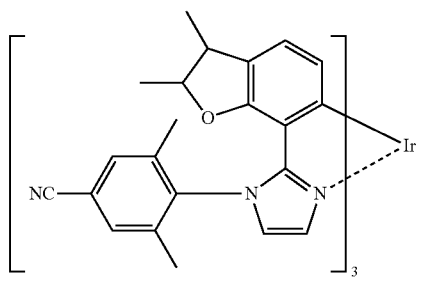
19
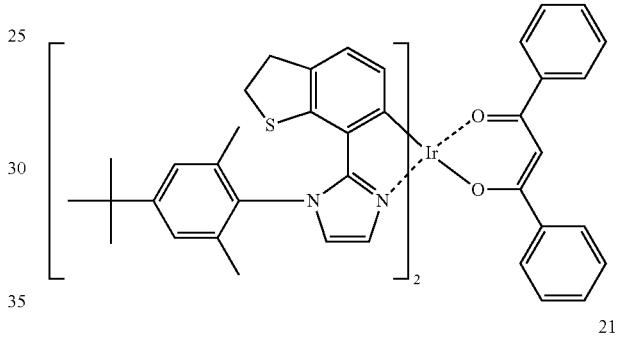
20
17
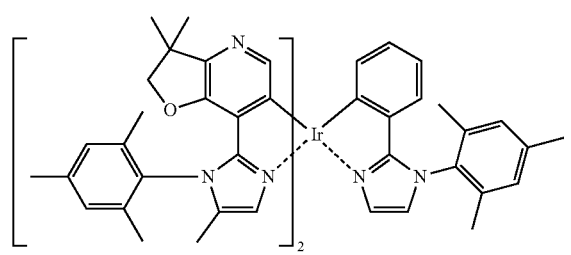
[Chem. 11]
21
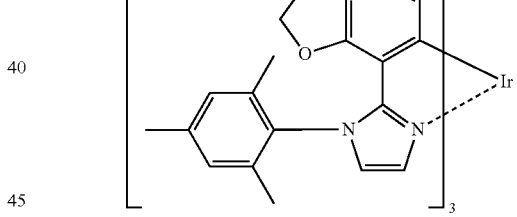
18
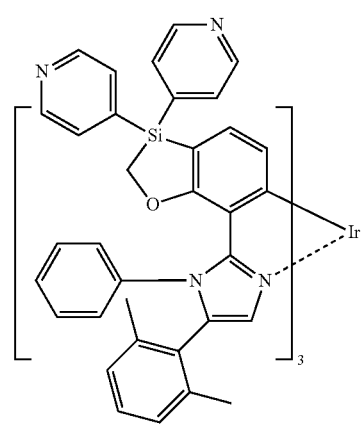
22
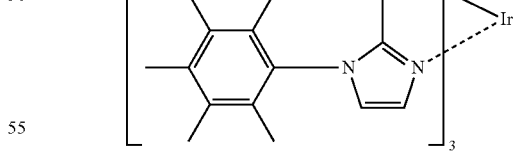
23
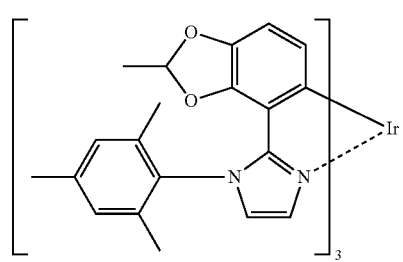

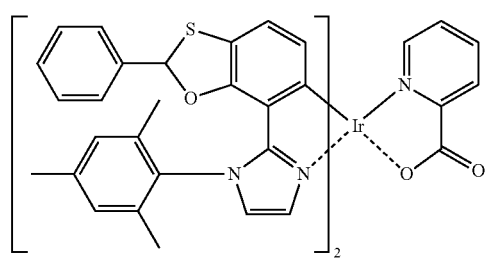
24
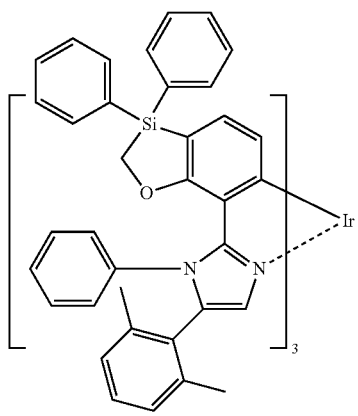
28
[Chem. 12]
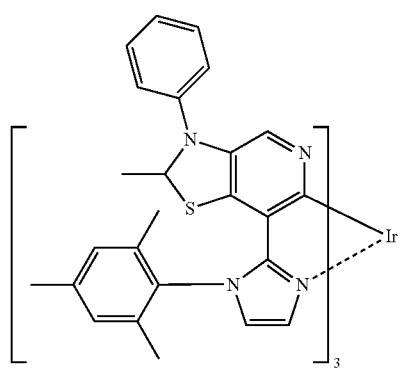
25
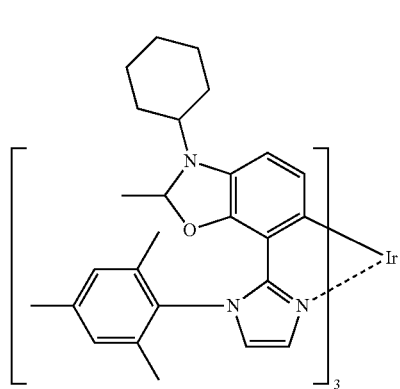
26
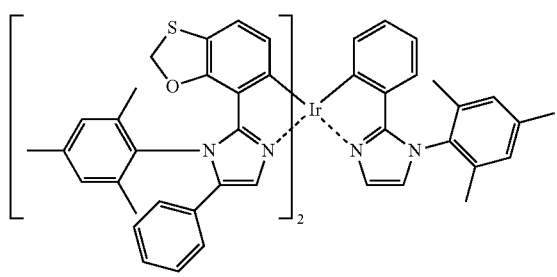
27
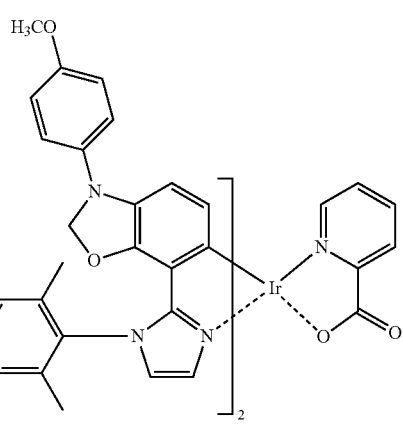
29
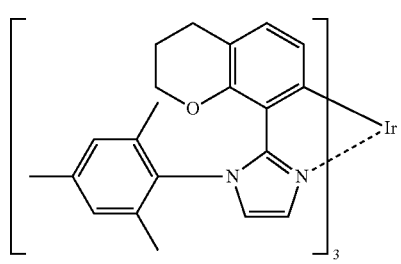
30
[Chem. 13]
31

-continued
32
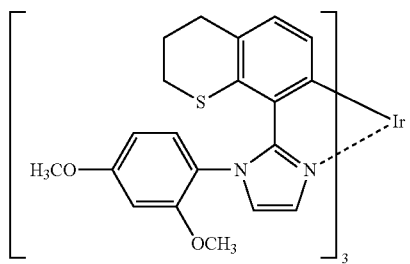
33
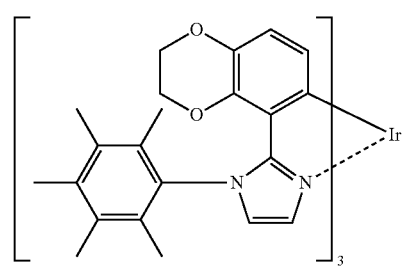
34
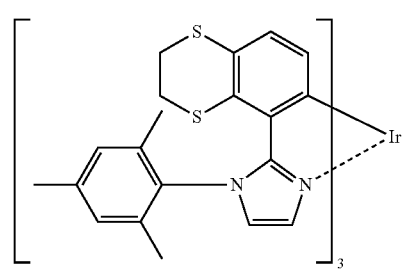
35
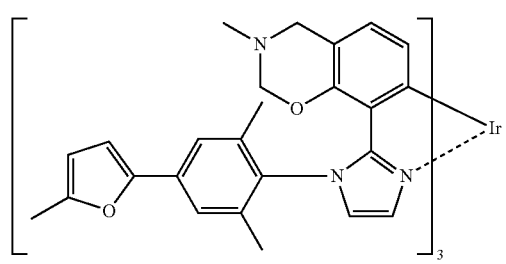
36
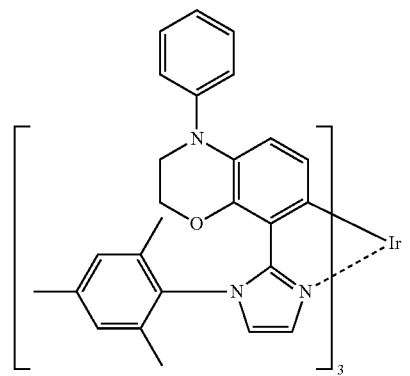
-continued
37
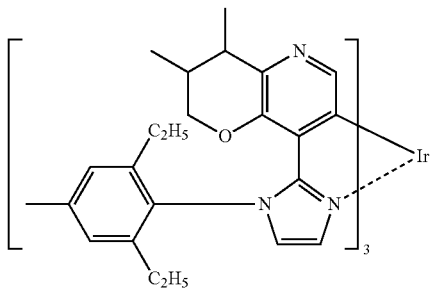
38
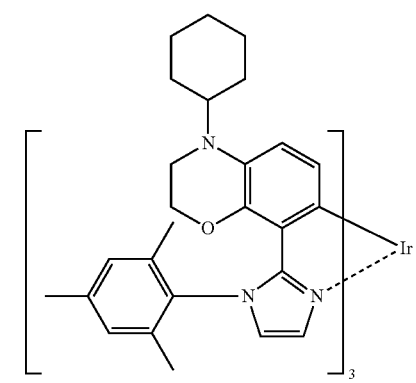
39
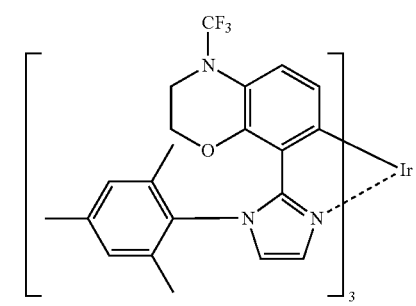
40
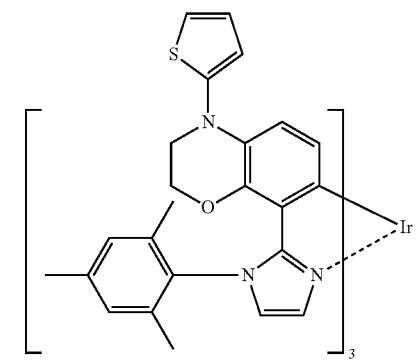
[Chem. 14]
41
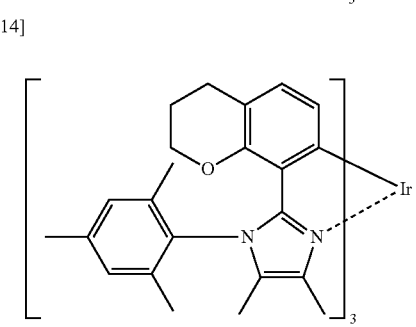

-continued
42
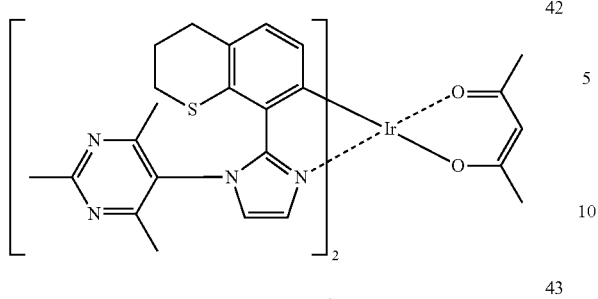
43
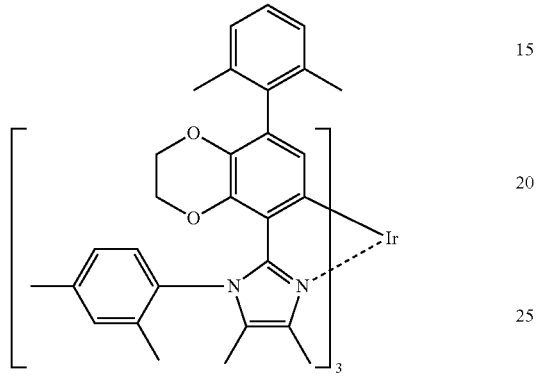
44
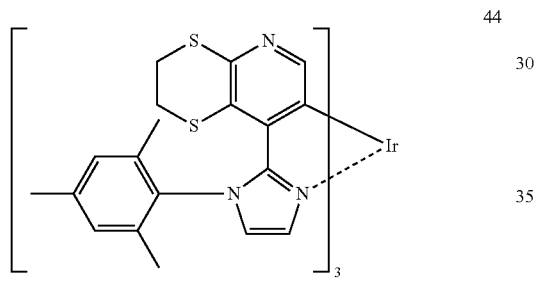
45
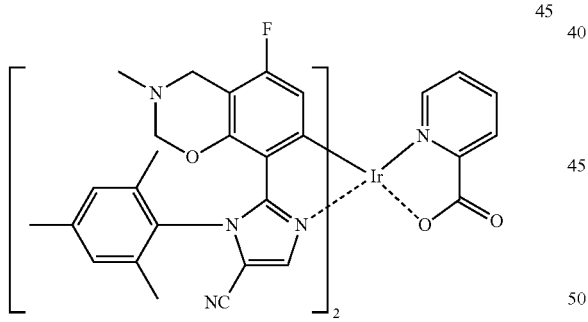
46
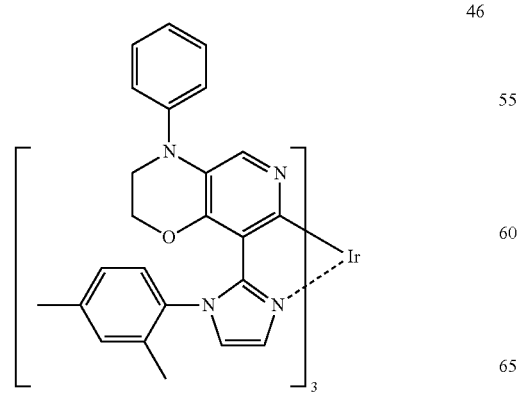
-continued
47
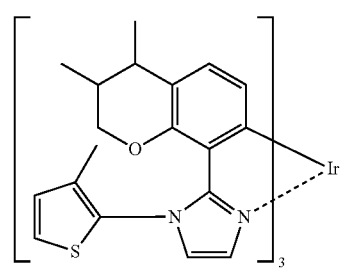
48
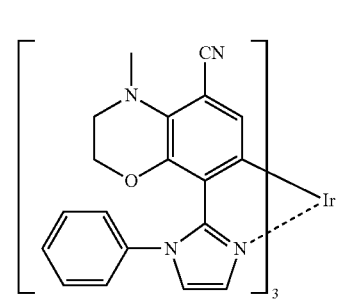
49
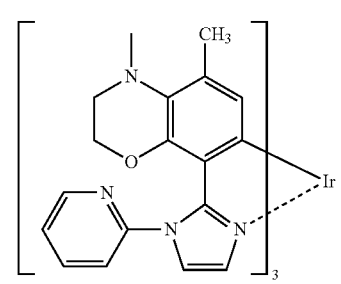
50
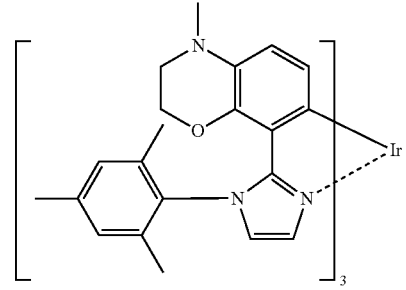
[Chem. 15]
51
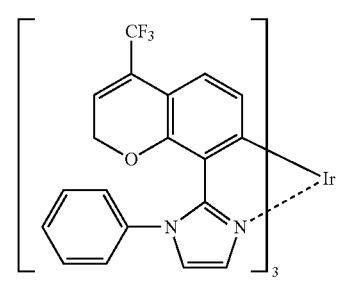

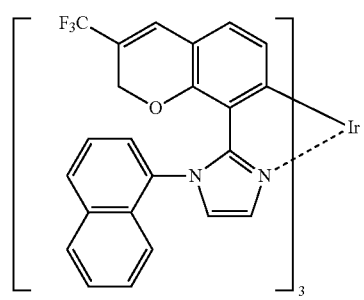
52
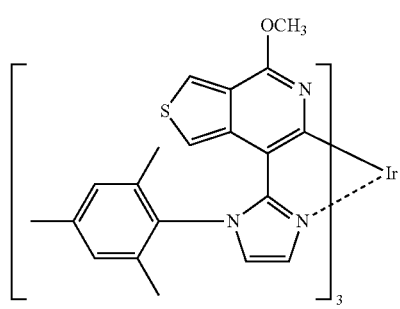
53
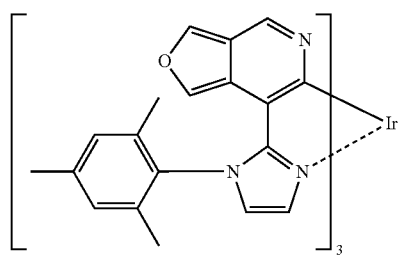
54
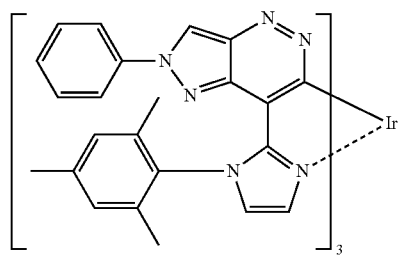
55
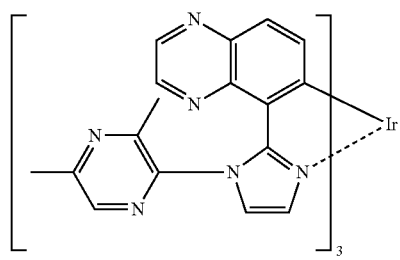
56
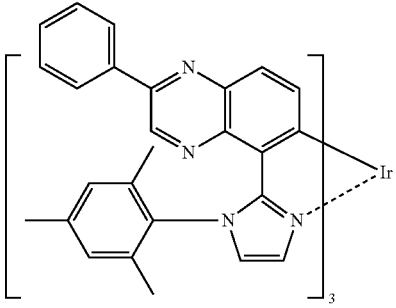
57
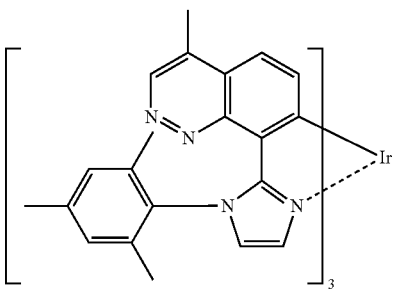
58
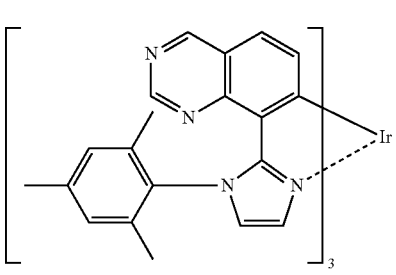
59
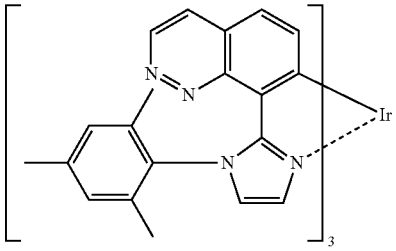
60
[Chem. 16]
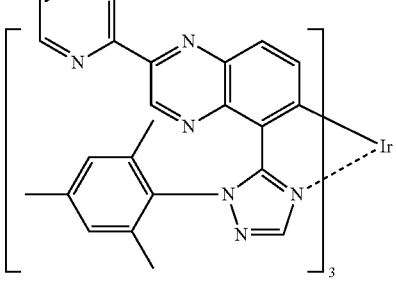
61

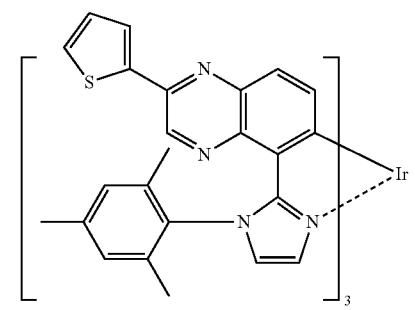
62
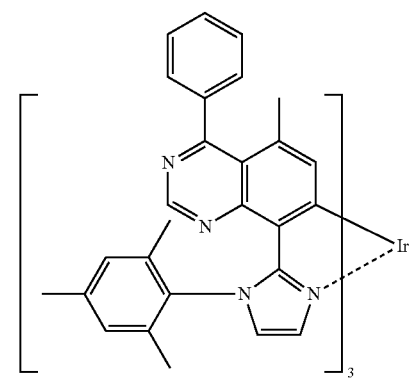
63
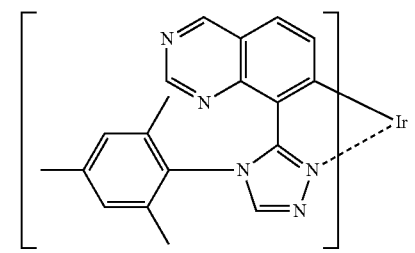
64
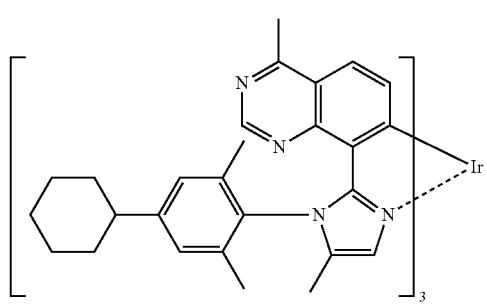
65
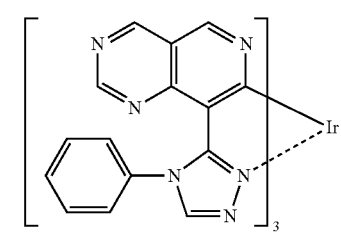
66
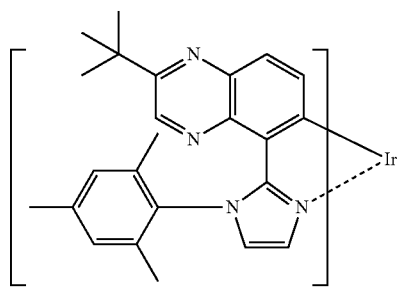
67
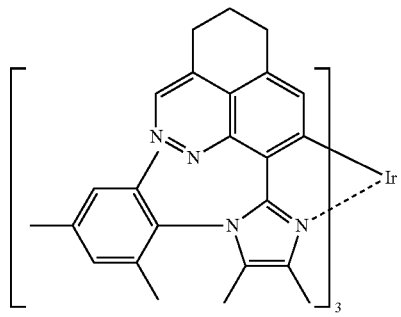
68
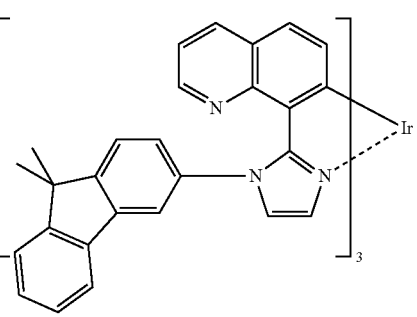
69
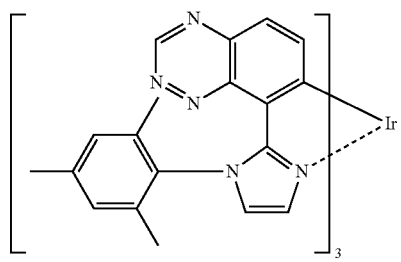
70
[Chem. 17]
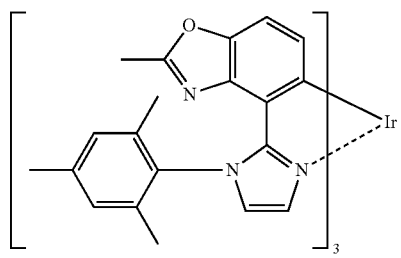
71

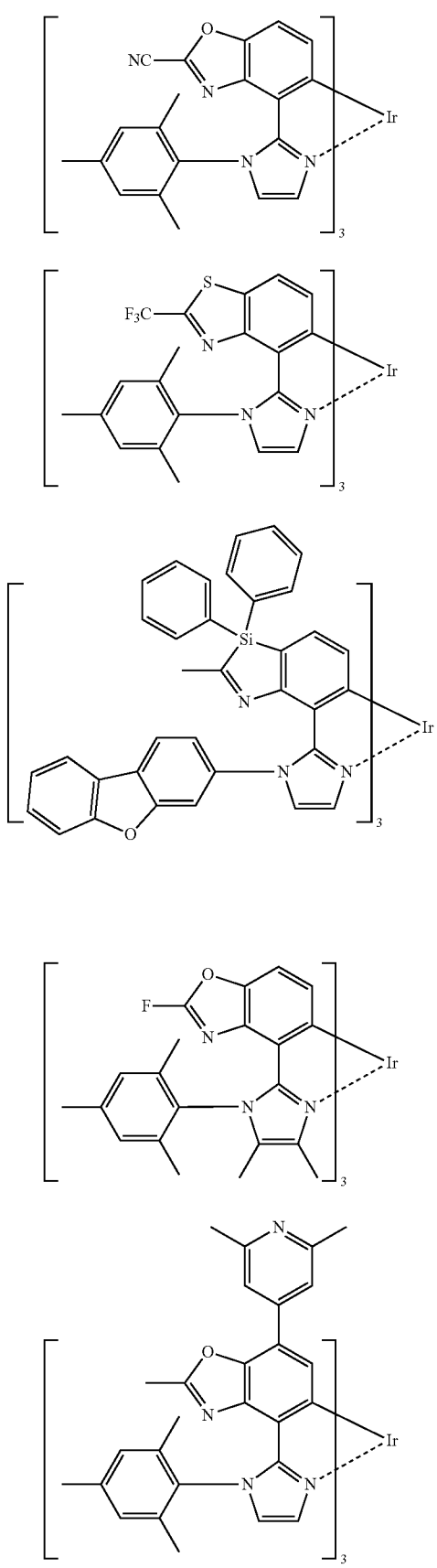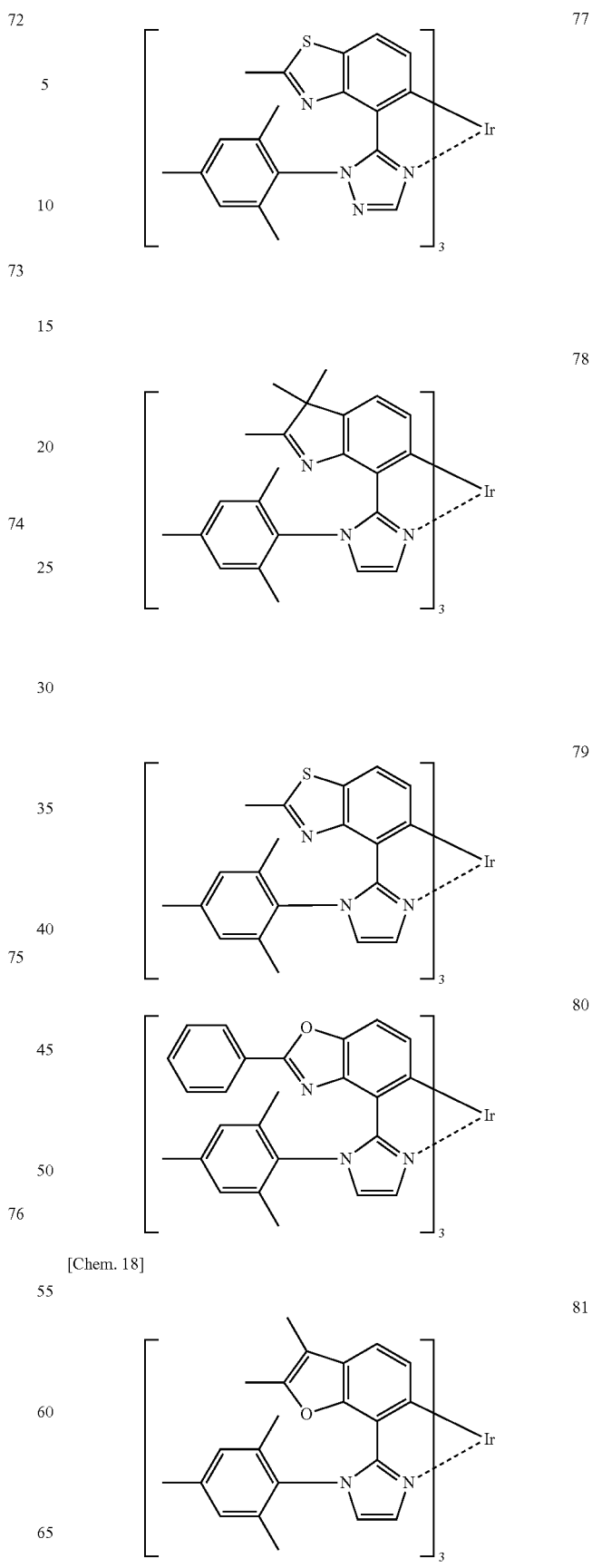

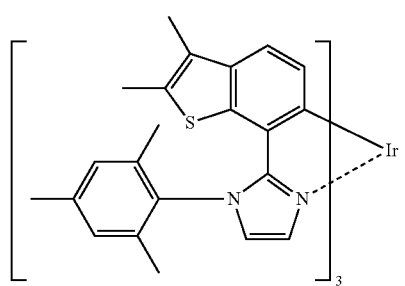
82
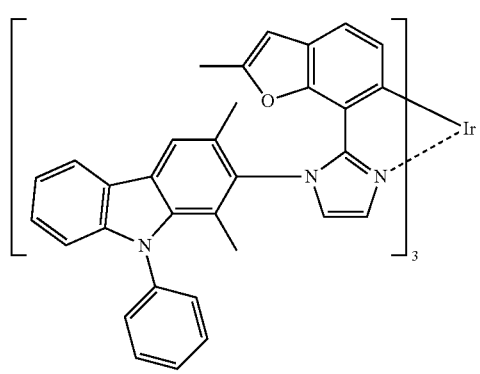
83
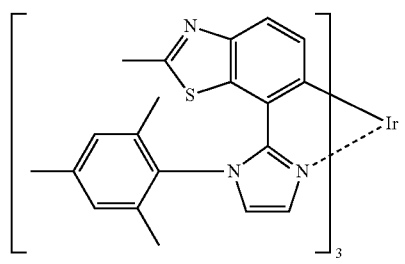
84
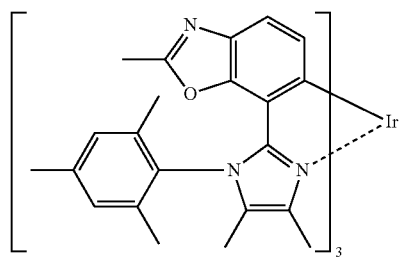
85
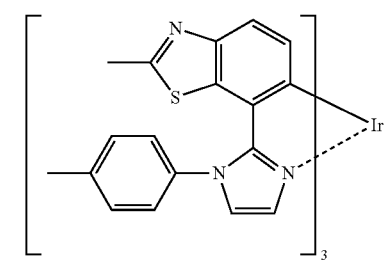
86
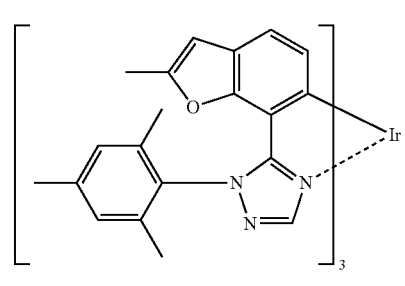
87
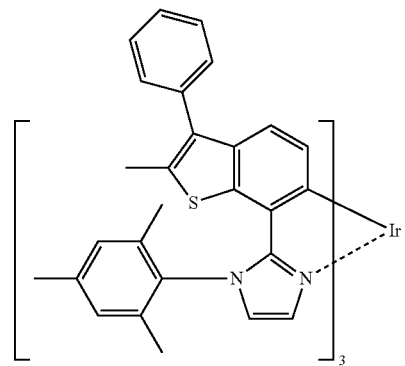
88
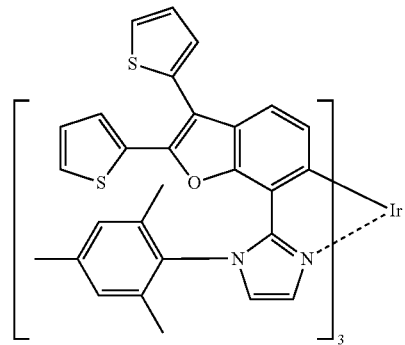
89
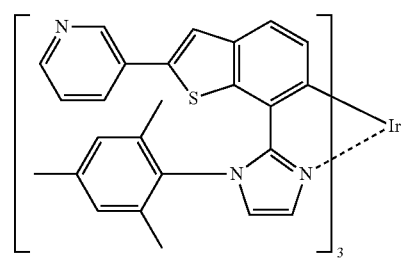
90
[Chem. 19]
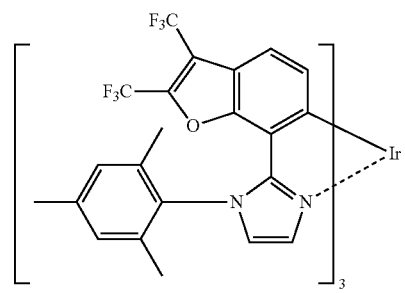
91

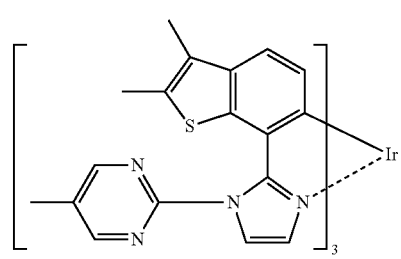 92
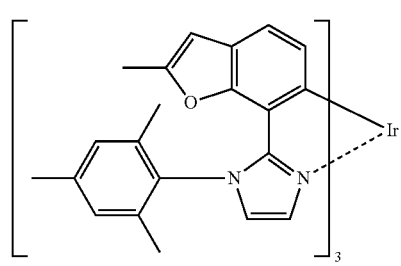 93
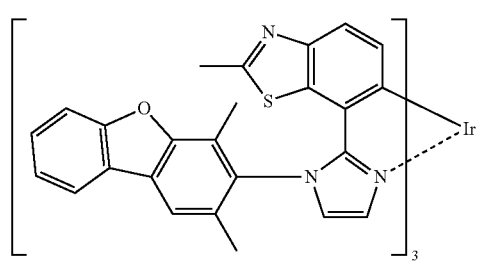 94
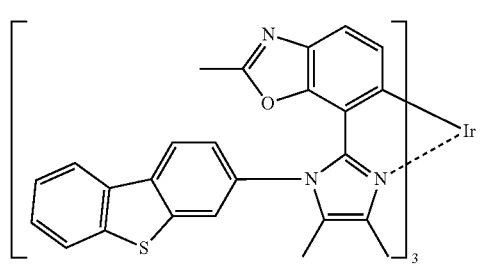 95
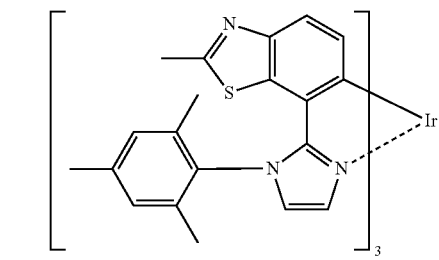 96
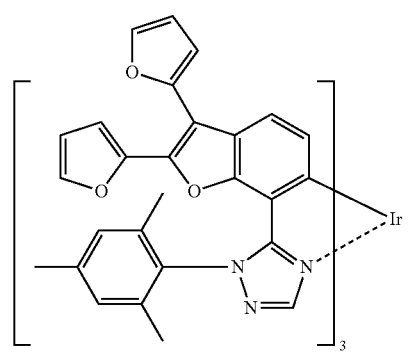 97
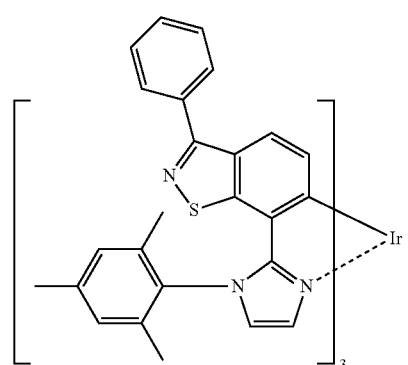 98
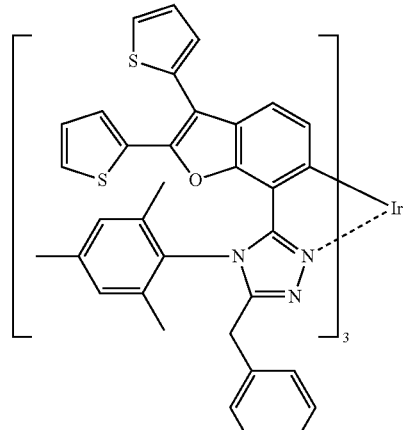 99
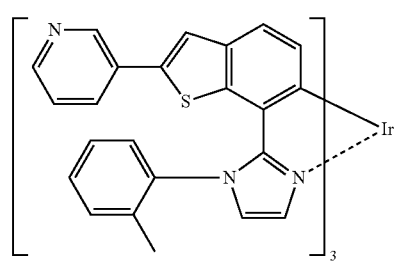 100

[Chem. 20]
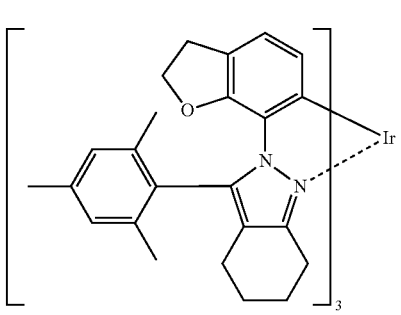
101
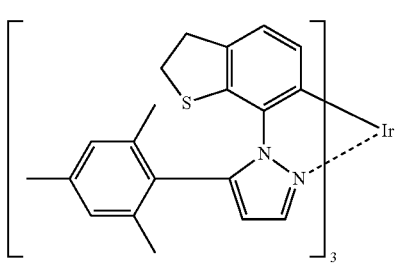
102
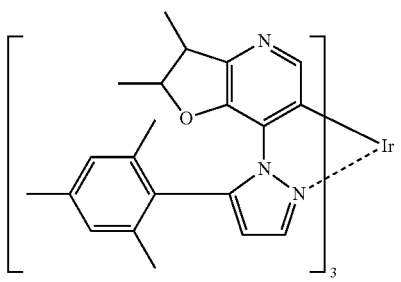
103
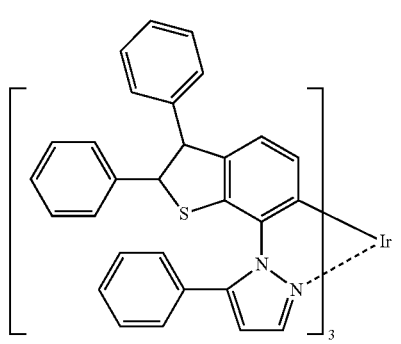
104
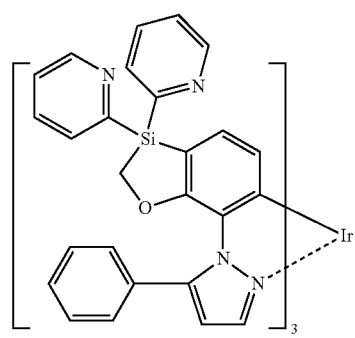
105
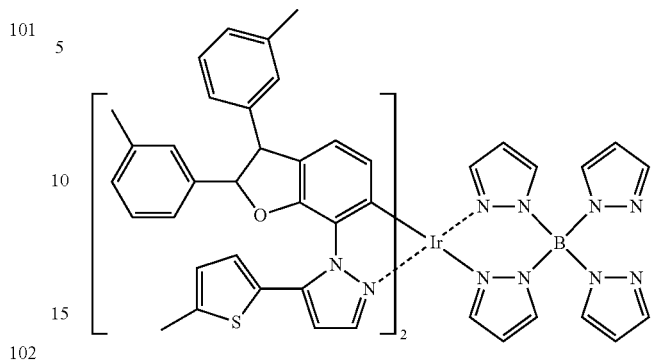
106
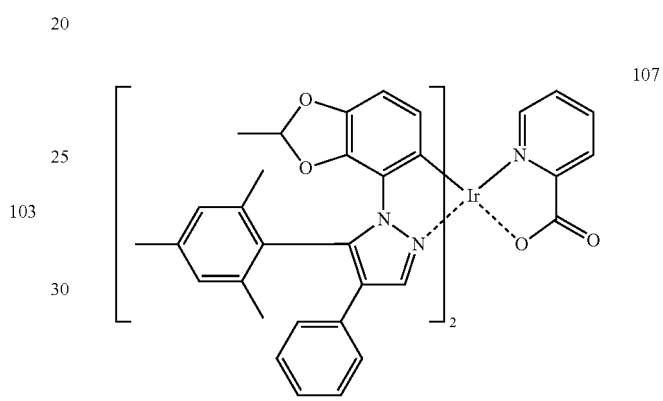
107
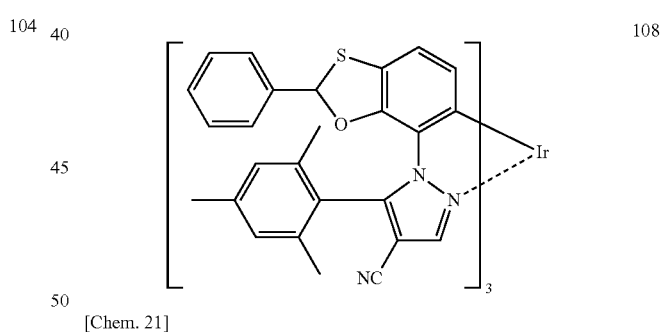
108
[Chem. 21]
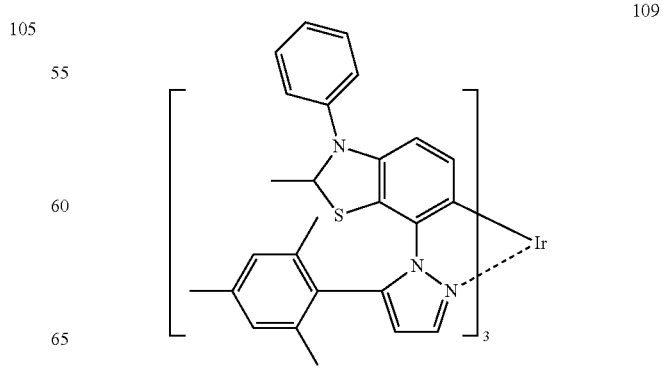
109

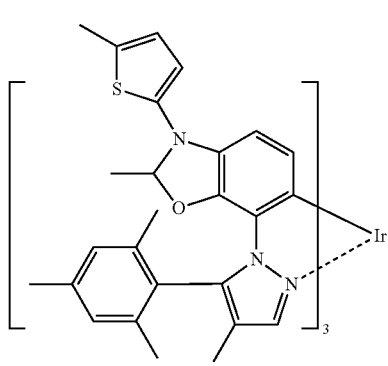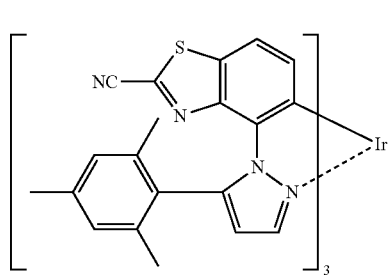

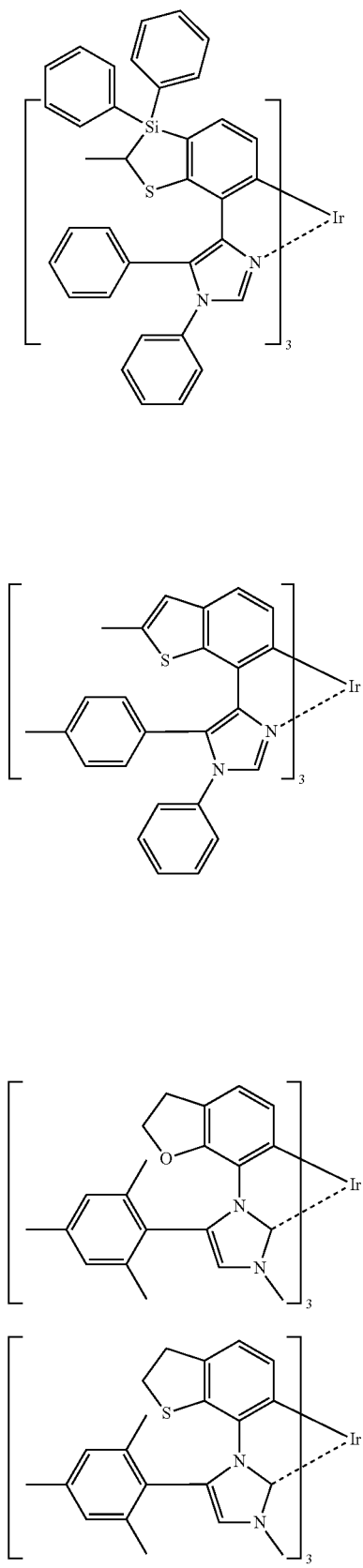
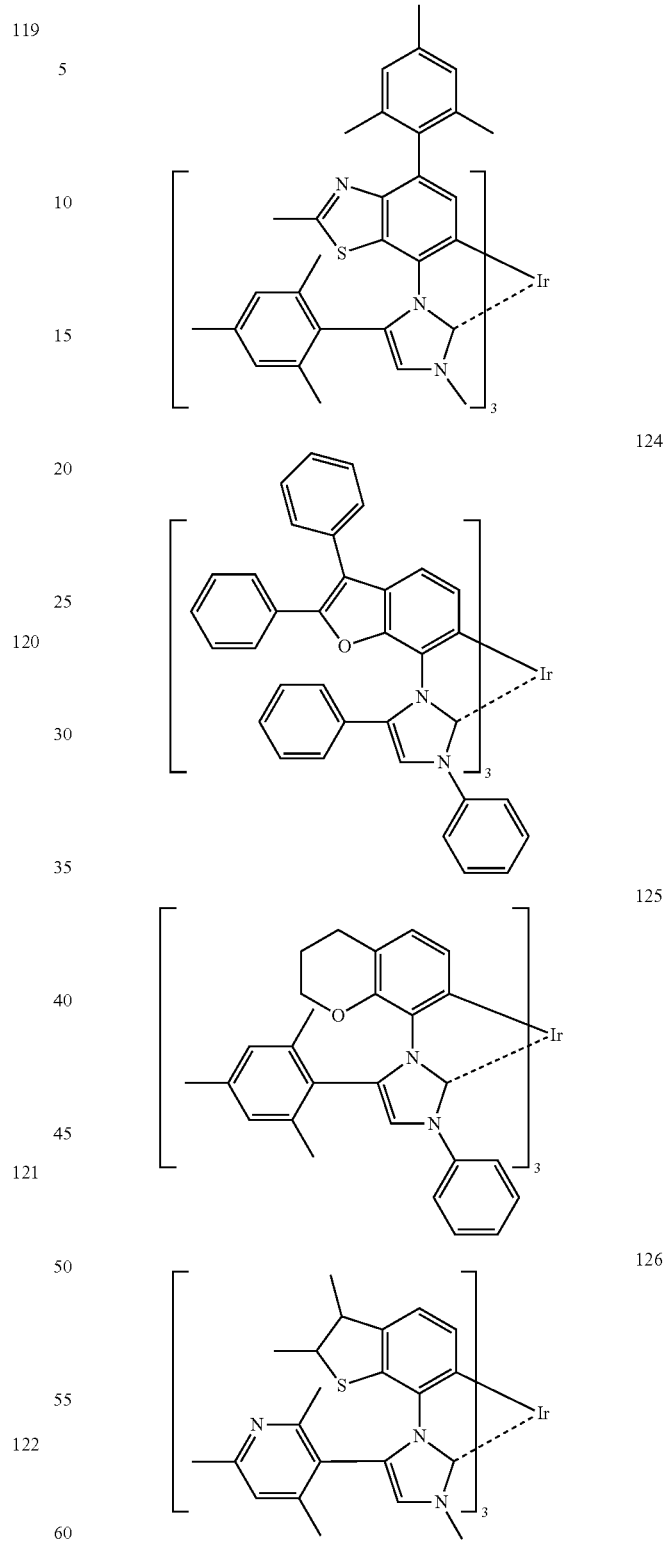
Preparation of the compounds represented by Formula (1) will be described referring to preparations of the compounds represented by Formulae (2) to (7) which are specific compounds for compounds represented by Formula (1) by way of example.

(Preparation of Exemplary Compound 1)

An exemplary compound 1 (corresponding to Formula (7)) was prepared by the following process.

[Chem. 23]

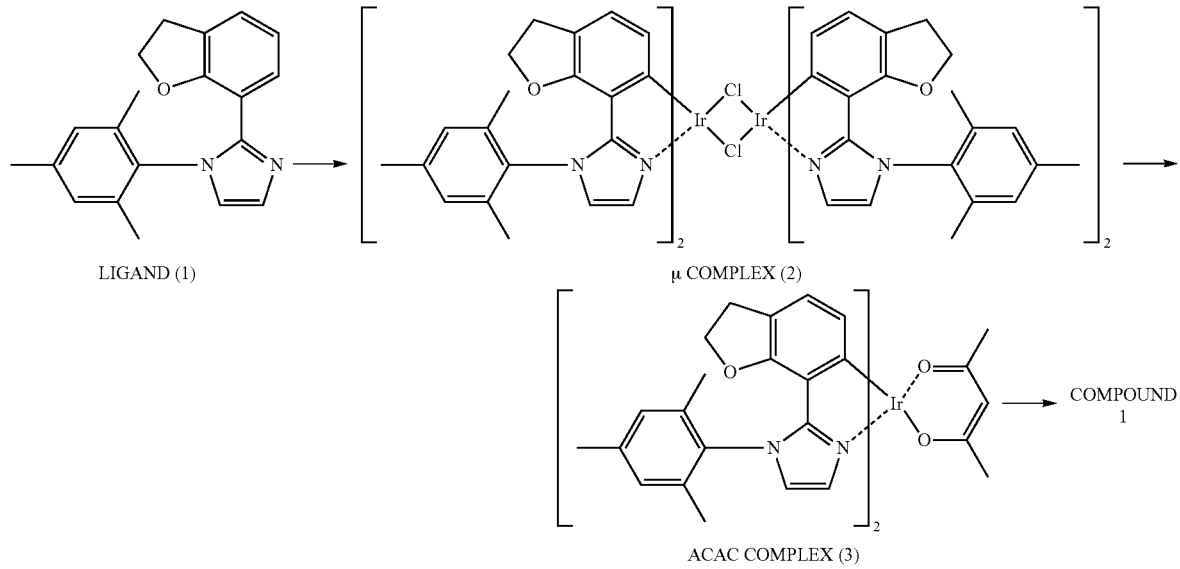

LIGAND (1)

µ COMPLEX (2)

ACAC COMPLEX (3)

→ COMPOUND 1

(Preparation of µ-Complex)

A 100 ml-four-necked flask was charged with 0.7 g of a ligand (1), 7.5 ml of 2-ethoxy ethanol, and 2.5 ml of water, was equipped with a nitrogen inlet tube, a thermometer, and a condenser and placed in an oil bath with a stirrer.

To the mixture, added was 0.3 g of $IrCl_3 \cdot 3H_2O$. The mixture was then boiled and refluxed at an inner temperature of about 100° C. for 5 hours to complete the reaction.

After completion of the reaction, the reaction mixture was cooled to room temperature, and was filtered. The residue was thoroughly washed with methanol and dried to yield 0.5 g of a µ-complex (2).

Step 5: Preparation of acac Complex (3)

A 50 ml-four-necked flask was charged with 0.5 g of the µ-complex (2), 0.1 g of acetylacetone, 0.1 g of sodium carbonate, and 20 ml of 2-ethoxy ethanol, was equipped with a nitrogen inlet tube, a thermometer, and a condenser, and placed in an oil bath with a stirrer.

The reaction was carried out in a stream of nitrogen at an inner temperature of about 90° C. for 2 hours.

After completion of the reaction, the reaction mixture was cooled to room temperature. The resulting crystals were then filtered out, were washed with water (30 ml) and MeOH (10 ml), and were dried to yield 0.4 g of an acac complex (3).

A 50 ml-four-necked flask was charged with 0.4 g of the acac complex (3), 0.2 g of a ligand (1), and 20 ml of glycerin, was equipped with a nitrogen inlet tube, a thermometer, and an air condenser, and was placed in an oil bath with a stirrer. The reaction was carried out in a stream of nitrogen at an inner temperature of around 170° C. for 10 hours to complete the reaction.

After completion of the reaction, the reaction mixture was cooled to room temperature, and the resulting crystals were filtered out.

The crystals were purified by column chromatography to yield 0.10 g of the exemplary compound 1.

(Preparation or Exemplary Compound 111 (Corresponding to Formula (4)))

An exemplary compound 111 was prepared as the same method for the preparation of the exemplary compound 1 except that the ligand (1) was replaced by a ligand (2-1).

(Preparation of Exemplary Compound 75 (Corresponding to Formula (5)))

An exemplary compound 75 was prepared as the same method for the preparation of the exemplary compound 1 except that the ligand (1) was replaced by a ligand (3-1).

(Preparation of Exemplary Compound 84 (Corresponding to Formula (6)))

An exemplary compound 84 was prepared as the same method for the preparation of the exemplary compound 1 except that the ligand (1) was replaced by a ligand (4-1).

(Preparation of Exemplary Compound 69 (Corresponding to Formula (3)))

An exemplary compound 69 was prepared as the same method for the preparation of the exemplary compound 1 except that the ligand (1) was replaced by a ligand (5-1).

(Preparation of Exemplary Compound 64 (Corresponding to Formula (2)))

An exemplary compound 64 was prepared as the same method for the preparation of the exemplary compound 1 except that the ligand (1) was replaced by a ligand (6-1).

Structures of the resulting exemplary compounds were determined with $^1$H-NMR (nuclear magnetic resonance) spectra and mass spectra.

[Chem. 24]

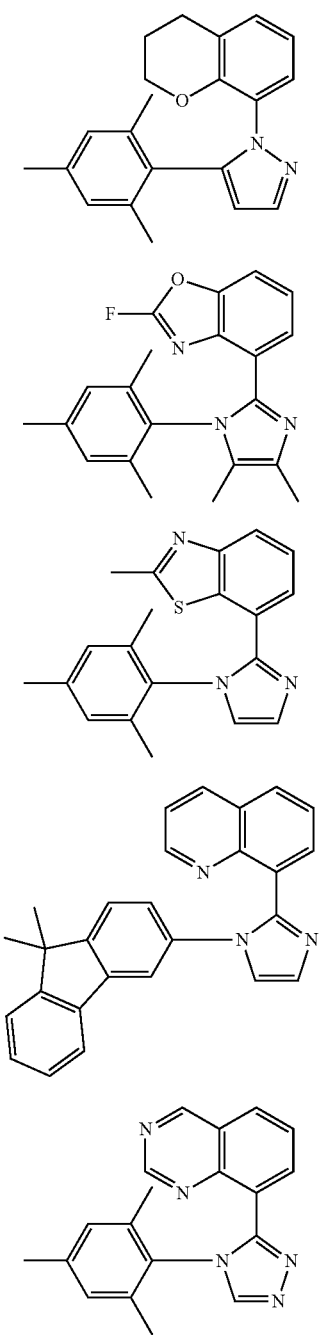

LIGAND (2-1)

LIGAND (3-1)

LIGAND (4-1)

LIGAND (5-1)

LIGAND (6-1)

(Structural Layers of Organic EL Element)

Structural layers that form an organic EL element according to the present invention will be described.

The organic EL element according to the present invention preferably includes an emissive layer between an anode and a cathode, and a layer containing the compound A between the anode and the cathode. In a preferred embodiment, the layer containing the compound A is the emissive layer.

That is, a preferred embodiment is such that the compound A according to the present invention functions as an emissive dopant described below.

Preferred specific examples of the layer structure of the organic EL element in the present, invention are shown below, but the present invention is not limited to:
(i) anode/emissive layer/electron transfer layer/cathode;
(ii) anode/hole transfer layer/emissive layer/electron transfer layer/cathode;
(iii) anode/hole transfer layer/emissive layer/hole blocking layer/electron transfer layer/cathode;
(iv) anode/hole transfer layer/emissive layer/hole blocking layer/electron transfer layer/cathode buffer layer/cathode;
(v) anode/anode buffer layer/hole transfer layer/emissive layer/hole blocking layer/electron transfer layer/cathode buffer layer/cathode;
(vi) anode/hole transfer layer/electron blocking layer/emissive layer/hole blocking layer/electron transfer layer/cathode.

The organic EL element according to the present invention, a blue emissive layer has preferably a maximum emission wavelength in the range of 430 to 480 nm, a green emissive layer has preferably a maximum emission wavelength in the range of 510 to 550 nm, and a red emissive layer has preferably a maximum emission wavelength in the range of 600 to 640 nm, each of which being preferably a monochromatic emissive layer, and a display device including these layers is preferable. Also, at least three of these emissive layers may be stacked to form a white emissive layer, and the organic EL element according to the present invention is preferably a lighting device including these emissive layers. Moreover, the organic EL element according to the present invention may include a non-emissive interlayer between emissive layers.

Each layer in the organic EL element according to the present invention will be described.

(Emissive Layer)

In an emissive layer according to the present invention, electrons and holes are injected and recombined to emit light, and the emission or light may occur in the layer or at the interface between the emissive layer and adjacent layers.

The total thickness of the emissive layers is not limited, but is preferably adjusted in the range of 2 nm to 5 μm, more preferably in the range of 2 nm to 200 nm, and especially preferably in the range of 10 to 20 nm from the viewpoints of film uniformity, prevention of application of an unwanted high voltage at the emission of light, and improvement in stability of an emitted color with respect to the drive current.

The emissive layer can be formed by a film forming of an emissive dopant or a host compound by a known thin-film forming method such as a vacuum deposition method, a spin coating method, a casting method, LB technique, and an ink-jet method. Particularly preferably, the emissive layer is formed with a coating liquid containing the compound A according to the present invention.

The emissive layer in the organic EL element according to the present invention contains both a host compound and at least one emissive dopant (such as a phosphorescent compound false referred to as a phosphorescent dopant) and a fluorescent dopant). Other dopants that can be used as an emissive dopant will be described, although the compound A is preferably used.

(Host Compound (Also Referred to as an Emissive Host))

A host compound used for the present invention will be described.

The host compound in the present invention referred to herein is defined as a compound that is present at a mass ratio in the emissive layer of 20% or more among compounds contained in the layer and has a phosphorescence quantum yield for phosphorescence emission at room temperature (25° C.) of less than 0.1. The phosphorescence quantum yield is preferably less than 0.01.

A known host compound may be used alone or a plurality of host compounds may be used in combination. Use of the host compounds in combination allows for adjustment of charge transfer, resulting in a more efficient organic EL element. Also, use of the emissive dopants described below in combination allows for mixture of different emissions of light, resulting in desirable emission color.

The host compound used for the present invention may be conventionally known low molecular weight compounds, macromolecular compounds having constitutional repeating units, or low molecular weight compounds having a polymerizable group such as a vinyl group said an epoxy group (a vapor deposition polymerizable host).

Specific examples of the host compound preferably used for the present invention are shown below, but the present invention is not limited to:

[Chem. 25]

H-1

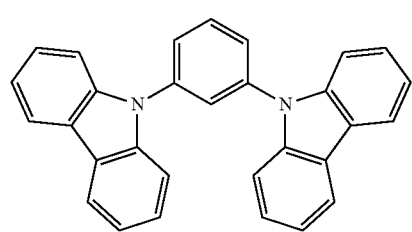

H-2

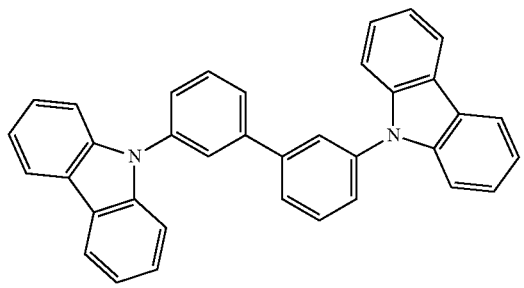

H-3

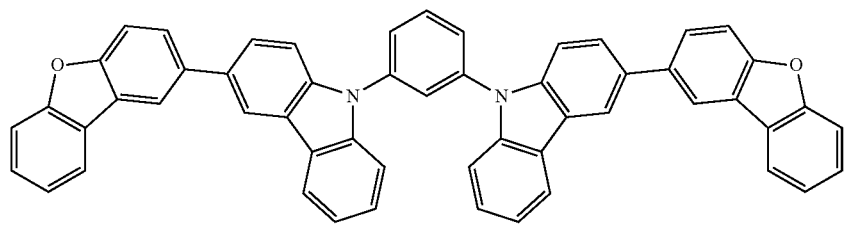

H-4

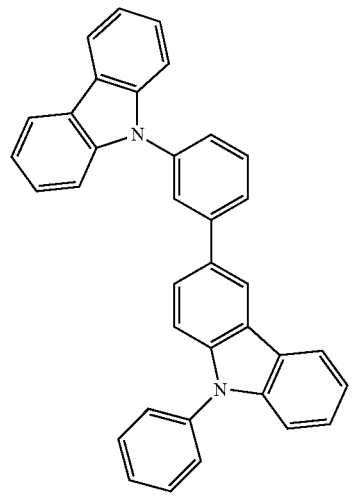

H-5

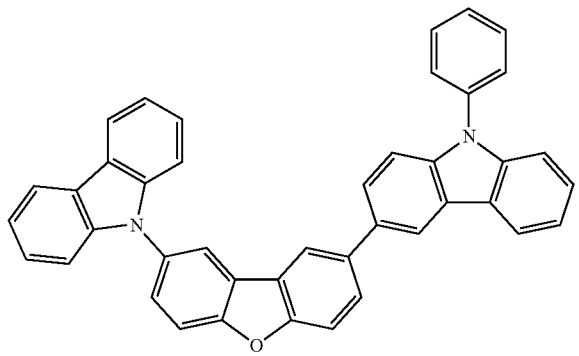

H-6

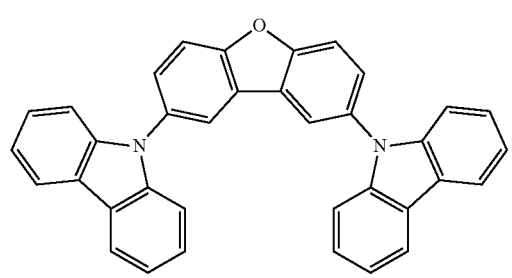

-continued
H-7
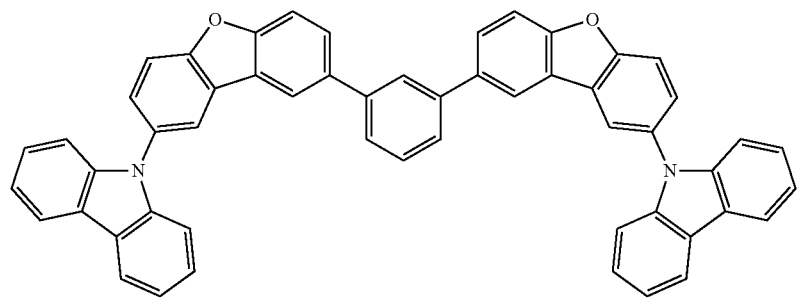
H-8
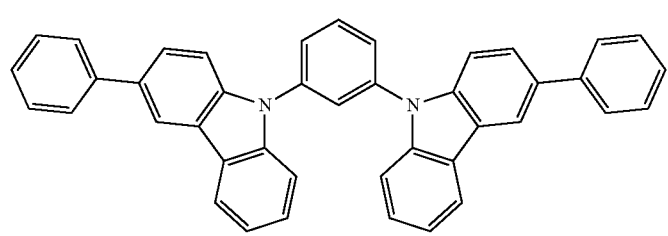
[Chem. 26]
H-9
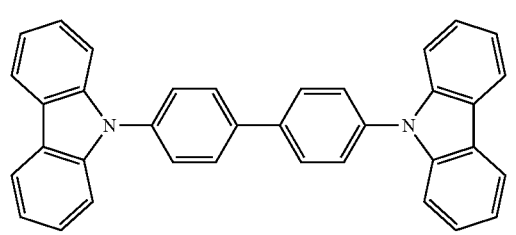
H-10
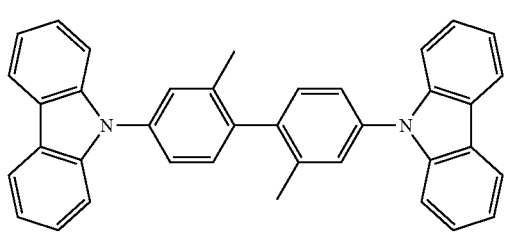
H-11
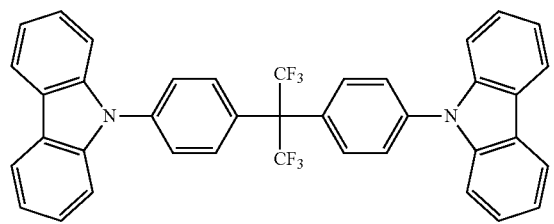
H-12
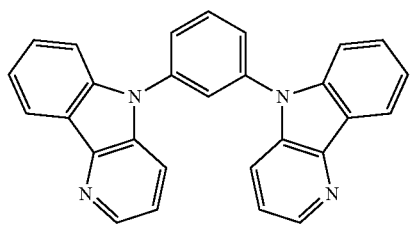
H-13
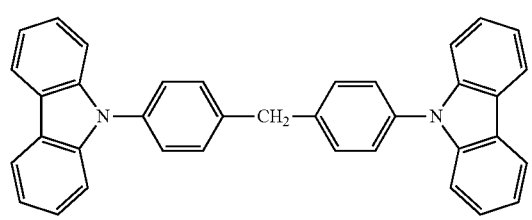
H-14
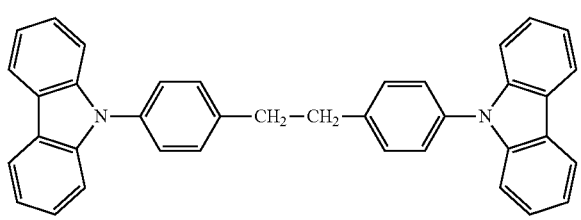
H-15
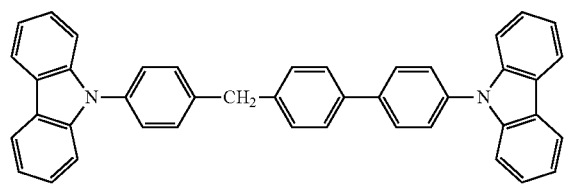
H-16
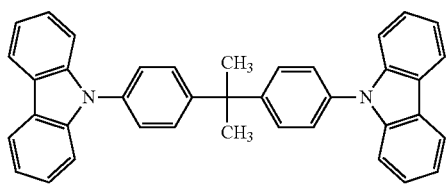

-continued
[Chem. 27]
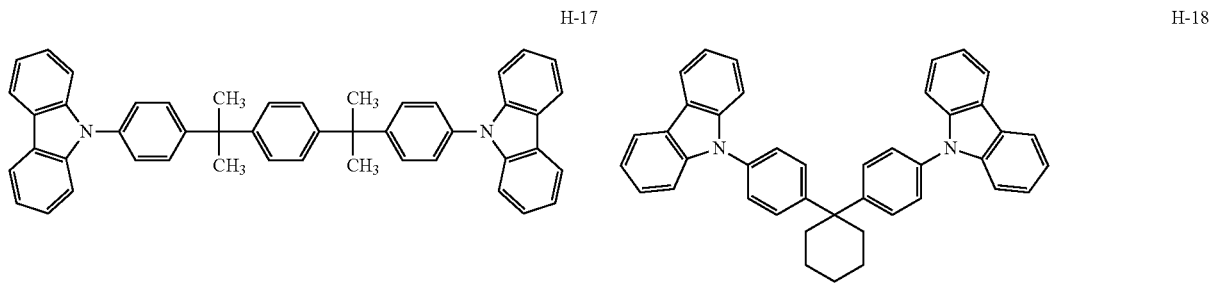
H-17
H-18
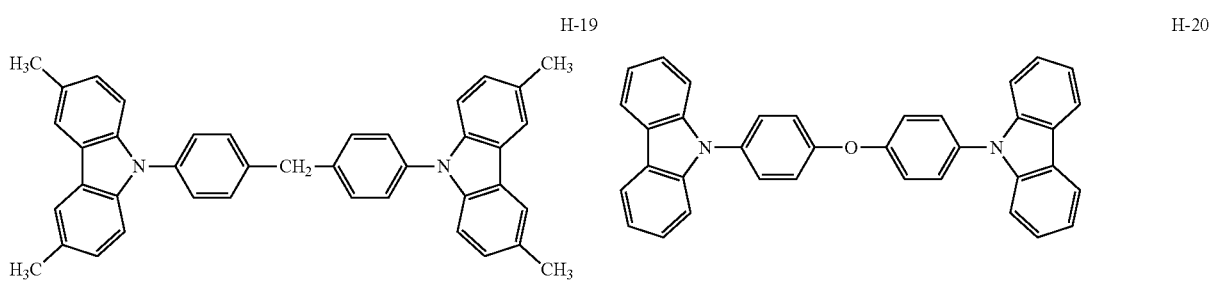
H-19
H-20
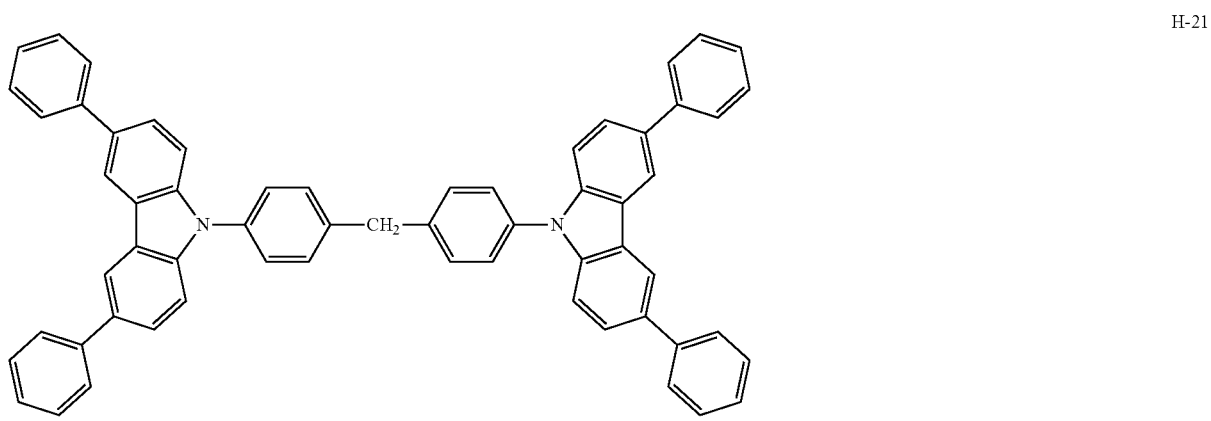
H-21
[Chem. 28]
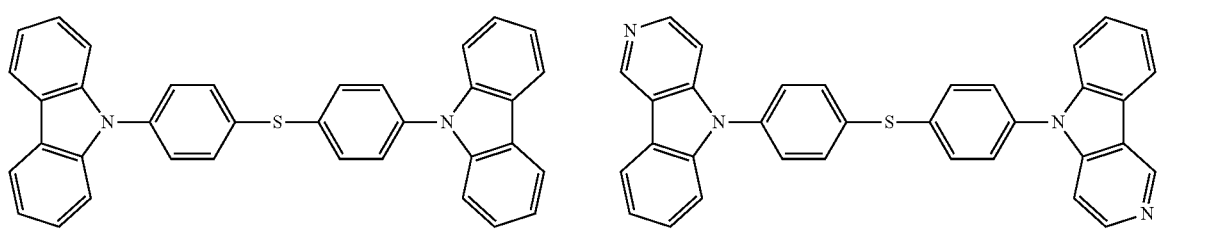
H-22
H-23

-continued
H-24
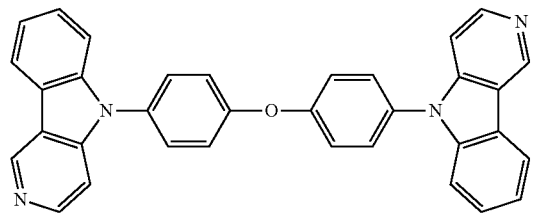
H-25
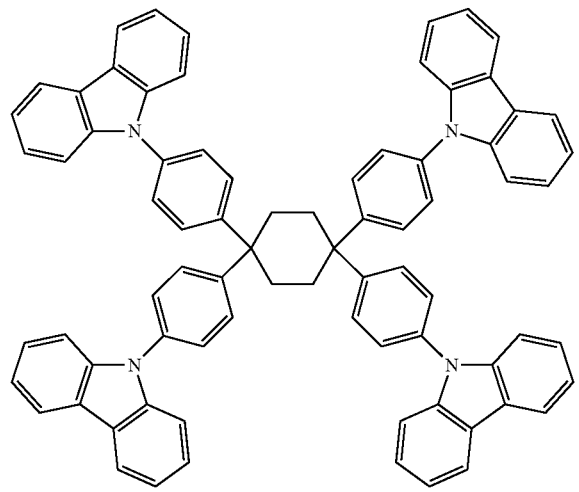
H-26
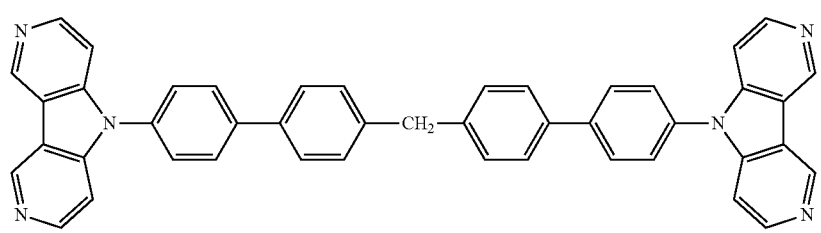
H-27
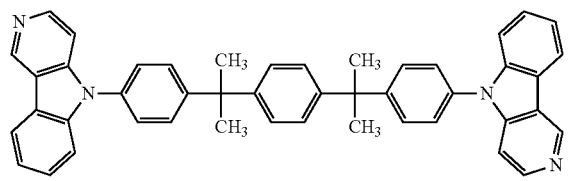
H-28
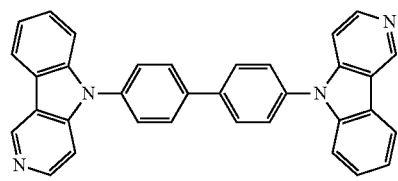
[Chem. 29]
H-29
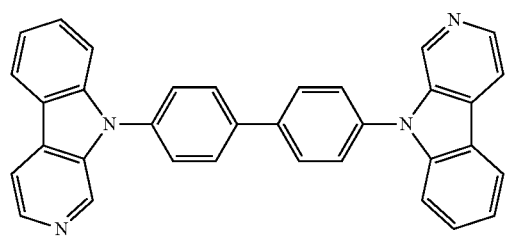
H-30
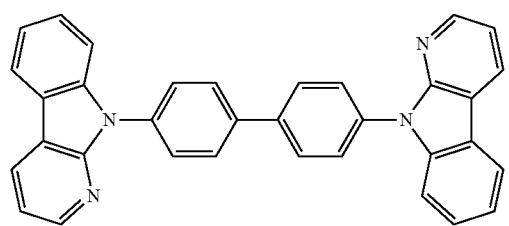
H-31
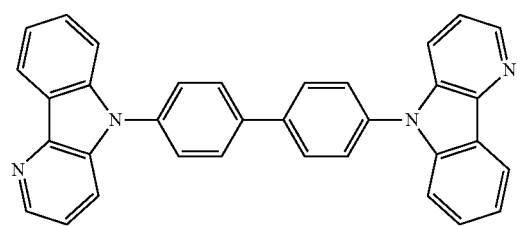

-continued

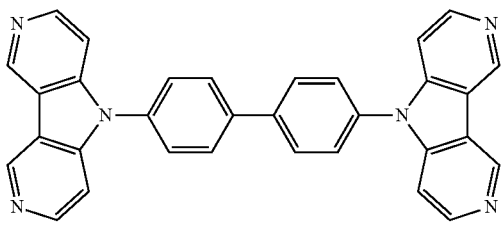
H-32

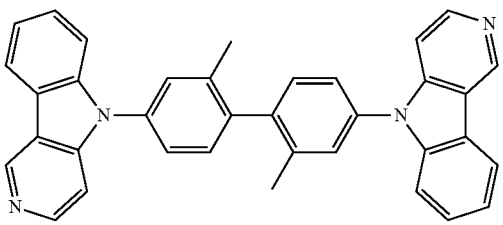
H-33

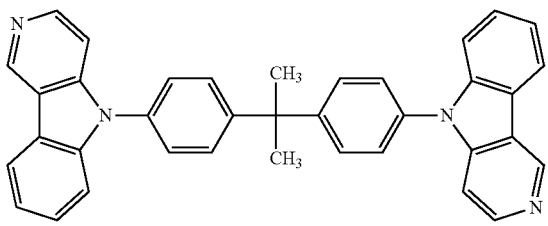
H-34

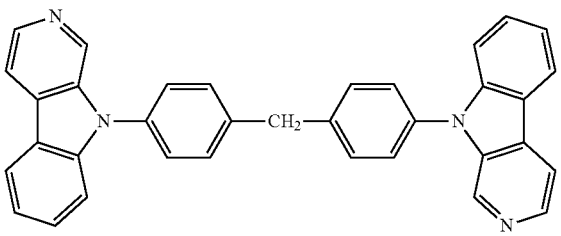
H-35

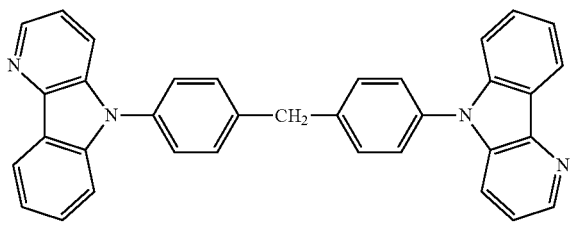
H-36

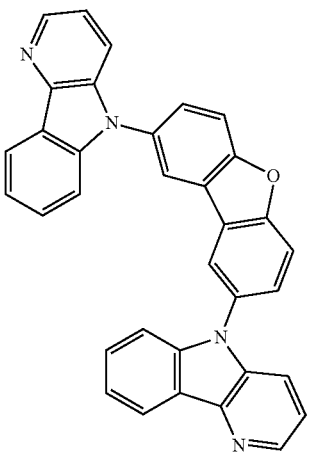
H-37

Known host compounds that may be used in combination are preferably compounds having a hole transfer ability and an electron transfer ability, preventing sift of the emission wavelength to a longer range, and exhibiting a high Tg (glass transition temperature).

Specific examples of the known host compounds include compounds described in the following literatures:
Japanese Patent Application Laid-Open Publication Nos. 2001-257076, 2002-308355, 2001-313179, 2002-319491, 2001-357977, 2002-334786, 2002-8860, 2002-334737, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, and 2002-308837.

(Emissive Dopant)

Emissive dopants can include fluorescent dopants (also referred to as fluorescent compounds) and phosphorescent dopants. From the viewpoint of production of organic EL elements having higher emission efficiencies, emissive dopants (also referred to as simply "emissive materials") used for the emissive layer and emissive unit in the organic EL element according to the present invention preferably contain a phosphorescent dopant together with a host compound described above.

(Phosphorescent Dopant)

The phosphorescent dopant is a compound, that emits light from an excited triplet state. Specifically, a compound that phosphorescence is observed at room temperature (25° C.), and is defined as having a phosphorescence quantum yield of 0.01 or more at 25° C., and preferably of 0.1 or more.

The phosphorescence quantum yield can be determined by the method described in Jikken Kagaku Koza, Bunko (spectrum) II, 4th edition, Vol. 7, p. 398 (1992, Maruzen). The phosphorescence quantum yield in solution can be determined using various solvents. The phosphorescent dopant according to the present invention may have the phosphorescence quantum yield (0.01 or more) at least in one of the solvents.

There are two types of emission of the phosphorescent dopant in principle: one is an energy transfer type, wherein carriers recombine on a host compound to which, the carriers are transferred to create an excited state of the host compound, and this energy is transferred to a phosphorescent dopant to generate emission from the phosphorescent dopant; the other is a carrier trap-type, in which a phosphorescent dopant acts as a carrier trap, and recombination of carriers occurs on the phosphorescent dopant to generate emission from the phosphorescent dopant. In any case, the energy at the excited state of the phosphorescent dopant is required to be lower than the energy at the excited state of the host compound.

The phosphorescent dopants can be suitably selected from known compounds that are used for an emissive layer in an organic EL element. Specific examples of the phosphorescent dopants include compounds described in the following patent literatures.

International Publication No. WO00/70655, Japanese Patent Application Laid-Open Publication Nos. 2002-280178, 2001-181616, 2002-280179, 2001-181617, 2002-280180, 2001-247859, 2002-299060, 2001-313178, 2002-302671, 2001-345183, and 2002-324679, International Publication No. WO02/15645, Japanese Patent Application lard-Open Publication Nos. 2002-332291, 2002-50484, 2002-332292, and 2002-83684, National Publication of International Patent Application No. 2002-540572, Japanese Patent Application Laid-Open Publication Nos. 2002-11.7978, 2002-338588, 2002-170684, and 2002-352960, International Publication No. WO01/93642, Japanese Patent Application Laid-Open Publication Nos. 2002-50483, 2002-100476, 2002-173674, 2002-359082, 2002-175884, 2002-363552, 2002-184582, and 2003-7469, National Publication of International Patent Application No. 2002-525808, Japanese Patent Application Laid-Open Publication No. 2003-7471, National Publication of International Patent Application No. 2002-525833, Japanese Patent Application Laid-Open Publication Nos. 2003-31366, 2002-226435, 2002-234894, 2002-235076, 2002-241751, 2001-319779, 2001-319780, 2002-62824, 2002-100474, 2002-203679, 2002-343572, and 2002-203678.

The phosphorescent dopant according to the present invention is preferably a complex compound containing a metal in Groups VIII to X of the periodic table, more preferably an iridium compound, an osmium compound, or a platinum compound (platinum complex compound), and a rare earth complex, and most preferred is an iridium compound.

The compound that is used as a phosphorescent dopant is preferably an organometallic complex having a structure represented by any one of Formulae (2) to (7).

Also, conventionally known emissive dopants as shown below may be used in combination.

[Chem. 30]

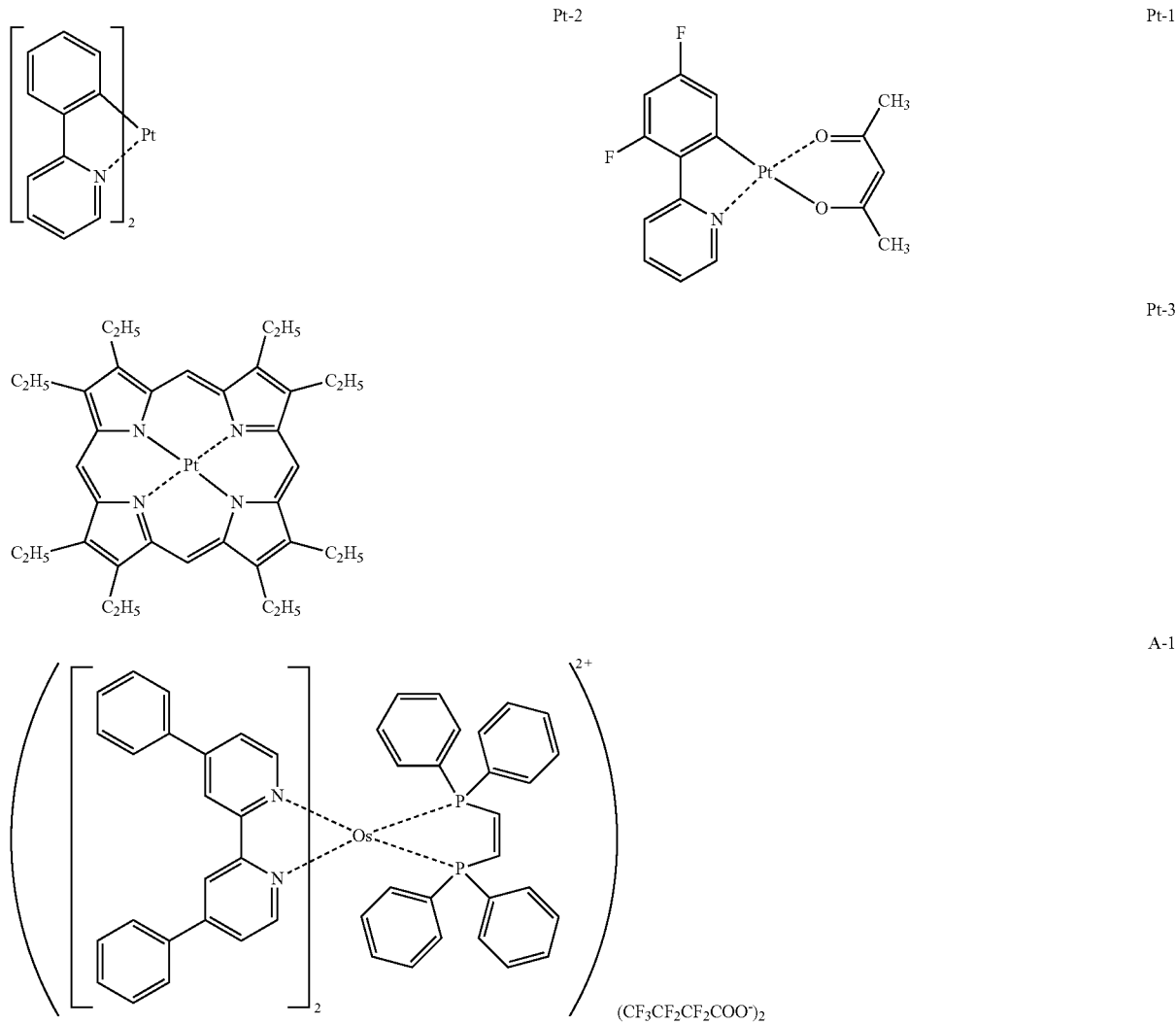

[Chem. 31]
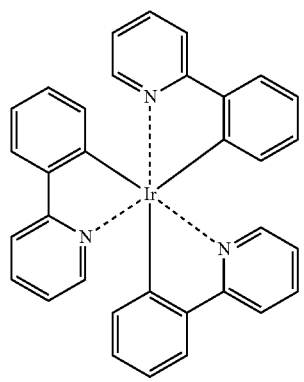
Ir-1
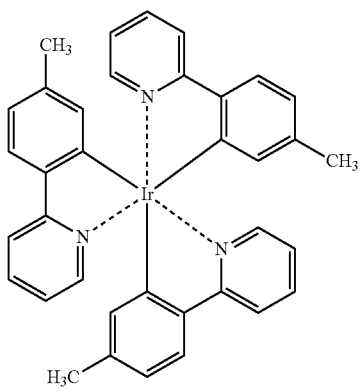
Ir-2
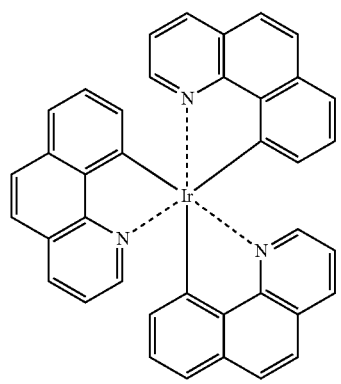
Ir-3
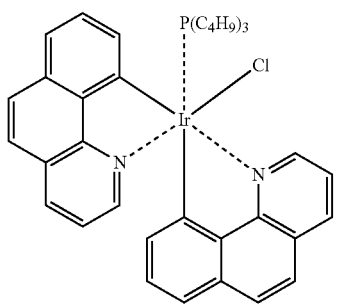
Ir-4
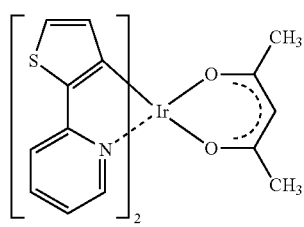
Ir-5
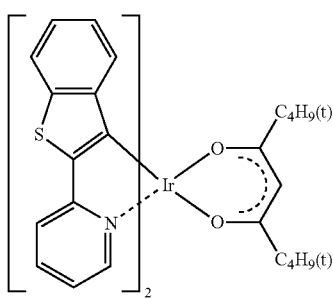
Ir-6
[Chem. 32]
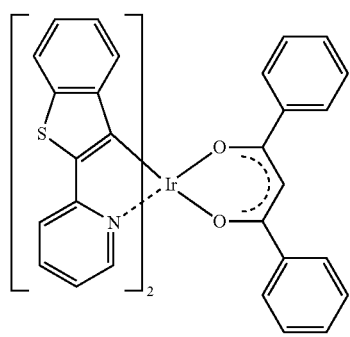
Ir-7
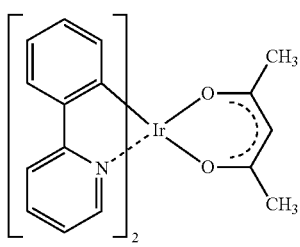
Ir-8

Ir-9
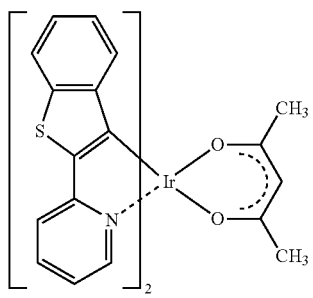
Ir-10
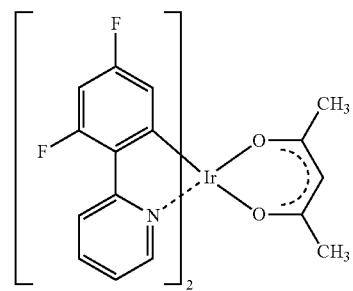
Ir-11
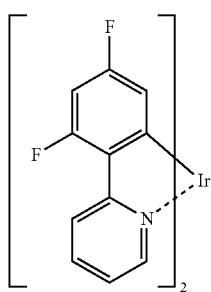
Ir-12
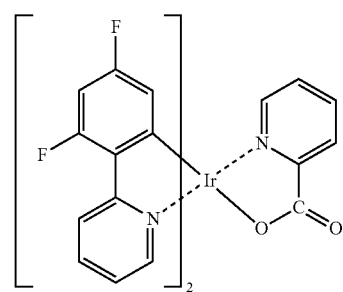
Ir-14
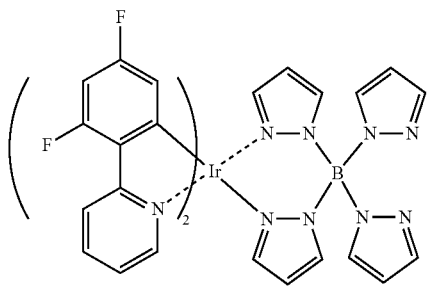
[Chem. 33]
Ir-15
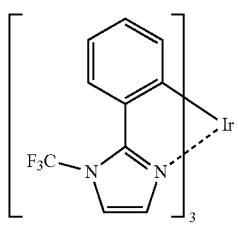
Ir-16
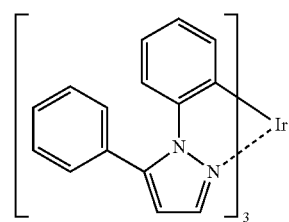
Ir-17
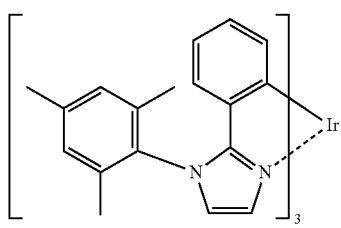
Ir-18
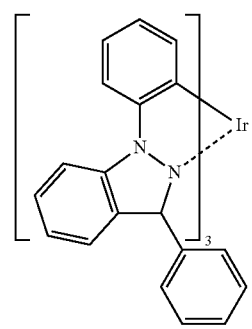

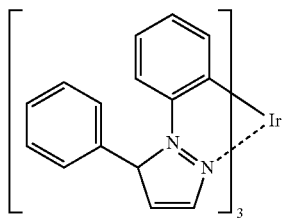

Ir-19

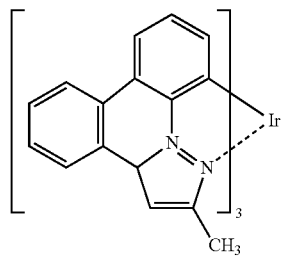

Ir-20

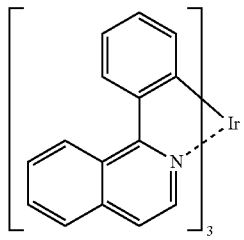

Ir-21

(Fluorescent Dopant (Also Referred to as Fluorescent Compound))

Examples of the fluorescent dopant include a coumarin dye, a pyrane dye, a cyanine dye, a chloconium dye, a squarylium dye, an oxobenzanthracene dye, a fluorescein dye, a rhodamine dye, a pyrylium aye, a perylene dye, a stilbene dye, a polythiophene dye, or a rare earth complex phosphor.

Injection layers, blocking layers, a hole transfer layer, and an electron transfer layer used for structural layers in the organic EL element according to the present invention will now be described.

(Injection Layer: Electron Injection Layer and Hole Injection Layer)

Injection layer may be provided as necessary. There are two binds of layers of an electron injection layer and a hole injection layer, and it may be interposed between an anode and an emissive layer or a hole transfer layer and between a cathode and an emissive layer or an electron transfer layer as described above.

The injection layer is interposed between an electrode and an organic layer for decreasing in drive voltage and an improvement in luminance and includes a hole injection layer (an anode buffer layer) and an electron injection layer (a cathode buffer layer), and details are described in "Part 2, Chapter 2: Denkyoku Zairyo" in "Yuki EL soshi to sono kogyoka saizensen (Nov. 30, 1998, published by NTS Inc.)" (pp. 123 to 166).

The anode buffer layer (a hole injection layer) is also described in detail in Japanese Patent Application Laid-Open Publication Nos. 9-45479, 9-260062, and 8-288069, and specific examples of the anode buffer layer include a phthalocyanine buffer layer represented by copper phthalocyanine, an oxide buffer layer represented by vanadium oxide, an amorphous carbon buffer layer, and a polymer buffer layer containing a conductive polymer such as polyaniline (emeraldine) and polythiophene.

The cathode buffer layer (an electron injection layer) is also described in detail in Japanese Patent Application Laid-Open Publication Nos. 6-325871, 9-17574, and 10-74586, and specific examples of the cathode buffer layer include a metal buffer layer represented by strontium and aluminum, an alkali metal compound buffer layer represented by lithium fluoride, an alkaline earth metal compound buffer layer represented by magnesium fluoride, and an oxide buffer layer represented by aluminum oxide.

The injection layers can be formed by thin-film formation of the above materials using a known method such as a vacuum deposition, a spin coating method, a casting method, an ink-jet method, and LB technique.

The buffer layers (injection layers) are desirably extremely thin films. Depending on the materials, the thickness of the film is preferably in the range of 0.1 nm to 5 μm. The injection layer may have a monolayer structure formed of at least one of the materials described above.

(Blocking Layer: Hole Blocking Layer and Electron Blocking Layer)

As described above, a blocking layer is provided, as necessary, in addition to basic component layers in an organic compound thin film. For example, a hole blocking layer is described in Japanese Patent Application Laid-Open Publication Nos. 11-204258 and 11-204359, and "Yuki EL soshi to sono kogyoka saizensen", p. 237 (Nov. 30, 1998, published by NTS Inc.).

The hole blocking layer functions as an electron transfer layer in a broad sense, is formed of a hole blocking material that shows a remarkably poor ability to transport holes while transporting electrons, and then can block holes while transporting electrons to enhance the recombination probability between electrons and holes. Moreover, the structure of an electron transfer layer described below can be used as a hole blocking layer, as necessary.

The hole blocking layer preferably contains a carbazole derivative, a carboline derivative, a diazacarbazole derivative (a derivative in which one of the carbon, atoms in the carboline ring in the carboline derivative is replaced by a nitrogen atom).

Moreover, in the present invention, when the organic EL element includes a plurality of different emissive layers having a plurality of emission colors, an emissive layer of which the maximum emission wavelength exists at the shortest wavelength side is preferably the closest to the anode among all the emissive layers. In such a case, a hole blocking layer is preferably interposed additionally between the emissive layer having the maximum emission at the shortest wavelength and an emissive layer which is the second closest to the anode. In addition, 50% by mass or more of the compound contained in the hole blocking layer arranged at the position preferably have an ionization potential at least 0.3 eV higher than that the host compound in the emissive layer having the maximum emission at the shortest wavelength.

Ionization potential is defined in terms of the energy required to release the electron of a compound from the HOMO (highest occupied molecular orbital) level to vacuum level, and can be determined by the method described, below, for example.

Preferably, a low-energy electron spectrometer Model AC-1 from Riken Keiki Co., Ltd. or the method known as ultraviolet photo-electron spectroscopy can be used.

On the other hand, an electron blocking layer functions as a hole transfer layer in a broad sense, is formed of a material that shows a remarkably poor ability to transport electrons while having transporting holes, and then can block electrons while transporting holes to enhance the recombination probability between electrons and holes.

Moreover, the structure of a hole transfer layer described below can be used as an electron blocking layer, as necessary. The hole blocking layer and the electron blocking layer each have a thickness of preferably 3 to 100 nm, and more preferably 5 to 30 nm.

(Hole Transfer Layer)

The hole transfer layer is formed of a hole transfer material that can transport holes. In a broad sense, the hole injection layer and the electron blocking layer also functions as a hole transfer layer. The hole transfer layer can be provided as a single layer or multiple layers.

The hole transfer material may have any one of hole injection or transfer characteristics and electron-blocking characteristics, and may be organic or inorganic. Examples of the hole transfer material include triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and conductive polymeric oligomers, and thiophene oligomers in particular.

As the hole transfer material, the compounds described above can be used, and preferred are a porphyrin compound, an aromatic tertiary amine compound and a styrylamine compound, and an aromatic tertiary amine compound in particular.

Representative examples of the aromatic tertiary amine compound and the styrylamine compound include N,N,N', N'-tetraphenyl-4,4'-diamine-phenyl, N,N'-diphenyl-N,N'-bis(3-methylphenyl)-[1,1'-biphenyl]-4,4'-diamine (TPD), 2,2-bis(4-di-p-tolylaminophenyl)propane, 1,1-bis(4-di-p-tolylaminophenyl)cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino)quadriphenyl, N,N,N-tri(p-tolyl)amine, 4-(di-p-tolylamino)-4'-[4-(di-p-tolylamino)styryl]stilbene, 4-N,N-diphenylamino(2-diphenylvinyl)benzene, 3-methoxy-4'-N,N-diphenylaminostilbene, N-phenylcarbazole, as well as a compound having two condensed aromatic rings within its molecule described in U.S. Pat. No. 5,061,569, for example, 4,4'-bis[N-(1-naphthyl)-N-phenylamino]biphenyl (NPD), and 4,4',4"-tris[N-(3-methylphenyl)-N-phenylamino]triphenylamine (MTDATA) in which three triphenylamine units are linked in a starburst form as described in Japanese Patent Application Laid-Open Publication No. 4-308688.

Moreover, polymeric materials prepared by introducing these materials to a polymer chain, or by employing these materials as a polymer main chain, may be used. In addition, inorganic compounds such as p-type Si and p-type SiC can also be used as a hole injection material or a hole transfer material.

Furthermore, the so-called p-type hole transfer materials can be used as described in Japanese Patent Application Laid-Open Publication No. 11-251067, and J. Huang et. al., Applied Physics Letters 80(2002), p. 139. In the present invention, these materials can preferably be used from the viewpoints of production of more efficient organic EL elements.

The hole transfer layer can be formed by thin-film formation using the above hole transfer materials with a known method such as a vacuum deposition method, a spin coating method, a casting method, a printing method including an ink-jet method, and LB technique. The thickness of the hole transfer layer is not limited, but is typically about 5 nm to 5 μm, and preferably 5 to 200 nm. The hole transfer layer may have a monolayer structure formed of at least one of the materials described above.

Also, a high p-type (high positive property) hole transfer layer doped with impurities can be used. Examples of such a hole transfer layer include those described in Japanese Patent Application Lard-Open Publication Nos. 4-5297076, 2000-196140, and 2001-102175, and J. Appl. Phys., 95, 5773 (2004).

In the present invention, such a high p-type hole transfer layer is preferably used because lower power consuming elements can be produced.

(Electron Transfer Layer)

The electron transfer layer is formed of a material that can transport electrons, and includes the electron injection layer and the hole blocking layer in a broad sense. The electron transfer layer can be provided as a single layer or multiple layers.

Conventionally, as electron transfer materials (also serving as hole blocking materials) used for a single electron transfer layer, or for an electron transfer layer adjacent to the emissive layer on the cathode side when provided as multiple layers, it is enough only that they have a function to transmit electrons injected from the cathode to the emissive layer, and can be any compound selected from conventionally known compounds. Examples of the electron transfer materials include nitro-substituted fluorene derivatives, diphenylquinone derivatives, thiopyrandioxide derivatives, carbodiimides, fluorenylidenemethane derivatives, anthraquinodimethane and enthrone derivatives, oxadiazole derivatives.

Moreover, thiadiazole derivatives in which the oxygen atom on the oxadiazole ring in the oxadiazole derivatives was replaced by a sulfur atom, and quinoxaline derivatives having a quinoxaline ring known as an electron-withdrawing group can also be used as electron transfer materials. Moreover, polymeric materials prepared by introducing these materials to a polymer chain or by employing these materials as a polymer main chain may be used.

Furthermore, metal complexes of 8-quinolinol derivatives, such as tris(8-quinolinol)aluminum (Alq), tris(5,7-dichloro-8-quinolinol; aluminum, tris(5,7-dibromo-8-quinolinol)aluminum, tris(2-methyl-8-quinolinol)aluminum, tris(5-methyl-8-quinolinol)aluminum, and bis(8-quinolinol)

zinc (Znq), and metal complexes in which the central metal is replaced by In, Mg, Cu, Ca, Sn, Ga or Pb can also be used as electron transfer materials.

Besides, metal-free or metal phthalocyanines, or these phthalocyanines of which the termini are substituted with an alkyl group or a sulfonic acid group can be used as electron transfer materials. Moreover, distyrylpyrazine derivatives exemplified as materials for an emissive layer can also be used as electron transfer materials, and like the hole injection layer and the hole transfer layer, inorganic semiconductors such as n-type Si and n-type SiC can also be used as electron transfer materials.

The electron transfer layer can be formed by thin-film forming using the above electron transfer materials by a known method such as a vacuum deposition method, a spin coating method, a casting method, a printing method including an ink-jet method, and LB technique. The thickness of the electron transfer layer is not limited, but is typically about 5 nm to 5 μm, and preferably 5 to 200 nm. The electron transfer layer may have a single layer structure formed of at least one of the materials described above.

Also, a high n-type (high negative property) electron transfer layer doped with impurities can be used. Examples of such a electron transfer layer include those described in Japanese Patent Application Laid-open Publication Nos. 4-297076, 10-270172, 2000-196140, and 2001-102175, and J. Appl. Phys., 95, 5773 (2004).

Such a high n-type electron transfer layer is preferably used because lower power consuming elements can be produced.

(Anode)

An anode used in the organic EL element preferably employs a metal, an alloy, an electroconductive compound, and a mixture thereof each having a high work function (4 eV or more) as an electrode material. Specific examples of such an electrode material include metals such as Au, and transparent conductive materials such as CuI, indium tin oxide (ITO), $SnO_2$, and $ZnO_2$.

A material such as IDIXO ($Ir_2O_3$—ZnO) that is amorphous and capable of producing a transparent conductive film can also be used. The anode may be prepared by forming a thin film of such an electrode material by a method such as deposition and sputtering, and patterning the thin film into a desired shape by photolithography, or by patterning during deposition or sputtering of the electrode material through a mask having a desired shape when high precision of patterning is not required (about 100 μm or more).

Alternatively, if an applicable substance such as an organic conductive compound is used, wet film-forming methods such as a printing method and a coating method can also be used. When light is emitted through the anode, the transmittance of the anode is preferably more than 10%, and the sheet resistance of the anode is preferably several hundred ohm/□ (square) or less. Depending on the material, the thickness is selected typically within the range of 10 to 1000 nm, and preferably within the range of 10 to 200 nm.

(Cathode)

On the other hand, a metal of a low work function (4 eV or less) (an electron injection metal), an alloy, an electroconductive compound, and a mixture thereof as an electrode material is used as a cathode. Specific examples of such an electrode material include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, aluminum and a rare earth metal.

Among these electrode materials, a mixture of an electron injection metal and a second, metal which is a stable metal having a higher work function than that of the electron injection metal, such as a magnesium/silver mixture, a magnesium/aluminum mixture, a magnesium/indium mixture, a aluminum/aluminum oxide ($Al_2O_3$) mixture, a lithium/aluminum mixture, and aluminum is suitable from the viewpoints of electron injection characteristics and endurance to oxidation.

The cathode may be prepared by forming a thin film of such an electrode material by a method such as deposition and sputtering. Moreover, the sheet resistance of the cathode is preferably several hundred ohm/□ (square) or less, and the thickness is selected within the range of 10 nm to 5 μm, and preferably 50 to 200 nm.

If either the anode or the cathode in the organic EL element is transparent or translucent for transmitting the emitted light, then luminance is advantageously improved.

A transparent or translucent cathode can be prepared by forming the metal described above into a layer having a thickness of 1 nm to 20 nm for the cathode, and then on the resulting metal layer, forming the transparent conductive material as described in the explanation of an anode into a layer. The resulting cathode can be used to produce an element in which both anode and cathode have transparency.

(Support Substrate)

A support substrate (also referred to as a base, a substrate, a base material, or a support) used for the organic EL element according to the present invention may be any kind of material such as glass and plastic, and be transparent or opaque. When light is emitted through the support substrate, the support substrate is preferably transparent. Examples of the transparent support substrate preferably used include glass, quartz, and transparent resin film. An especially preferable support substrate is a resin film that can provide the organic EL element with flexibility.

Examples of the resin, film include polyesters such as polyethylene terephthalate (PET) and polyethylene naphthalate (PEN), polyethylenes, polypropylenes, cellophane, cellulose esters or derivatives thereof such as cellulose diacetate, cellulose triacetate, cellulose acetate butyrate, cellulose acetate propionate (CAP), cellulose acetate phthalate (TAC) and cellulose nitrate, polyvinylidene chlorides, polyvinyl alcohols, polyethylene vinyl alcohols, syndiotactic polystyrenes, polycarbonates, norbornene resins, polymethylpentenes, polyester ketones, polyimides, polyether sulfones (PES), polyphenylene sulfides, polysulfones, polyether imides, polyether ketone imides, polyamides, fluoroplastic, nylons, polymethyl methacrylates, acrylic or polyarylates, cycloolefin-based resins such as ARTON (from JSR) or APEL (from Mitsui Chemicals, Inc.).

On the surface of the resin film, an inorganic film, an organic film, or a hybrid film of both may be formed. The film may be preferably a barrier film having a water vapor transmission rate, which is measured in accordance with JIS K 7129-1992 (at a temperature of 25±0.5° C. and a relative humidity of 90±2% RH), of 0.01 g/($m^2 \cdot 24$ h) or less, and more preferably a high barrier film having an oxygen transmission rate, which is measured in accordance with JIS K 7126-1987, of $10^{-3}$ ml/($m^2 \cdot 24$ h·atm) or less and a water vapor transmission, rate of $10^{-5}$ g/($m^2 \cdot 24$ h) or less.

A material used for forming the barrier film may be any material provided that it has a function of preventing invasion of a matter that causes degradation of the element such as water and oxygen, and examples of the material include silicon monooxide, silicon dioxide, and silicon nitride. Moreover, the barrier film has preferably a laminated structure of the inorganic layer and a layer formed of an organic material in order to improve the fragility of the film. The inorganic layer and organic layer are stacked in any order, and preferably are alternately stacked multiple times.

The barrier films may be formed by any method. For example, vacuum deposition, sputtering, reactive sputtering, molecular beam epitaxy, cluster ion beam, ion plating, plasma polymerization, atmospheric pressure plasma polymerization, plasma CVD, laser CVD, thermal CVD, and coating methods may be used, and especially preferred is the atmospheric pressure plasma polymerization, method as described in Japanese Patent Application Laid-Open Publication No. 2004-68143.

Examples of the opaque support substrate include a metal plate or film of such as aluminum and stainless steel, an opaque resin substrate and ceramic substrate.

The external emission extraction quantum efficiency at room temperature of an organic EL element according to the present invention is preferably 1% or more, and more preferably 5% or more.

Here, the external emission extraction quantum efficiency (%)=the number of photons externally emitted from the organic EL element/the number of electrons injected to the organic EL element×100.

A hue improving filter such as a color filter may be used in combination, or a color conversion filter that converts emitted color from an organic EL element to multicolor using a phosphor may be used in combination. If the color conversion filter is used, then λ max of the emission in the organic EL element is preferably 480 nm or less.

(Sealing)

An anode, a cathode, and a layer between the cathode and the anode in the organic EL element according to the present invention are preferably blocked and sealed by a sealing member to seal them from the ambient air.

Examples of the means of sealing used for the present invention include a method of attaching a sealing member to an electrode and a support substrate with an adhesive.

The sealing member may be disposed so as to cover the display area of the organic EL element, and may be of the shape of an intaglio plate or flat plate. In addition, transparency and electrical insulating property of the sealing member do not matter.

Specific examples of the sealing member include a glass plate, a polymer plate/film, and a metal plate/film. Examples of the glass plate include, among others, soda-lime glass, barium/strontium-containing glass, lead glass, aluminosilicate glass, borosilicate glass, barium borosilicate glass, and quartz. Examples of the polymer plate include polycarbonate, acrylic, polyethylene terephthalate, polyether sulfide, and polysulfone. Examples of the metal plate include at least one metal or alloy selected from the group consisting of stainless steel, iron, copper, aluminum, magnesium, nickel, zinc, chromium, titanium, molybdenum, silicon, germanium, and tantalum.

In the present invention, polymeric film and metal film can preferably be used, in that the element can be formed into a thin film. Moreover, the polymeric film preferably has an oxygen transmission rate, which is measured in accordance with JIS K 7126-1987, of $1 \times 10^{-3}$ ml/(m$^2$·24 h·atm) or less and a water vapor transmission rate (at 25±0.5° C. and relative humidity (90±2)% RH), which is measured in accordance with JIS K 7129-1992, of $1 \times 10^{-3}$ g/(m$^2$·24 h) or less.

The sealing member is processed in intaglio by sand blasting or chemical etching.

Specific examples of the adhesive include photo-curable and thermosetting adhesives having reactive vinyl groups such as acrylate-based oligomer and methacrylate-based oligomer, and moisture-curable adhesives such as 2-cyanoacrylate ester; also epoxy-based thermosetting and chemically-curable (two-part mixture) adhesives; also hot-melt-type polyamide, polyester and polyolefin; and also cationic curing-type ultraviolet-curable epoxy resin adhesives.

The adhesive can preferably bond and cure at a temperature of room temperature to 80° C. since the organic EL element may degrade by heat-treating. Also, the adhesive may contain a desiccant dispersed therein.

The adhesive may be applied to the part to be sealed by using a commercially available dispenser, or by printing such as screen printing.

It is also preferred to form an inorganic or organic film as a sealing film, on the outer side of the electrode which opposes to the support substrate while placing the organic layer between the electrode and the support substrate, so as to cover the electrode and the organic layer and so as to be in contact with the support substrate.

The material used for forming the film may be any material provided that it has a function of inhibiting invasion of a matter that causes degradation of the element, such as water and oxygen, and examples of the material include silicon monooxide, silicon dioxide, and silicon nitride.

Moreover, the film has preferably a laminated structure of the inorganic layer and a layer formed of an organic material in order to improve the fragility of the film. These films may be formed by any method. For example, vacuum deposition, sputtering, reactive sputtering, molecular beam epitaxy, cluster ion beam, ion plating, plasma polymerisation, atmospheric pressure plasma polymerisation, plasma CVD, laser CVD, thermal CVD, and coating methods may be used.

It is preferred to inject an inert gas such as nitrogen or argon or inert liquid such as fluorocarbon or silicone oil into a gap between the sealing member and the display area of the organic EL element. Also, the gap may be vacuumized. Also, a hygroscopic compound may be encapsulated therein.

Examples of the hygroscopic compound include metal oxides (such as sodium oxide, potassium oxide, calcium oxide, barium oxide, magnesium oxide, and aluminum oxide), sulfates (such as sodium sulfate, calcium sulfate, magnesium sulfate, and cobalt sulfate), metal halides (such as calcium chloride, magnesium chloride, cesium, fluoride, tantalum fluoride, cerium bromide, magnesium bromide, barium iodide, and magnesium iodide), and per chlorates (such as barium perchlorate and magnesium perchlorate). Anhydride is preferable for sulfates, metal halides and perchlorates.

(Protective Film/Plate)

For enhancing the mechanical strength of the element, a protective film or plate may be provided on the outer side of the sealing member described above which is opposed to the support substrate with the organic layer interposed between the support substrate and the sealing film. Such a protective film or plate is preferably provided especially when the sealing is given by the sealing film, because the mechanical strength provided by the sealing film is not always high. Examples of materials that can be used for this protective film or plate include glass plates, polymer plates or films, and metal plates or films, which are similar to those used for sealing described above. Preferred are polymer films due to their light weight and capability of thin-film forming.

(Light Extraction)

The organic EL element emits light inside a layer having a higher refractive index (about 1.7 to 2.1) than that air has, and it is generally believed that only about 15 to 20% of light emitted inside the emissive layer can be extracted. This is because incident light to the interface (between the transparent substrate and the air) at an angle θ larger than the critical angle causes total reflection and cannot be extracted to the outside of the element, and because the light causes total reflection between the transparent electrode or emissive layer and the transparent substrate, is guided through the transparent electrode or emissive layer, and consequently escapes in the direction to the side faces of the element.

Examples of techniques for improving the efficiency of light extraction include a method of forming an irregularity on the surface of the transparent substrate to prevent total reflection at the interface between the transparent substrate and the air (U.S. Pat. No. 4,774,435), a method of providing a light condensing substrate to improve the efficiency (Japanese Patent Application Laid-open Publication No. 63-314795), a method of forming a reflective surface on the side faces of the element (Japanese Patent Application Laid-Open Publication No. 1-220394), a method of interposing a flat layer having an intermediate refractive index between the substrate and the luminophor to form an anti-reflection film (Japanese Patent Application Laid-Open Publication No. 62-172691), a method of interposing a flat film having a refractive index lower than that of the substrate between the substrate and she luminophor (Japanese Patent Application Laid-open Publication No. 2001-202827), and a method of forming a diffraction grating between any two of the substrate, the transparent electrode layer, and the emissive layer (including between the substrate and the external) (Japanese Patent Application Laid-Open Publication No. 11-283751).

In the present invention, these methods can be used in combination with the organic EL element according to the present invention, and preferably the method of interposing a flat layer having a refractive index lower than that of the substrate between the substrate and the luminophor, or the method of forming a diffraction grating between any two of the substrate, the transparent electrode layer and the emissive layer (including between the substrate and the external) can be used.

In the present invention, these means can be combined to produce an element having a further high luminance or improved endurance.

When a medium having a low refractive index is formed in a thickness longer than the wavelength of light between the transparent electrode and the transparent substrate, the lower refractive index of the medium, the higher efficiency of external extraction of light emitted from the transparent electrode can be achieved.

Examples of the low refractive index layer include aerogel, porous silica, magnesium, fluoride, and fluorinated polymer. The transparent substrate generally has a refractive index of about 1.5 to 1.1, and thus the low-refractive-index medium preferably has a refractive index of about 1.5 or less; and more preferably 1.35 or less.

In addition, the low-refractive-index medium is desirably twice or more as thick as the wavelength in the medium. If the thickness of the low-refractive-index medium is reduced to about the wavelength of light, evanescent waves are penetrated into the substrate. Such a thickness impairs the effect of the low-refractive-index layer.

The method of introducing a diffraction grating, at the interface causing total, reflection or in any medium, is characterized in that it is highly effective in improving the light extraction efficiency. The method takes advantage of the nature of the diffraction grating that changes the direction of light into a specific direction different from the direction of refraction, by the so-called Bragg diffraction including primary diffraction and secondary diffraction. The method is intended to extract a part of light emitted from the emissive layer, which cannot fail out the exterior due to total reflection taking place between the layers, by introducing the diffraction grating between any layers or in the medium (in the transparent support substrate or the transparent electrode) to diffract the light.

The diffraction grating to be introduced preferably has a two-dimensionally periodic refractive index. This is because a general one-dimensional diffraction grating having a refractive index distribution periodic only in a certain direction diffracts only a part of light travelling in a specific direction, and then cannot improve the light extraction efficiency for light emitted from the emissive layer randomly in all directions.

However, a two-dimensional distribution of refractive index can allows for diffraction of light travelling in all directions, resulting in an increase in the light extraction efficiency.

The diffraction grating may be introduced between any layers or in the medium (in the transparent support substrate or the transparent electrode) as described above and preferably close to the organic emissive layer where light is emitted.

The periodicity of diffraction grating is preferably about ½ to 3 times the wavelength of light in the medium. The arrangement of diffraction grating is preferably two-dimensionally repeating arrangement, such as orthogonal lattice, triangular lattice, and honeycomb lattice.

(Light-Condensing Sheet)

The organic EL element of the present invention can enhance the luminance in a specific direction, by providing, for example, a micro lens array structure on the light extraction side of the substrate, or combining with a so-called light-condensing sheet, to condense light in a specific direction, for example, in the front direction with respect, to the light emitting face of the element.

An example of the micro lens array is quadrangular pyramids arranged two-dimensionally on the light extraction side of the substrate such that one side of the pyramid is 30 μm long and its vertical angle (apex angle) is 90°. Each side is preferably 10 μm to 100 μm long. If each side is shorter than the above-described range, coloring is caused by diffraction effects. If the sides are too long, the element is undesirably thick.

The light-condensing sheet may be, for example, those in practical use as LED back light for liquid crystal display devices. An example of such a sheet may be a brightness enhancement film (BEF) available from Sumitomo 3M Ltd. The prism sheet may have any shape. For example, ridge-shaped stripes may be formed with an apex angle of 90° and a pitch of 50-μm on a base material; each ridge of the stripes may have a rounded apex; or the pitch may be randomly varied.

In order to control the emission angle of light from the emissive element, a light diffusion plate or film may be used with a light-condensing sheet. For example, a diffusion film (LIGHT-UP) from KIMOTO CO., LTD. can be used.

(Method of Producing Organic EL Element)

An example method of producing the organic EL element according to the present invention will be described, which is composed of anode/hole injection layer/hole transfer layer/emissive layer/hole blocking layer/electron transfer layer/cathode.

On a suitable base, a thin film made of a desired electrode material such as a material for an anode is formed by a method such as deposition or sputtering such that the thin film has a thickness of 1 μm or less, and preferably 10 nm to 200 nm, to produce an anode.

On the resulting anode, an organic compound-containing thin films such as a hole injection layer, a hole transfer layer, an emissive layer, a hole blocking layer, and an electron transfer layer, which are composed of organic EL materials, are formed.

These layers each may be formed by deposition, wet processes (such as spin coating, casting, ink jet, and printing methods). In the present invention, film-forming is preferably performed by deposition, spin coating, ink jet or printing methods that readily produce uniform films and form fewer pinholes.

A different film-forming method may be used for each layer. In use of deposition, the deposition conditions vary in accordance with the kinds of compounds used, and typically are appropriately selected from the following ranges; a boat heating temperature of 50° C. to 450° C., a degree of vacuum of $10^{-6}$ Pa to $10^{-2}$ Pa, a deposition rate of 0.01 nm/second to 50 nm/second, a substrate temperature of −50° C. to 300° C., and a thickness of 0.1 μm to 5 μm.

In the formation of layers by a wet process, examples of a liquid medium in which organic EL materials according to the present invention are dissolved or dispersed include organic solvents, for example, ketones such as methyl ethyl ketone and cyclohexanone; fatty acid esters such as ethyl acetate and butyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane, DMF and DMSO. The organic EL material can be dispersed by a dispersing method such as ultra sound, high shearing force dispersion, and media dispersion.

The emissive layer is preferably formed of a coating liquid containing a compound A according to the present invention. This has an advantage of readily producing uniform films, and forming fewer pinholes.

After forming these layers, a thin film is formed on the layer with a substance for forming a cathode by a process such as deposition or sputtering such that the thin film has a thickness of 1 μm or less, and preferably in the range of 50 nm to 200 nm, to provide an anode, resulting in a desired organic EL element.

This production of the organic EL element is preferably carried out from the formation of the hole injection layer to the formation of the cathode in the same vacuum atmosphere. The organic EL element, however, may be taken out in the course of the production and may be subjected to a different film-forming step. The work is preferably conducted under a dry inert gas atmosphere.

(Applications)

The organic EL element according to the present invention can be used as a displaying device, a display, and various emissive light sources. Examples of the emissive light sources include, but not limited to, lighting devices (home-use lights and in-vehicle lights), back lights for watches and liquid crystal displays, billboards, traffic lights, light sources for optical recording media, light sources for electro-photographic copiers, light sources for optical communication processors, and light sources for optical sensors. The organic EL element according to the present invention is particularly useful in applications of back lights for liquid crystal display devices, and light sources for lighting devices.

In film-forming, the organic EL element according to the present invention may be subjected to patterning using a metal mask or by ink jet printing, as necessary. The electrodes only, or both the electrodes and emissive layers, or all layers in the element may be subjected to patterning. Any conventionally known methods can be used for producing the element.

Figure 4:
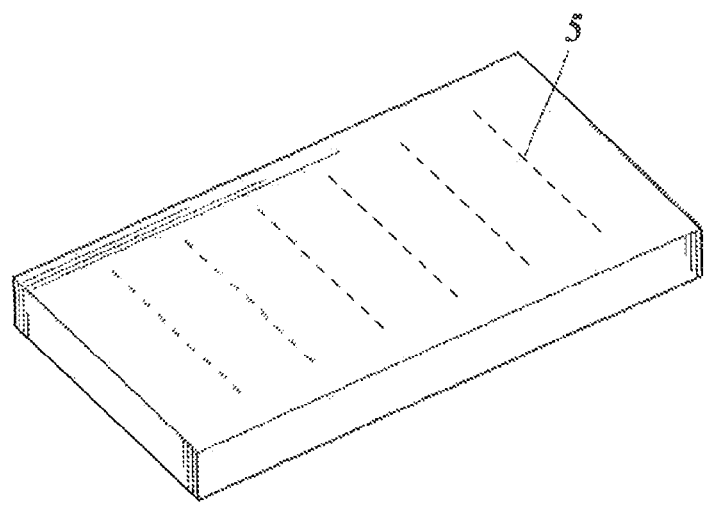
FIG. 4 is a schematic view of a full color passive-matrix display device.
Figure 4:
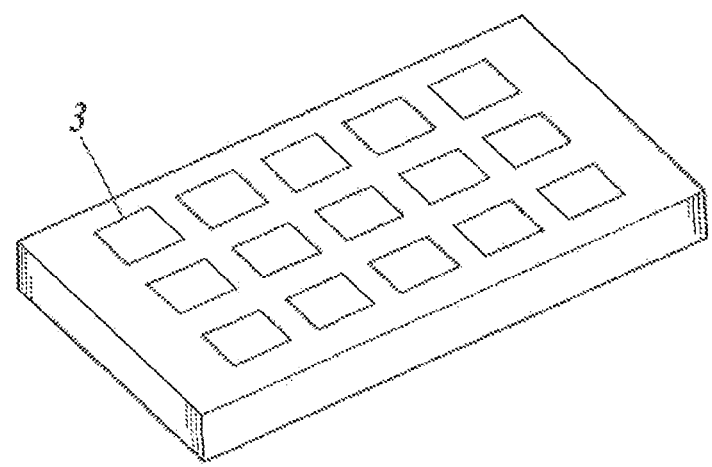
Figure 4:
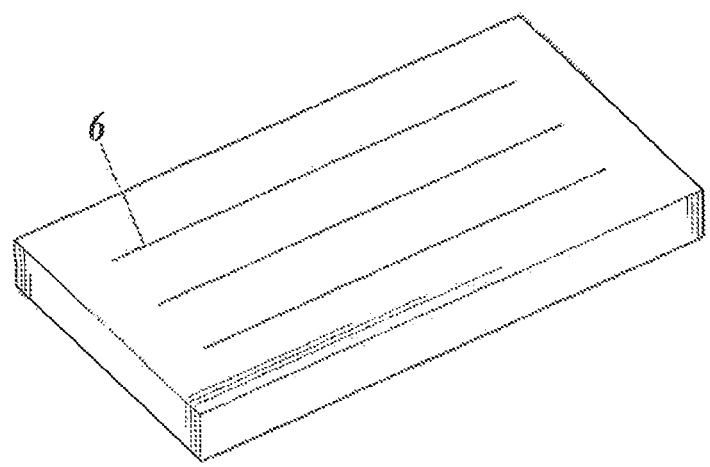

Colors emitted by the organic EL elements according to the present invention and the compounds according to the present invention is determined by matching the measured results with a spectral radiance spectrometer CS-1000 (from Konica Minolta Sensing, Inc.) on the CIE chromaticity coordinates described in "Shin-pen Shikisai Kagaku Handbook" (edited by the Color Science Association of Japan, published by University of Tokyo Press, 1985), p. 108, FIG. 4.16.

When the organic EL element according to the present invention is a white-color element, the white color means that the chromaticity in the CIE 1931 colorimetric system falls in the range of X=0.33±0.07 and Y=0.33±0.1 at a luminance of 1000 cd/m$^2$, when measured by the above method at the frontal view of a two-degree view angle.

(Display Device)

The display device according to the present invention will be described. The display device according to the present invention includes the organic EL element.

The multichromatic display device of the present invention will now be described although the display device of the present invention may be monochromatic or multichromatic. In production of the multichromatic display device, a shadow mask is provided only in the step of forming each emissive layer, and film can be formed all over the surface by a method such as vacuum deposition, casting, spin coating, ink jet process, and printing.

When only the emissive layer is subjected, to patterning, any process may be applicable and deposition, ink jetting, or printing is preferably. In a deposition process, the patterning is preferably conducted with a shadow mask.

It is possible to fabricate the element in a reversed order. That is, a cathode, an electron transfer layer, a hole blocking layer, an emissive layer, a hole transfer layer and an anode can be formed in this order.

When direct voltage is applied to the resulting multichromatic display device, the polarity of the anode is positive (+) while the polarity of the cathode is negative (−). Application of a voltage of about 2 V to 40 V to the display device causes emission. With the reverse polarity, even when direct voltage is applied, any current does not flow and causes no emission.

When alternating voltage is applied, light is emitted only in the state in which the anode is positive (+) and the cathode is negative (−). Alternating voltage of any wave form may be applied.

The multichromatic display device can be used as a displaying device, a display, and various emissive light sources. The displaying device and the display can provide full-color display using three organic EL elements which are blue, red and green elements.

Examples of the display device include television sets, personal computers, mobile instruments, AV equipment, teletext broadcasting displays, and in-vehicle information displays. Particularly, they may be used as display devices for reproducing still pictures or moving images, and in use as a display device for playback of moving images, the drive system may be a simple matrix (passive matrix) system or an active matrix system.

Examples of the emissive light sources include, but not limited to, home-use lights, in-vehicle lights, back lights for watches and liquid crystal displays, billboards, traffic lights, light sources for optical recording media, light sources for electro-photographic copier, light sources for optical communication processors, and light sources for optical sensors.

(Lighting Device)

The organic EL elements according to the present invention may also be used as lamps such as light sources for illumination or light exposure, used in projectors for projecting images, or used as display devices (a display) on which still images or sieving images are viewed directly.

The organic EL element according to the present invention may also be used, as a display device for playback of moving images using any drive system, i.e., a simple matrix (passive matrix) system or an active matrix system. Alternatively, full-color display device can be produced, using two or more organic EL elements of the present invention emitting different colors.

An example of the display device having the organic EL element of the present invention will now be described with reference to the drawings.

FIG. 1 is a schematic view showing an example display device including an organic EL element. It is a schematic view showing a display used for mobile phones, for example, which shows image information by emission of the organic EL element.

A display 1 includes a display portion A having a plurality of pixels and a control portion B which scans images on the display portion A based on the image information.

The control portion B is electrically connected to the display portion A and sends a scanning signal and an image data, signal to each of the plurality of pixels based on the external image information. Pixels for every scanning line are driven by the scanning signals and emit light sequentially based, on the image data signals, to perform image scanning, and show the image information, on the display portion A.

Figure 2:
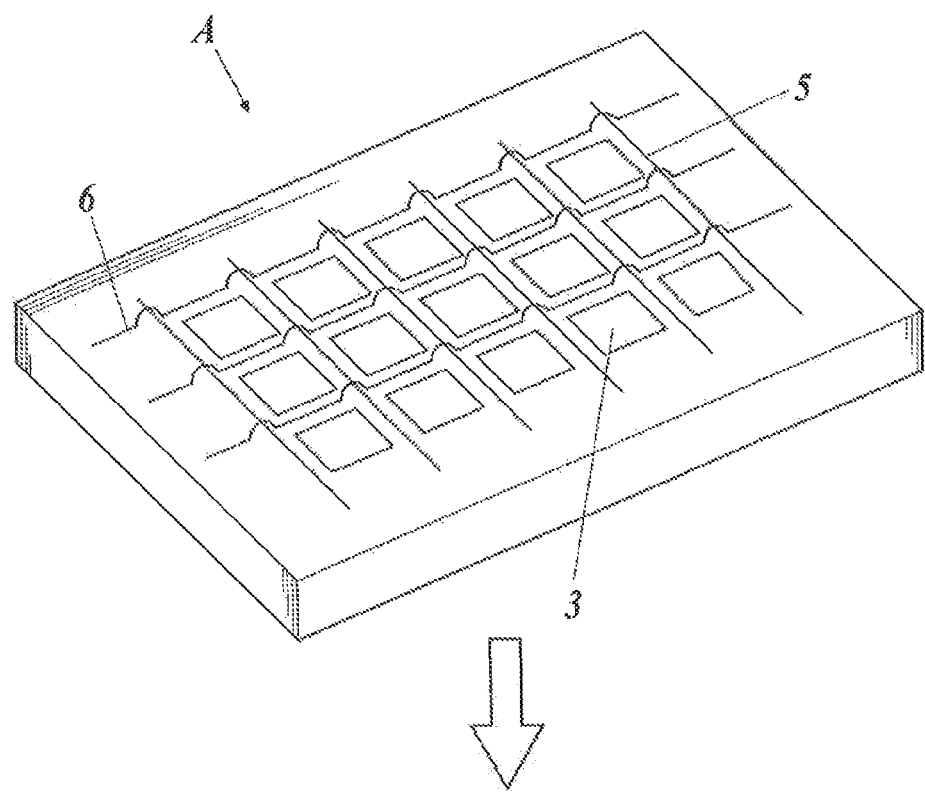
FIG. 2 is a schematic view of a display portion A.

FIG. 2 is a schematic view of the display portion A.

The display portion A has a line part containing a plurality of scanning lines 5 and data lines 6, and a plurality of pixels 3 on a substrate. Major components of the display portion A are described below.

The drawing shows an extraction of light emitted by the pixels 3 in the direction indicated by a blank arrow (downwards).

The scanning lines 5 and the data lines 6 in the line part are formed of a conductive material, and are mutually orthogonal in the form of lattice, and are each connected to the pixels 3 at the intersecting portions (details not shown).

When the scanning signal is applied from the scanning line 5 to the pixel 3, the pixel 3 receives the image data signal, from the data line 6, and emits light based on the received image data.

Pixels for emissive light in the red color region color, pixels for emissive light in the green color region, and pixels for emissive light in the blue color region are appropriately disposed on the same substrate for full-color display.

An emission process of pixels will now be described.

Figure 3:
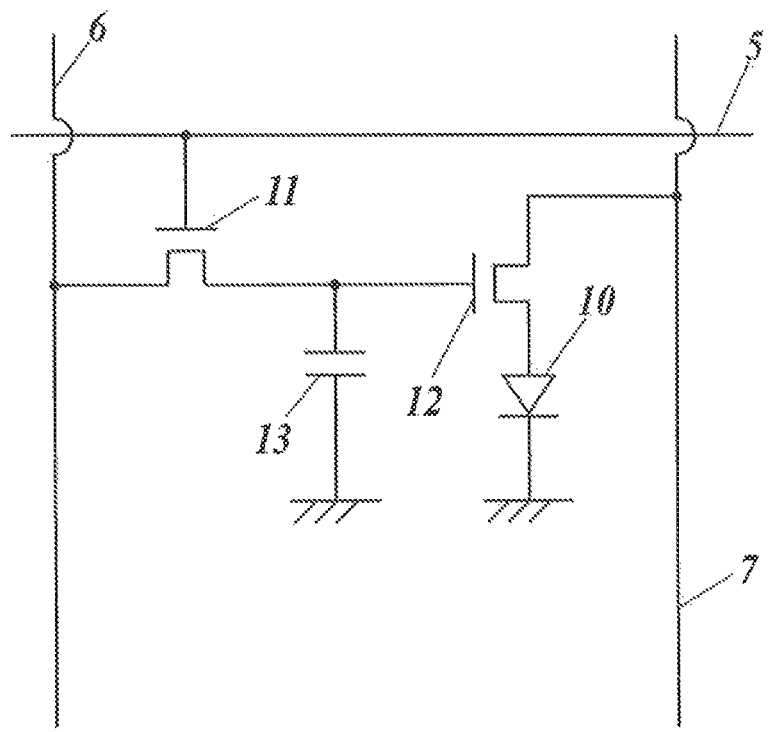
FIG. 3 is a schematic view of a pixel.

FIG. 3 is a schematic view of a pixel.

The pixel includes an organic EL element 10, a switching transistor 11, a drive transistor 12, and a capacitor 13. Red, green, and blue organic EL elements 10 are used for a plurality of pixels, and are arranged on the same substrate for full-color display.

In FIG. 3, an image data signal is applied from the control portion B through the data line 6 to the drain of the switching transistor 11. When the scanning signal is then applied from the control portion B through the scanning line 5 to the gate of the switching transistor 11, the switching transistor 11 turns on, and the image data signal having been applied to the drain is transmitted to the capacitor 13 and the gate of the drive transistor 12.

Upon the transmission of the image data signal, the capacitor 13 is charged depending on the potential of the image data signal and the drive transistor 12 turns on. The drive transistor 12 has a dram connected to a source line 7, and a source connected to the electrode of the organic EL element 10, so that electric current is supplied to the organic EL element 10 from the source line 7 depending on the potential of the image data signal applied to the gate.

When the scanning signal goes to the next scanning line 5 based on the sequential scanning by the control portion B, the switching transistor 11 turns off. However, the capacitor 13 holds the charged potential of the image data signal even after the switching transistor 11 turns off. Therefore, the drive transistor 12 is kept turned on, and thereby the organic EL element 10 continues to emit light until a next scanning signal is applied for the next time, when the next scanning signal is applied for the next, time based on the sequential scanning, the drive transistor 12 turns on depending on the potential of the next image data signal synchronized with the scanning signal, and thereby the organic EL device 10 emits light.

That is, the organic EL elements 10 of the pixels 3 are provided, with respective active elements including switching transistors 11 and drive transistors 12 which drive the organic EL elements 10 of the pixels to emit light. This emission system is referred to as the "active matrix system".

The emission of the organic EL element 10 herein may have a multilevel gradation controlled by multilevel image data signal having a multilevel gradation potential, or may be on or off at a defined yield of emission, based on a binary image data signal. The potential held, by the capacitor 13 may be retained until the next scanning signal is applied, or may be discharged immediately before the next scanning signal is applied.

In the present invention, the emission may be driven not only by the above-described active matrix system, but also by passive matrix system which allows the organic EL elements to emit light depending on the data signal only when scanned by the scanning signal, is adoptable.

FIG. 4 is a schematic view illustrating a display device of the passive matrix system. In FIG. 4, the scanning lines 5 and the image data lines 6 are opposed to each other to form a lattice, while holding the pixels 3 therebetween.

When the scanning signal from the scanning line 5 is applied by the sequential scanning, the pixel 3 connected to the applied scanning line 5 emits light depending on the image data signal.

The passive matrix system has no active devices in the pixels 3, and therefore saves the production cost.

The organic EL material of the present invention can be applied to an organic EL element causing substantially white light luminescence for the lighting device. The white light emission may be obtained by mixing multiple emitted colors from multiple emissive materials activated at the same time. The multiple emitted colors may be combined so as to contain, three maximum emission wavelengths which correspond to three primary colors of red, green and blue, or two maximum emission wavelengths which correspond to relations of complementary colors between blue and yellow, or between blue-green and orange.

Combinations of different emissive materials for obtaining a plurality of emitted colors include combinations of a plurality of phosphorescent or fluorescent materials; and combinations of fluorescent or phosphorescent materials with dye materials that are excited by the light from the fluorescent or phosphorescent materials and emit right. In the white-light organic EL element of the present invention, it is enough to combine and mix a plurality of emissive dopants.

Masks are used only in the processes of forming the emissive layer, the hole transfer layer and the electron transfer layer, which may be formed by selective coating only by placing the masks for the individual colors. On the other hand, the residual layers are provided in common irrespective of colors. Thus, an electrode film, for example, may be formed on the entire surface typically by vacuum deposition, casting, spin coating, ink jet process, printing or the like, without placing masks. Therefore, the productivity is improved. According to this method, each element itself emits white light, unlike a white-light organic EL element having multi-color emissive elements arrayed therein.

Emissive materials used for the emissive layer are not specifically limited. In the case where the device is used for a back light unit for a liquid crystal display device, white light may be obtained by appropriately selecting and combining metal complexes of the present invention or known emissive materials, to fit them to wavelength ranges corresponded to CF (color filter) characteristics.

As described above, the white emissive organic EL element according to the present invention is useful for various emissive light sources or lighting devices such as home-use lights and in-vehicle lights, lamps such as light sources for light exposure, and display devices such as back lights for liquid crystal display devices, in addition to the display device described above.

Furthermore, the white emissive organic EL element according to the present invention finds a wide range of applications, such as back lights for watches, billboards, traffic lights, light sources for optical recording media, light sources for electro-photographic copiers, light sources for optical communication processors, light sources for optical sensors, as well as common household appliances requiring display devices.

EXAMPLE

Example 1

(Measurement of 0-0 Transition Band)

The 0-0 transition band in the emission spectrum of the compound according to the invention was measured at 77 K and at 300 K in the following manner.

(Measurement of 0-0 Transition Band in Emission Spectrum)

A compound to be measured is dissolved in 2-methyltetrahydrofuran that is thoroughly deoxygenated. The solution is loaded into a measuring cell, and then irradiated with excitation light at a liquid nitrogen temperature of 77 K to measure an emission spectrum after irradiation of the excitation light.

For any compound that cannot dissolve in such a solvent, any other solvents may be used to dissolve it (the solvent effect on the emission wavelength is negligibly slight in the measurement and difference is not substantially observed in the measured values).

The determination of the 0-0 transition band will be described. The 0-0 transition band, in the present invention is defined as a maximum emission wavelength that appears on the shortest wavelength side in the spectrum obtained by the measurement described above.

Similarly, the emission spectrum for the solution prepared above is measured at 300 K to determine another 0-0 transition band. The difference between the 0-0 transition bands at 300 K and at 77 K is then calculated.

(Fabrication of Organic EL Element 1-1)

A quartz substrate measuring 100 mm×100 mm×1.1 mm was subjected to ultrasonic cleaning with isopropyl alcohol, and was then dried with dry nitrogen gas, followed by UV ozone wash for five minutes. The quartz substrate was fixed to a substrate holder of a commercially available vacuum, deposition system, A molybdenum resistive heating boat containing 200 mg of a host compound (H-1) and another molybdenum resistive heating boat containing 100 mg of a comparative compound 1 were placed in the vacuum deposition system.

In a vacuum chamber under a reduced pressure of $4\times10^{-4}$ Pa, these heating boats containing H-1 and the comparison compound 1, respectively, were electrically heated to co-deposit H-1 and the comparison compound 1 on the quartz substrate at deposition rates of 0.2 and 0.018 nm/s, respectively, thereby forming a 40-nm-thick emissive layer. The substrate temperature during the evaporation was room temperature.

The emission surface of the quarts substrate was sealed with a 300-μm-thick sealing glass as follows. The sealing glass was stacked on the quarts substrate with sealing material of epoxy-based light-curable adhesive (manufactured by Toagosei Co., Lux track LC0629B) applied around the sealing glass, and the epoxy-based light-curable adhesive was cured by UV rays. The resulting lighting device was evaluated.

(Fabrication of Organic EL Elements 1-2 to 1-11)

The organic EL elements 1-2 to 1-11 were fabricated in the same manner as the organic EL element 1-1 with the respective emissive dopants listed in Table 1 in place of the comparative compound 1.

(Measurement of PL Relative Quantum Yield)

The organic EL elements 1-1 to 1-11 were subjected to excitation of the emissive dopants by light to obtain emission spectra and their peak areas. Each peak area was obtained after correction by the absorption of the excitation light. The measurement was carried out with a spectrophotometer "U-3300" and a fluorophotometer "F-4500" by Hitachi, Ltd.

The organic EL elements 1-2 to 1-11 were normalized with reference to the peak area (as 1) of the organic EL element 1-1 (comparative compound 1). A larger peak area indicates higher emission efficiency.

Table 1 shows the results.

TABLE 1

| ORGANIC EL ELEMENT | DOPANT | DIFFERENCE IN 0-0 TRANSITION BAND BETWEEN EMISSION SPECTRA MEASURED AT 77K AND 300K (nm) | PL QUANTUM EFFICIENCY (RELATIVE VALUE) | NOTE |
|---|---|---|---|---|
| 1-1 | COMPARATIVE COMPOUND 1 | 15 | 1.00 | COMPARATIVE EXAMPLE |
| 1-2 | COMPARATIVE COMPOUND 2 | 17 | 0.88 | COMPARATIVE EXAMPLE |
| 1-3 | COMPARATIVE COMPOUND 6 | 8 | 1.05 | COMPARATIVE EXAMPLE |
| 1-4 | COMPARATIVE COMPOUND 7 | 14 | 0.75 | COMPARATIVE EXAMPLE |
| 1-5 | 1 | 3 | 1.71 | INVENTIVE EXAMPLE |
| 1-6 | 13 | 4 | 1.74 | INVENTIVE EXAMPLE |
| 1-7 | 31 | 4 | 1.65 | INVENTIVE EXAMPLE |
| 1-8 | 75 | 3 | 1.60 | INVENTIVE EXAMPLE |
| 1-9 | 88 | 4 | 1.73 | INVENTIVE EXAMPLE |
| 1-10 | 112 | 5 | 1.55 | INVENTIVE EXAMPLE |
| 1-11 | 121 | 5 | 1.62 | INVENTIVE EXAMPLE |

[Chem. 34]

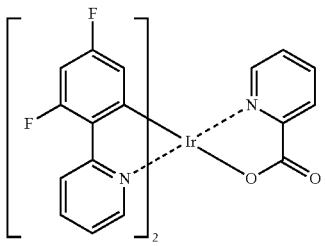

COMPARATIVE COMPOUND 1

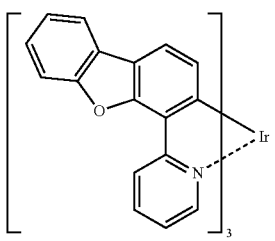

COMPARATIVE COMPOUND 2

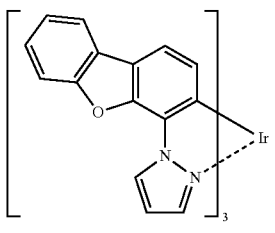

COMPARATIVE COMPOUND 3

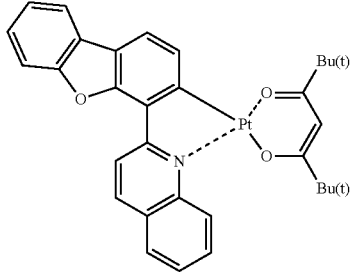

COMPARATIVE COMPOUND 4

TABLE 1-continued

| ORGANIC EL ELEMENT | DOPANT | DIFFERENCE IN 0-0 TRANSITION BAND BETWEEN EMISSION SPECTRA MEASURED AT 77K AND 300K (nm) | PL QUANTUM EFFICIENCY (RELATIVE VALUE) | NOTE |
|---|---|---|---|---|

COMPARATIVE COMPOUND 5

COMPARATIVE COMPOUND 6

COMPARATIVE COMPOUND 7

OC-18

Table 1 demonstrates chat the compounds of the invention, which exhibit a difference of 0 to 5 nm between the 0-0 transition bands at 300 K and at 77 K, have higher emission efficiencies than the comparative compounds.

Example 2

(Fabrication of Organic EL Element 2-1)

A 100-nm-thick indium tin oxide (ITO) film was formed as an anode on a glass substrate (100 mm×100 mm×1.1 mm) (the resulting substrate is available as NA45 from NH Techno Glass) and then the substrate was patterned. This transparent support substrate provided with the transparent ITO electrode was subjected to ultrasonic cleaning with isopropyl alcohol, and then dried with dry nitrogen gas, followed by UV ozone wash for five minutes.

The transparent support substrate was fixed to a substrate holder of a commercially available vacuum deposition system. Resistive heating boats made of molybdenum, each containing 200 mg of α-NPD, 200 mg of a host compound (H-1), 200 mg of BAlq, 100 mg of the comparative compound 1 (Ir-12), and 200 mg of Alq$_3$, respectively, were installed in the vacuum deposition system.

A pressure in a vacuum chamber was reduced up to $4\times10^{-4}$ Pa, and the heating boat of α-NPD was electrically heated to deposit α-NPD on the transparent support substrate at a deposition rate of 0.1 nm/s to form a 40-nm-thick hole transfer layer.

The heating boats containing H-1 and the comparative compound 1 (Ir-12), respectively, were electrically heated to co-deposit H-1 and the comparative compound 1 on the hole transfer layer at deposition rates of 0.2 and 0.012 nm/s, respectively, thereby forming a 40-nm-thick emissive layer. The temperature of the substrate during the deposition was room temperature.

Next, the heating boat carrying BAlq was electrically heated to deposit BAlq on the emissive layer at a deposition rate of 0.1 nm/s so as to form a 10-nm-thick hole blocking layer.

The heating boat carrying $Alq_3$ was then electrically heated to deposit $Alq_3$ on the hole blocking layer at a deposition rate of 0.1 nm/s so as to form a 40-nm-thick electron transfer layer. The temperature of the substrate during the evaporation was room temperature.

Subsequently, a cathode made of a 0.5-nm-thick lithium fluoride and a 110-nm-thick aluminum was formed by deposition. Thus, the organic EL element 2-1 was fabricated.

The non-emission surface of the organic EL element was covered with a glass case and a 300-μm-thick glass substrate functioning as a sealing substrate was brought into contact with the transparent support substrate such that the glass substrate covers the cathode. An epoxy-based light-curable adhesive (manufactured by Toagosei Co., Lux track LC0629B) as a sealing material was applied around the glass substrate and the epoxy-based light-curable adhesive was cured by UV rays irradiated from the glass substrate side so as to complete the sealing. The resulting lighting device 2-1 (illustrated in FIGS. 5 and 6) was evaluated.

Figure 5:
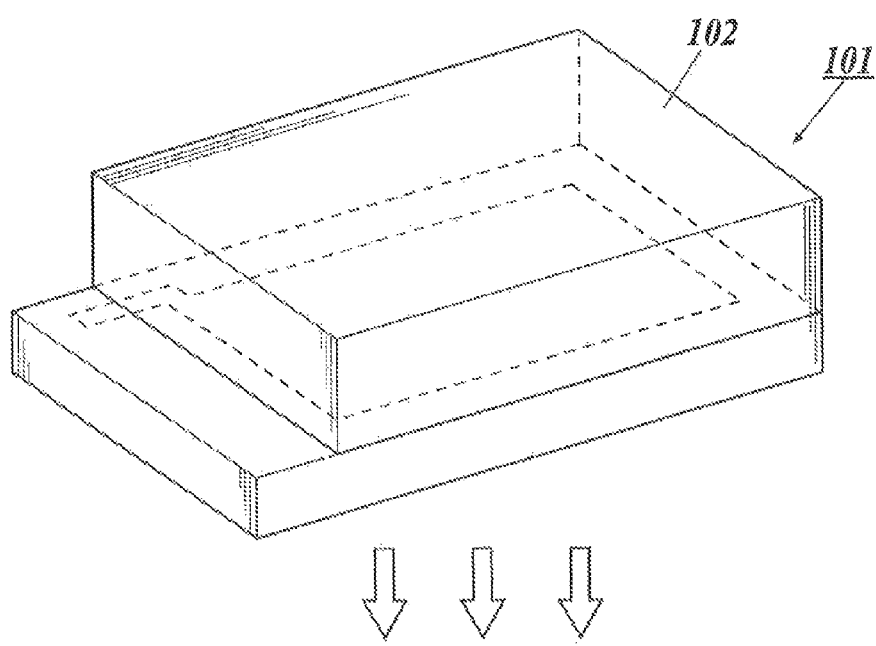
FIG. 5 is a diagrammatic illustration of a lighting device.

FIG. 5 is a schematic drawing of the lighting device. An organic EL element 101 is covered with a glass cover 102 (the organic EL element 101 was sealed by the glass cover in a glove box under nitrogen gas (high-purity nitrogen gas at purity greater than 99.999%) to avoid being exposed to air).

Figure 6:
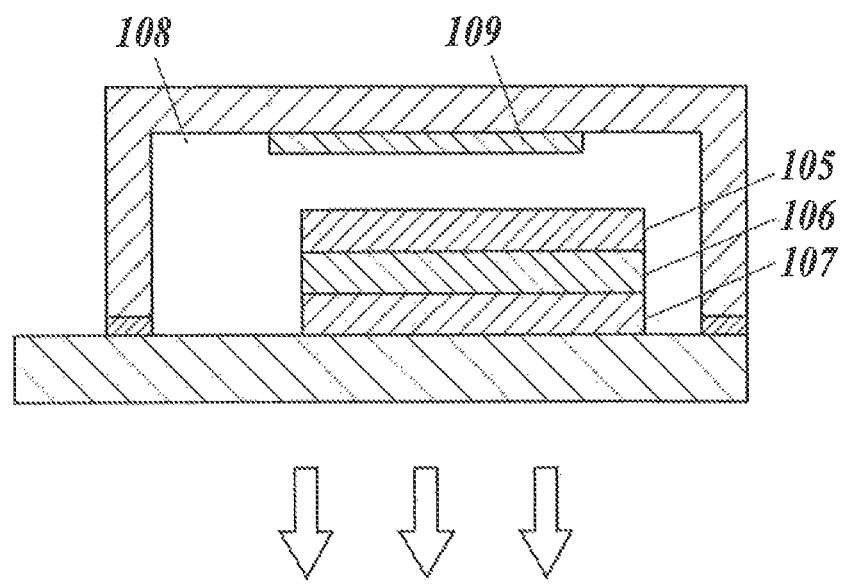
FIG. 6 is a schematic view of a lighting device.

FIG. 6 is a cross-sectional view of the lighting device. FIG. 6 shows a cathode 105, an organic EL layer 106, and a glass substrate 107 with a transparent electrode. The interior defined by the glass cover 102 is filled with nitrogen gas 108 and provided with a desiccant 109.

(Fabrication of Organic EL Elements 2-2 to 2-36)

The organic EL elements 2-2 to 2-56 were fabricated in the same manner as the organic EL element 2-1, but with the respective host compounds and emissive dopants listed in Table 2.

The lighting devices 2-2 to 2-36 were then fabricated, with the organic EL elements 2-2 to 2-36, respectively, in the same manner as the lighting device 2-1.

(Evaluation of Lighting Devices 2-1 to 2-36)

Table 2 shows the results of the evaluation, evaluated in the following manner, of the lighting devices 2-1 to 2-36 corresponding to the respective organic EL elements 2-1 to 2-36.

(Emission Efficiency (Quantum Efficiency of Extraction))

The fabricated organic EL element was tested for quantum efficiency of extraction (%) at a temperature of 23° C. under the atmosphere of dry nitrogen gas at a constant current of 2.5 mA/cm². The observed quantum efficiency was used as an indicator of emission efficiency. The measurement employed a spectral radiance spectrometer CS-1000 (available from Konica Minolta Sensing, Inc.).

The quantum efficiencies in Table 2 are represented by relative values with respect to the value (100) of the lighting device 2-1 using the organic EL element 2-1.

(Operating Life at 50° C. (Half Life at High Temperature))

The durability (operating life at 50) was evaluated in the following way.

Each lighting device was operated at a constant temperature of 50° C. and a constant current that provides an initial luminance of 1000 cd/m² to determine the time when the luminance reached half the initial luminance (500 cd/m²). The calculated time was used as an indicator of operating life at 50° C. and the index of durability. The operating lives at 50° C. are represented by relative values with respect to the value (100) of the comparative lighting device 2-1.

(Driving Voltage)

The driving voltage of each lighting device was tested on the conditions at a room temperature of about 23 to 25° C. and a constant current of 2.5 mA/cm². The driving voltages were calculated from the equation below and the results are shown in Table 2.

The driving voltages are represented by relative values with respect to the value (100) of the comparative lighting device 2-1.

Driving voltage(relative value)=(driving voltage of each lighting device)/(driving voltage of comparative lighting device 2-1)×100

A smaller value indicates a lower driving voltage than a comparative one.

(Dark Spot)

Each lighting device was evaluated by visual check of the emission surface during continuous lighting under the room temperature and a constant current of 2.5 mA/cm². Randomly selected 10 persons visually checked and ranked the lighting devices in the following categories serving as indices of control effects on dark spot (non-emissive spot) generation.

○: No one observed a dark spot,
□: One to four persons observed dark spots.
x: Five or more persons observed dark spots.

TABLE 2

| ORGANIC EL ELEMENT | LIGHTING DEVICE | HOST | DOPANT | EMISSION EFFICIENCY | HALF LIFETIME DURING HIGH-TEMPERATURE STORAGE | DRIVE VOLTAGE (RELATIVE VALUE) | DARk SPOT | NOTE |
|---|---|---|---|---|---|---|---|---|
| 2-1 | 2-1 | H-1 | COMPARATIVE COMPOUND 1 | 100 | 100 | 100 | X | COMPARATIVE EXAMPLE |
| 2-1 | 2-2 | H-1 | COMPARATIVE COMPOUND 2 | 33 | 88 | 101 | Δ | COMPARATIVE EXAMPLE |
| 2-3 | 2-3 | H-1 | COMPARATIVE COMPOUND 3 | 22 | 45 | 102 | X | COMPARATIVE EXAMPLE |
| 2-4 | 2-4 | H-1 | COMPARATIVE COMPOUND 4 | 55 | 32 | 130 | X | COMPARATIVE EXAMPLE |

TABLE 2-continued

| ORGANIC EL ELEMENT | LIGHTING DEVICE | HOST | DOPANT | EMISSION EFFICIENCY | HALF LIFETIME DURING HIGH-TEMPERATURE STORAGE | DRIVE VOLTAGE (RELATIVE VALUE) | DARk SPOT | NOTE |
|---|---|---|---|---|---|---|---|---|
| 2-5 | 2-5 | H-1 | COMPARATIVE COMPOUND 5 | 66 | 102 | 120 | Δ | COMPARATIVE EXAMPLE |
| 2-6 | 2-6 | H-1 | COMPARATIVE COMPOUND 6 | 77 | 30 | 100 | X | COMPARATIVE EXAMPLE |
| 2-7 | 2-7 | H-1 | 1 | 150 | 580 | 84 | ○ | INVENTIVE EXAMPLE |
| 2-8 | 2-8 | H-1 | 4 | 151 | 512 | 86 | ○ | INVENTIVE EXAMPLE |
| 2-9 | 2-9 | H-7 | 8 | 145 | 547 | 84 | ○ | INVENTIVE EXAMPLE |
| 2-10 | 2-10 | H-5 | 10 | 144 | 430 | 89 | ○ | INVENTIVE EXAMPLE |
| 2-11 | 2-11 | H-8 | 12 | 145 | 623 | 85 | ○ | INVENTIVE EXAMPLE |
| 2-12 | 2-12 | H-1 | 15 | 154 | 510 | 82 | ○ | INVENTIVE EXAMPLE |
| 2-13 | 2-13 | H-1 | 22 | 147 | 565 | 83 | ○ | INVENTIVE EXAMPLE |
| 2-14 | 2-14 | H-1 | 24 | 149 | 450 | 89 | ○ | INVENTIVE EXAMPLE |
| 2-15 | 2-15 | H-7 | 27 | 151 | 509 | 85 | ○ | INVENTIVE EXAMPLE |
| 2-16 | 2-16 | H-5 | 30 | 143 | 432 | 90 | ○ | INVENTIVE EXAMPLE |
| 2-17 | 2-17 | H-4 | 32 | 159 | 530 | 82 | ○ | INVENTIVE EXAMPLE |
| 2-18 | 2-18 | H-1 | 35 | 149 | 520 | 83 | ○ | INVENTIVE EXAMPLE |
| 2-19 | 2-19 | H-5 | 43 | 145 | 578 | 82 | ○ | INVENTIVE EXAMPLE |
| 2-20 | 2-20 | H-1 | 48 | 147 | 511 | 84 | ○ | INVENTIVE EXAMPLE |
| 2-21 | 2-21 | H-4 | 52 | 138 | 410 | 89 | ○ | INVENTIVE EXAMPLE |
| 2-22 | 2-22 | H-10 | 56 | 139 | 432 | 90 | ○ | INVENTIVE EXAMPLE |
| 2-23 | 2-23 | H-1 | 60 | 139 | 425 | 90 | ○ | INVENTIVE EXAMPLE |
| 2-24 | 2-24 | H-3 | 64 | 138 | 410 | 88 | ○ | INVENTIVE EXAMPLE |
| 2-25 | 2-25 | H-5 | 69 | 138 | 412 | 87 | ○ | INVENTIVE EXAMPLE |
| 2-26 | 2-26 | H-3 | 72 | 143 | 572 | 80 | ○ | INVENTIVE EXAMPLE |
| 2-27 | 2-27 | H-8 | 75 | 155 | 550 | 85 | ○ | INVENTIVE EXAMPLE |
| 2-28 | 2-28 | H-2 | 78 | 145 | 577 | 87 | ○ | INVENTIVE EXAMPLE |
| 2-29 | 2-29 | H-1 | 80 | 149 | 589 | 80 | ○ | INVENTIVE EXAMPLE |
| 2-30 | 2-30 | H-1 | 84 | 145 | 550 | 80 | ○ | INVENTIVE EXAMPLE |
| 2-31 | 2-31 | H-1 | 90 | 146 | 540 | 82 | ○ | INVENTIVE EXAMPLE |
| 2-32 | 2-32 | H-4 | 98 | 145 | 530 | 83 | ○ | INVENTIVE EXAMPLE |
| 2-33 | 2-33 | H-1 | 102 | 133 | 398 | 95 | ○ | INVENTIVE EXAMPLE |
| 2-34 | 2-34 | H-4 | 107 | 138 | 402 | 94 | ○ | INVENTIVE EXAMPLE |
| 2-35 | 2-35 | H-4 | 111 | 130 | 375 | 95 | ○ | INVENTIVE EXAMPLE |
| 2-36 | 2-36 | H-1 | 121 | 128 | 355 | 95 | ○ | INVENTIVE EXAMPLE |

It is apparent from Table 2 that the lighting devices of the invention have low driving voltages and high emission efficiencies as compared to the comparative lighting devices. In addition, the lighting devices of the invention are less prone to degradation at high temperature and to dark spot generation as compared to the comparative lighting devices.

The emissive dopants in Table 2 exhibited a difference between the 0-0 transition bands at 300 K and 77 K by 0 to 5 nm.

Example 3

(Fabrication of Organic EL Element 3-1)

A 100-nm-thick indium tin oxide (ITO) film was formed as an anode on a glass substrate (100 mm×100 mm×1.1 mm) (the resulting substrate is available as NA-45 from Avan-Strate Inc.) and then the substrate was patterned. This transparent support substrate provided with the transparent. ITO electrode was subjected to ultrasonic cleaning with isopropyl alcohol, and then dried with dry nitrogen gas, followed by UV ozone wash for five minutes.

A solution of 70% poly(3,4'-ethylenedioxythiophene)-polystyrenesulfonate (PEDOT/PSS, Baytron P Al 4083 by Bayer Holding Ltd.) in pure water was coated to form a film on the transparent support substrate by spin coating and dried at 200° C. for one hour to be a first hole transfer layer having a thickness of 30 nm.

A chlorobenzene solution of a hole transfer material (Poly(N,N'-bis(4-butylphenyl)-N,N'-bis(phenyl))benzidine (American Dye Source, Inc., ADS-254)) was coated to form a film on the first hole transfer layer by spin coating and dried at 150° C. for one hour to be a second hole transfer layer having a thickness of 40 nm.

A butyl acetate solution of a host compound (H-1) and an emissive dopant (the comparative compound 1) was coated to form a film on the second hole transfer layer by spin coating and dried at 120° C. for one hour to be an emissive layer having a thickness of 40 nm.

A 1-butanol solution of an electron transfer material (OC-18) was coated to form a film on the emissive layer by spin coating to be an insolubilized electron transfer layer having a thickness of 20 nm.

The workpiece was placed in the vacuum deposition device and a pressure of a vacuum chamber was reduced up to $4\times10^{-4}$ Pa. An electron injection layer (a 1.0-nm-thick lithium fluoride) and a cathode (a 110-nm-thick aluminum) were deposited on the workpiece. Thus, the organic EL element 3-1 was fabricated.

(Fabrication of Organic EL Elements 3-2 to 3-25)

The organic EL elements 3-2 to 3-28 were fabricated in the same manner as the organic EL element 3-1, bet with the respective host compounds for emissive layers and respective emissive dopants listed in Table 3 in place of H-1 and the comparative compound 1 of the organic EL element 3-1.

(Evaluation of Lighting Device)

For the evaluation of the resulting organic EL elements 3-1 to 3-28, corresponding lighting devices 3-1 to 3-28 (illustrated in FIGS. 5 and 6) were manufactured as follows. The non-emission surface of the organic EL element was covered with a glass case and a 300-μm-thick glass substrate functioning as a sealing substrate was brought into contact with the transparent support substrate such that the glass substrate covers the cathode. An epoxy-based light-curable adhesive (manufactured by Toagosei Co., Lux track LC0629B) as a sealing material was applied around the glass substrate and the epoxy-based light-curable adhesive was cured by UV rays irradiated from the glass substrate side so as to complete the sealing.

(Quantum Efficiency of Extraction)

The lighting device was turned, on under the condition of a room temperature of about 23 to 25° C. and a constant current of 2.5 mA/cm$^2$ to observe the luminance (L) [cd/m$^2$] immediately after the initial lighting-up. The quantum efficiency of extraction (η) was calculated from the luminance, and was used as the indicator of emission efficiency.

(Retentivity of Coating Solution for Emissive Layer)

The coating solution (mixture of H-1 (60 mg) and the comparative compound 1 (3.0 mg) dissolved in butyl acetate (12 ml)), which, was used to form an emission layer upon fabrication of the organic EL element 3-1, was left standing at room temperature for an hour to observe the precipitation for the evaluation of the retentivity of the coating solution. The evaluation was used as an indicator of effect of preventing the generation of dark spots.

○: no precipitation visually observed

□: slight precipitation visually observed x: noticeable amount of precipitation visually observed

TABLE 3

| ORGANIC EL ELEMENT | LIGHTING DEVICE | HOST | DOPANT | EMISSION EFFICIENCY | INITIAL DEGRADATION | SOLUTION RETENTIVITY | NOTE |
|---|---|---|---|---|---|---|---|
| 3-1 | 3-1 | H-1 | COMPARATIVE COMPOUND 1 | 100 | 100 | X | COMPARATIVE EXAMPLE |
| 3-2 | 3-2 | H-1 | COMPARATIVE COMPOUND 2 | 77 | 55 | Δ | COMPARATIVE EXAMPLE |
| 3-3 | 3-3 | H-1 | COMPARATIVE COMPOUND 3 | 50 | 53 | X | COMPARATIVE EXAMPLE |
| 3-4 | 3-4 | H-1 | COMPARATIVE COMPOUND 4 | 82 | 88 | Δ | COMPARATIVE EXAMPLE |
| 3-5 | 3-5 | H-1 | COMPARATIVE COMPOUND 5 | 54 | 40 | X | COMPARATIVE EXAMPLE |
| 3-6 | 3-6 | H-1 | COMPARATIVE COMPOUND 6 | 43 | 98 | X | COMPARATIVE EXAMPLE |
| 3-7 | 3-7 | H-1 | 2 | 155 | 22 | ○ | INVENTIVE EXAMPLE |
| 3-8 | 3-8 | H-1 | 3 | 145 | 27 | ○ | INVENTIVE EXAMPLE |
| 3-9 | 3-9 | H-7 | 7 | 162 | 28 | ○ | INVENTIVE EXAMPLE |
| 3-10 | 3-10 | H-5 | 11 | 158 | 25 | ○ | INVENTIVE EXAMPLE |
| 3-11 | 3-11 | H-8 | 16 | 154 | 24 | ○ | INVENTIVE EXAMPLE |
| 3-12 | 3-12 | H-1 | 17 | 140 | 35 | ○ | INVENTIVE EXAMPLE |
| 3-13 | 3-13 | H-1 | 22 | 155 | 24 | ○ | INVENTIVE EXAMPLE |
| 3-14 | 3-14 | H-1 | 24 | 148 | 39 | ○ | INVENTIVE EXAMPLE |
| 3-15 | 3-15 | H-7 | 29 | 152 | 38 | ○ | INVENTIVE EXAMPLE |
| 3-16 | 3-16 | H-5 | 34 | 150 | 25 | ○ | INVENTIVE EXAMPLE |
| 3-17 | 3-17 | H-4 | 43 | 152 | 28 | ○ | INVENTIVE EXAMPLE |
| 3-18 | 3-18 | H-1 | 54 | 132 | 40 | ○ | INVENTIVE EXAMPLE |
| 3-19 | 3-19 | H-5 | 64 | 134 | 40 | ○ | INVENTIVE EXAMPLE |
| 3-20 | 3-20 | H-1 | 72 | 140 | 38 | ○ | INVENTIVE EXAMPLE |
| 3-21 | 3-21 | H-4 | 75 | 141 | 36 | ○ | INVENTIVE EXAMPLE |
| 3-22 | 3-22 | H-10 | 82 | 140 | 39 | ○ | INVENTIVE EXAMPLE |
| 3-23 | 3-23 | H-1 | 85 | 141 | 37 | ○ | INVENTIVE EXAMPLE |
| 3-24 | 3-24 | H-3 | 95 | 140 | 38 | ○ | INVENTIVE EXAMPLE |
| 3-25 | 3-25 | H-5 | 105 | 132 | 44 | ○ | INVENTIVE EXAMPLE |
| 3-26 | 3-26 | H-1 | 108 | 134 | 42 | ○ | INVENTIVE EXAMPLE |
| 3-27 | 3-27 | H-1 | 113 | 128 | 40 | ○ | INVENTIVE EXAMPLE |
| 3-28 | 3-28 | H-4 | 126 | 127 | 44 | ○ | INVENTIVE EXAMPLE |

The luminance was observed with CS-1000 (available from Konica Minolta Sensing, Inc.). The quantum efficiency is represented by a relative value with respect to the value (100) of the lighting device 3-1.

(Initial Degradation)

The initial degradation of the lighting device was evaluated in the following manner to be used as an indicator of the endurance. Upon the evaluation of half-lifetime described above, duration until the luminance becomes 90% is determined to be used as a scale of the initial degradation. The initial degradation is represented by a relative value with respect to the value (100) of the comparative lighting device 3-1. The initial degradation is calculated by the following expression.

Initial degradation×(duration until luminance 90% of lighting device 3-1)/(duration until luminance 90% of each element)×100

A small value of initial degradation indicates delayed initial degradation of the lighting device.

Table 3 demonstrates that the lighting devices of the present invention provide high emission efficiency and high endurance at elevated temperatures and prevents generation of dark spots, compared to the comparative lighting device.

The difference between the 0-0 transition band at 77 K and that at 300 K of the emissive dopants used in Table 3 was within the range of 0 nm to 5 nm.

Example 4

(Fabrication of Display Device)
(Fabrication of Blue Emissive Element)

The organic EL element 2-7 of EXAMPLE 2 was used as a blue emissive element.

(Fabrication of Green Emissive Element)

A green emissive element including Ir-1 in place of the comparative compound 1 was fabricated in the same manner as the organic EL element 2-1 of EXAMPLE 2.

(Fabrication of Red Emissive Element)

A red emissive element including Ir-9 in place of the comparative compound 1 was fabricated in the same manner as the organic EL element 2-1 of EXAMPLE 2.

The red, green, and blue emissive organic EL elements were placed side by side on one substrate to provide an active-matrix full color display device having the configuration as illustrated in FIG. 1. FIG. 2 is a schematic view showing only the display portion A of the display device.

In specific, the display device includes a substrate, a wiring portion including scanning lines 5 and data lines 6 on the substrate, and pixels 3 (e.g., red, green, and blue emissive pixels) apposed with the wiring portion. The scanning lines 5 and the data lines 6 are composed of conductive material. Each scanning line 5 orthogonally intersects the data lines 6, and is connected to the pixels 3 at the intersections between the scanning line 5 and the data lines 6.

The pixels 3 are driven in active-matrix system including organic EL elements having predetermined emission colors and active elements including switching transistors and driving transistors. In response to scanning signals applied through the scanning lines 5, the pixels 3 receive image data signals from the data lines 6 to emit light. Such a display device having red, green, blue pixels apposed each other can be a full color display device.

The difference between the maximum emission wavelength on the shortest wavelength side in the emission spectrum measured at 77 K and that measured at 300 K of the blue emissive dopant (Example compound 1) used herein was within the range of 0 nm to 5 nm.

Such a full color display device can be driven with high emission efficiency, exhibiting high endurance and providing full color moving image having few dark spots.

INDUSTRIAL APPLICABILITY

The organic EL element of the present invention, which can be driven by low drive voltage and has high emission efficiency, long endurance and an excellent effect of preventing the occurrence of dark spots, is suitable for use in lighting devices and display devices.

DESCRIPTION OF THE REFERENCE NUMERALS

1 Display
3 Pixel
5 Scanning line
6 Data line
A Display portion.
B Control portion
10, 101 Organic EL element
102 Glass cover
105 Cathode
106 Organic EL layer
107 Glass substrate with transparent electrode
108 Nitrogen gas
109 Desiccant

The invention claimed is:

1. An organic electroluminescent element comprising an anode, a cathode, and an emissive layer, and a compound A in a layer of the organic electroluminescent element,
wherein the compound A has a difference, between a maximum emission wavelength on a shortest wavelength side in an emission spectrum measured at 300 K and a maximum emission wavelength on a shortest wavelength side in an emission spectrum measured at 77 K, of 0 nm or more and 5 nm or less,
wherein the compound A is represented by Formula (6):

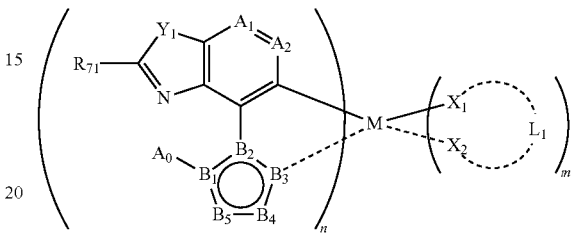

wherein $A_1$ and $A_2$ each represent a nitrogen atom or CRa;
Ra represents a hydrogen atom or a substituent;
$Y_2$ represents a nitrogen atom or CRb;
Rb represents a hydrogen atom or a substituent;
$Y_3$ represents an oxygen atom or a sulfur atom;
$R_{81}$ represents a substituent;
$R_{81}$ and Rb do not form any ring by mutual bounding;
$A_0$ represents an aromatic hydrocarbon ring group or an aromatic heterocyclic group;
$B_1$ to $B_5$ each represent a carbon atom, $CR_0$, a nitrogen atom, an oxygen atom or a sulfur atom, provided that at least one of $B_1$ to $B_5$ represents a nitrogen atom;
$R_0$ represents a hydrogen atom or a substituent;
$X_1$-$L_1$-$X_2$ represents a bidentate ligand;
$X_1$ and $X_2$ each independently represent a carbon atom or a nitrogen atom;
$L_1$ represents an atomic group that forms a bidentate ligand with $X_1$ and $X_2$;
n represents an integer of 2 or 3;
m represents an integer of (3-n); and
M is Ir.

2. The organic electroluminescent element of claim 1, wherein the layer containing the compound A is the emissive layer.

3. The organic electroluminescent element of claim 1, wherein the ring formed by $B_1$ to $B_5$ is an imidazole ring or a pyrazole ring.

4. The organic electroluminescent element of claim 1, wherein the emissive layer is a layer formed by using a coating liquid containing the compound A.

5. The organic electroluminescent element of claim 1, wherein the emissive layer emits white light.

6. A lighting device, comprising the organic electroluminescent element of claim 1.

7. A display device, comprising the organic electroluminescent element of claim 1.

* * * * *